United States Patent [19]
Cain et al.

[11] Patent Number: 5,804,532
[45] Date of Patent: Sep. 8, 1998

[54] HERBICIDAL 2-CYANO-1,3-DIONES

[75] Inventors: Paul Alfred Cain, Cary, N.C.; Susan Mary Cramp, Ongar, England; Claude Lambert, Ongar, England; Derek Ian Wallis, Ongar, England; Thomas David Yarwood, Ongar, England; Gillian Mary Little, Ongar, England; John Morris, Ongar, England; Tibor Musil, Ongar, England; Simon Neil Pettit, Ongar, England; Philip Henry Gaunt Smith, Ongar, England

[73] Assignee: Rhone-Poulenc Agriculture Limited, Essex, England

[21] Appl. No.: 458,300

[22] Filed: Jun. 2, 1995

Related U.S. Application Data

[63] Continuation-in-part of Ser. No. 304,482, Sep. 12, 1994, abandoned, which is a continuation of Ser. No. 94,881, Jul. 22, 1993, abandoned, and a continuation-in-part of Ser. No. 309,646, Sep. 21, 1994, abandoned, which is a continuation of Ser. No. 92,058, Jul. 16, 1993, abandoned, which is a continuation-in-part of Ser. No. 825,258, Jan. 24, 1992, abandoned, which is a continuation-in-part of Ser. No. 825,274, Jan. 24, 1992, abandoned.

[30] Foreign Application Priority Data

| Jan. 25, 1991 | [GB] | United Kingdom | 9101659 |
| Jan. 25, 1991 | [GB] | United Kingdom | 9101660 |
| May 18, 1993 | [GB] | United Kingdom | 9310203 |
| May 18, 1993 | [GB] | United Kingdom | 9310222 |

[51] Int. Cl.[6] .................... C07C 303/00; C07C 255/00
[52] U.S. Cl. .................. 504/309; 504/310; 504/312; 558/48; 558/57; 558/405
[58] Field of Search .................... 558/48, 57, 405; 504/309, 310, 312

[56] References Cited

U.S. PATENT DOCUMENTS

| 4,065,502 | 12/1977 | MacKay et al. | 558/405 |
| 4,175,012 | 11/1979 | MacKay et al. | 204/108 |
| 4,259,256 | 3/1981 | Hanifin, Jr. et al. | 558/405 |
| 4,781,750 | 11/1988 | Ashmore | 71/85 |

FOREIGN PATENT DOCUMENTS

| 819136 | 12/1974 | Belgium . |
| 0213892 | 3/1987 | European Pat. Off. . |
| 0374811 | 6/1990 | European Pat. Off. . |
| 0398692 | 11/1990 | European Pat. Off. . |
| 0496630 | 7/1992 | European Pat. Off. . |
| 0496631 | 7/1992 | European Pat. Off. . |

OTHER PUBLICATIONS

*Chemical Abstracts*, vol. 100, No. 20, May 14, 1984, abstract No. 157636t.
*Chemical Abstracts*, vol. 93, No. 18, Nov. 3, 1980, abstract No. 178628u.
Sasaki et al, *Bull. Chem. Soc. Japan*, vol. 44, No. 1, 1971, pp. 185–189.
Sarkar et al, *Ind. J. Chem.*, Sect. B, vol. 25B, Nov. 1986, pp. 1133–1137.
Menozzi et al, *J. Heterocyclic Chem.*, vol. 20, No. 3, 1983, pp. 645–648.

*Primary Examiner*—Joseph McKane
*Assistant Examiner*—Joseph Murray
*Attorney, Agent, or Firm*—Burns, Doane, Swecker & Mathis, L.L.P.

[57] ABSTRACT

Herbicides derived from 2-cyano-1,3-diones have the formula:

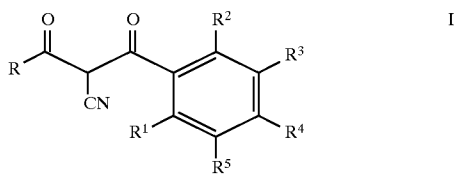

wherein R, $R^1$, $R^2$, $R^3$, $R^4$ and $R^5$ are as defined in the description. The compounds are intended for use pre- and post-emergence as selective herbicides in maize and a large number of other monocotyledon crops.

95 Claims, No Drawings

HERBICIDAL 2-CYANO-1,3-DIONES

CROSS REFERENCE TO RELATED APPLICATIONS

This application is a continuation-in-part of application Ser. No. 08/304,482 filed Sep. 12, 1994, now abandoned (which is a continuation of application Ser. No. 08/094,881 filed Jul. 22, 1993, now abandoned) and application Ser. No. 08/309,646 filed Sep. 21, 1994, now abandoned which is a continuation of application Ser. No. 08/092,058 filed Jul. 16, 1993, now abandoned (which itself is a continuation-in-part of application Ser. Nos. 07/825,258 and 07/825,274, both filed Jan. 24, 1992, both now abandoned). All of the earlier related applications are incorporated by reference herein in their entireties and relied upon.

DESCRIPTION OF THE INVENTION

This invention relates to novel 2-cyano-1,3-dione derivatives, compositions containing them, processes for their preparation and their use as herbicides.

The present invention provides 2-cyano-1,3-dione derivatives of formula (I):

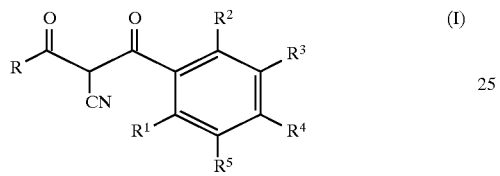

wherein:
R represents:
- a straight- or branched-chain alkyl, alkenyl or alkynyl group containing up to six carbon atoms which is optionally substituted by one or more halogen atoms;
- a cycloalkyl group containing from three to six carbon atoms optionally substituted by one or more $R^6$ groups or one or more groups selected from halogen, $-CO_2R^7$, $-SR^{71}$ and $-OR^{71}$;
- a cycloalkenyl group containing five or six carbon atoms optionally substituted by one or more $R^6$ groups or one or more halogen atoms or a group, $-CO_2R^7$;
- a group of the formula $-(CH_2)_p$-phenyl-$(R^{21})_r$;

$R^1$ represents:
- a hydrogen, chlorine, bromine or fluorine atom; or a group selected from methyl, methoxy and trifluoromethyl;

$R^2$, $R^3$, $R^4$ and $R^5$, which may be the same or different, each represents:
- the hydrogen atom;
- a straight- or branched-chain alkyl, alkenyl or alkynyl group containing up to six carbon atoms optionally substituted by one or more halogen atoms;
- a straight- or branched-chain alkyl group containing up to six carbon atoms which is substituted by a group $-OR^6$;
- a halogen atom;
- a group selected from nitro, cyano, $-CO_2R^6$, $-COR^7$, $-X-S(O)_qR^8$, $-S(O)_nR^9$, $-O(CH_2)_mOR^6$, $-NR^{10}R^{11}$, $-CONR^{10}R^{15}$ and $-OR^{61}$;
- phenyl optionally substituted by from one to five groups $R^{21}$ which may be the same or different; or
- a cycloalkyl group containing from three to six carbon atoms;

$R^6$ represents a straight- or branched-chain alkyl, alkenyl or alkynyl group containing up to six carbon atoms optionally substituted by one or more halogen atoms; or
- a cycloalkyl group containing from three to six carbon atoms;

$R^{61}$ represents:
- a straight- or branched-chain alkyl, alkenyl or alkynyl group containing up to six carbon atoms optionally substituted by one or more halogen atoms;
- phenyl optionally substituted by from one to five groups $R^{21}$ which may be the same or different; or
- a cycloalkyl group containing from three to six carbon atoms;

$R^7$ represents a straight- or branched-chain alkyl group containing up to six carbon atoms optionally substituted by one or more halogen atoms; or
- a cycloalkyl group containing from three to six carbon atoms;

$R^{71}$ represents a straight- or branched-chain alkyl group containing up to three carbon atoms;

$R^8$ represents:
- a straight- or branched-chain alkyl, alkenyl or alkynyl group containing up to six carbon atoms optionally substituted by one or more halogen atoms;
- a cycloalkyl group containing from three to six carbon atoms;
- phenyl optionally substituted by from one to five groups $R^{21}$ which may be the same or different; or
- a group selected from $-CH_2CN$, $-CH_2CO_2R^6$ and $-NR^{10}R^{11}$;

$R^9$ represents:
- a straight- or branched-chain alkyl, alkenyl or alkynyl group containing up to six carbon atoms optionally substituted by one or more halogen atoms;
- a cycloalkyl group containing from three to six carbon atoms;
- phenyl optionally substituted by from one to five groups $R^{21}$ which may be the same or different; or
- a group selected from $-CH_2CN$, $-CH_2CO_2R^6$ and $-NR^{10}R^{11}$;

$R^{10}$ represents:
- the hydrogen atom;
- a straight- or branched-chain alkyl group containing up to six carbon atoms optionally substituted by one or more halogen atoms;
- a cycloalkyl group containing from three to six carbon atoms;
- where $R^7$ and $R^{10}$ are part of a group $-CONR^7R^{10}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{11}$ represents:
- a straight- or branched-chain alkyl group containing up to six carbon atoms optionally substituted by one or more halogen atoms;
- a cycloalkyl group containing from three to six carbon atoms;
- or a group selected from $-COR^7$, $-CO_2R^7$ and $-CONR^7R^{10}$;
- where $R^{10}$ and $R^{11}$ are part of a group $-NR^{10}R^{11}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

X represents oxygen, —N($R^{12}$)—, —(—$CR^{13}R^{14}$—)$_r$— or —S(O)$_u$—;

$R^{12}$ represents:
the hydrogen atom;
a straight- or branched-chain alkyl, alkenyl or alkynyl group containing up to six carbon atoms optionally substituted by one or more halogen atoms;
a cycloalkyl group containing from three to six carbon atoms;
phenyl optionally substituted by from one to five groups $R^{21}$ which may be the same or different; or
a group selected from —$COR^7$, —$CO_2R^7$, —$CONR^7R^{10}$, —$OR^{17}$ and —$SO_2R^7$;

$R^{13}$ and $R^{14}$, which may be the same or different, each represents the hydrogen atom or a straight- or branched-chain alkyl group containing up to six carbon atoms optionally substituted by one or more halogen atoms;

$R^{15}$ represents a group selected from $R^7$ and —$OR^{17}$;
where $R^{10}$ and $R^{15}$ are part of a group —$CONR^{10}R^{15}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{17}$ represents a straight- or branched-chain alkyl group containing up to six carbon atoms;

$R^{21}$ represents:
a halogen atom or a group selected from $R^7$, nitro, cyano, —$CO_2R^7$, —$S(O)_nR^7$, —$NR^{10}R^{11}$ and —$OR^7$;

m represents one, two or three;
n represents zero, one or two;
p represents zero or one;
q represents zero, one or two;
when X represents —N($R^{12}$)— or oxygen, q represents two;
when X represents —S(O)$_u$—, q represents zero or two;
r represents zero or an integer from one to five;
t represents an integer from one to four; where t is greater than one the groups —(CR$^{13}$R$^{14}$)— may be the same or different;
u represents zero or two;

and agriculturally acceptable salts or metal complexes thereof, which possess valuable properties.

It will be understood that the compounds may exist in enolic tautomeric forms. All such forms are embraced by the present invention.

Compounds of formula I may exist in enolic tautomeric forms that may give rise to geometric isomers around the enolic double bond.

Furthermore in certain cases the groups $R^1$, $R^2$, $R^3$, $R^4$ and $R^5$ may give rise to stereoisomers and geometric isomers. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, formed by compounds of formula (I) containing an amino group, include salts with inorganic acids, for example hydrochlorides, sulphates, phosphates and nitrates and salts with organic acids, for example acetic acid.

By the term "metal complexes" is meant compounds in which one or both of the oxygen atoms of the 1,3-dione act as chelating agents to a metal cation. Examples of such cations include zinc, manganese, cupric, cuprous, ferric, ferrous, titanium and aluminium.

The compounds of the invention, in some aspects of their activity, show advantages over known compounds.

DETAILED DESCRIPTION OF THE INVENTION

In one embodiment the invention provides 2-cyano-1,3-dione derivatives of formula (I) wherein:

R represents:
a straight- or branched-chain alkyl group containing up to six carbon atoms which is optionally substituted by one or more halogen atoms; or
a cycloalkyl group containing from three to six carbon atoms optionally substituted by one or more $R^7$ groups;

$R^1$ represents the hydrogen atom;

$R^2$, $R^3$, $R^4$ and $R^5$, which may be the same or different, each represents:
the hydrogen atom;
a straight- or branched-chain alkyl, alkenyl or alkynyl group containing up to six carbon atoms optionally substituted by one or more halogen atoms;
a straight- or branched-chain alkyl group containing up to six carbon atoms which is substituted by a group —$OR^6$;
a halogen atom;
phenyl optionally substituted by from one to three groups $R^{21}$ which may be the same or different;
a group selected from —$COR^7$, nitro, cyano, —$CO_2R^6$, —$S(O)_nR^9$, —$O(CH_2)_mOR^6$, —$N(R^{12})SO_2R^8$, —$CONR^{10}R^{15}$ and —$OR^{61}$;
provided that at least one of the groups $R^2$ to $R^5$ represents —$N(R^{12})SO_2R^8$;

$R^6$ represents:
a straight- or branched-chain alkyl, alkenyl or alkynyl group containing up to six carbon atoms optionally substituted by one or more halogen atoms; or
a cycloalkyl group containing from three to six carbon atoms;

$R^{61}$ represents:
a straight- or branched-chain alkyl, alkenyl or alkynyl group containing up to six carbon atoms optionally substituted by one or more halogen atoms;
a cycloalkyl group containing from three to six carbon atoms; or
phenyl optionally substituted by from one to five groups $R^{21}$ which may be the same or different;

$R^7$ represents:
a straight- or branched-chain alkyl group containing up to six carbon atoms optionally substituted by one or more halogen atoms;
or a cycloalkyl group containing from three to six carbon atoms;

$R^8$ represents:
a straight- or branched-chain alkyl, alkenyl or alkynyl group containing up to six carbon atoms optionally substituted by one or more halogen atoms;

a cycloalkyl group containing from three to six carbon atoms;
phenyl optionally substituted by from one to five groups $R^{21}$ which may be the same or different; or —$NR^{10}R^{11}$;

$R^9$ represents:
a straight- or branched-chain alkyl, alkenyl or alkynyl group containing up to six carbon atoms optionally substituted by one or more halogen atoms;
a cycloalkyl group containing from three to six carbon atoms;
or phenyl optionally substituted by from one to five groups $R^{21}$ which may be the same or different;

$R^{10}$ represents hydrogen or a straight- or branched-chain alkyl group containing up to six carbon atoms optionally substituted by one or more halogen atoms;

$R^{11}$ represents:
a straight- or branched-chain alkyl group containing up to six carbon atoms optionally substituted by one or more halogen atoms;
where $R^{10}$ and $R^{21}$ are part of a group —$NR^{10}R^{11}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{12}$ represents:
the hydrogen atom; or
a straight- or branched-chain alkyl, alkenyl or alkynyl group containing up to six carbon atoms optionally substituted by one or more halogen atoms;
a cycloalkyl group containing from three to six carbon atoms;
phenyl optionally substituted by from one to five groups $R^{21}$ which may be the same or different; or a group —$OR^{17}$;

$R^{15}$ represents a group selected from $R^7$ and —$OR^{17}$;
where $R^{10}$ and $R^{15}$ are part of a group —$CONR^{10}R^{15}$ they may, together with the nitrogen to which they are attached, form a 5 or 6 membered ring optionally containing an oxygen or nitrogen atom in the ring (e.g. pyrrolidine, morpholine, pyrrole, piperidine and piperazine), wherein the ring is optionally substituted by one or more alkyl groups containing up to 3 carbon atoms;

$R^{17}$ represents a straight- or branched-chain alkyl group containing up to six carbon atoms;

$R^{21}$ represents
a halogen atom;
a straight- or branched-chain alkyl group containing up to three carbon atoms optionally substituted by one or more halogen atoms;
or a group selected from nitro, cyano, —$S(O)_nR^7$ and —$OR^7$;
m represents one, two or three; and
n represents zero, one or two.

In this first embodiment, a preferred class of compounds of formula (I) are those wherein:
R represents:
a straight- or branched-chain alkyl group containing up to six carbon atoms which is optionally substituted by one or more halogen atoms; or
a cycloalkyl group containing from three to six carbon atoms optionally substituted by one or more methyl groups;

$R^2$, $R^3$, $R^4$ and $R^5$, which may be the same or different, each represents:
a hydrogen or halogen atom;
a straight- or branched-chain alkyl, alkenyl or alkynyl group containing up to six carbon atoms optionally substituted by one or more halogen atoms;
a straight- or branched-chain alkyl group containing up to six carbon atoms which is substituted by a group —$OR^6$;
phenyl optionally substituted by from one to three groups $R^{21}$ which may be the same or different;
or a group selected from —$COR^7$, cyano, nitro, —$CO_2R^6$, —$S(O)_nR^9$, —$O(CH_2)_mOR^6$, —$N(R^{12})SO_2R^8$ and —$OR^{61}$;

$R^6$ and $R^7$ which may be the same or different, each represents:
a straight- or branched-chain alkyl group containing up to six carbon atoms optionally substituted by one or more halogen atoms;
or a cycloalkyl group containing from three to six carbon atoms;

$R^{61}$ and $R^9$, which may be the same or different, each represents:
a straight- or branched-chain alkyl or alkenyl group containing up to six carbon atoms optionally substituted by one or more halogen atoms;
a straight- or branched-chain alkynyl group containing from three to six carbon atoms;
a cycloalkyl group containing three to six carbon atoms;

$R^8$ represents:
a straight- or branched-chain alkyl or alkenyl group containing up to six carbon atoms optionally substituted by one or more halogen atoms;
a straight- or branched-chain alkynyl group containing from three to six carbon atoms;
a cycloalkyl group containing three to six carbon atoms; or
phenyl optionally substituted by from one to three groups $R^{21}$ which may be the same or different;

$R^{12}$ represents:
the hydrogen atom; or
a straight- or branched-chain alkyl or alkenyl group containing up to six carbon atoms optionally substituted by one or more halogen atoms;
a straight- or branched-chain alkynyl group containing from three to six carbon atoms;
or a cycloalkyl group containing three to six carbon atoms;

$R^{21}$ represents:
a halogen atom;
a straight- or branched-chain alkyl group containing up to three carbon atoms optionally substituted by one or more halogen atoms; or
a group selected from nitro, cyano, —$S(O)_nR^7$ or —$OR^7$;
m represents two or three; and
n represents zero, one or two.

A further preferred class of compounds of formula (I) within this first embodiment are those wherein:
R represents:
a straight- or branched-chain alkyl group containing up to three carbon atoms; or
a cycloalkyl group containing three or four carbon atoms optionally substituted by a methyl group;

$R^2$, $R^3$ and $R^4$ which may be the same or different, each represents:

a hydrogen, chlorine, bromine or fluorine atom; or
a straight- or branched-chain alkyl, alkenyl or alkynyl group containing up to four carbon atoms optionally substituted by one or more halogen atoms;
a straight- or branched-chain alkyl group containing up to four carbon atoms which is substituted by a group —$OR^6$; or
a group selected from —$COR^7$, —$CO_2R^6$, —$S(O)_nR^9$, —$O(CH_2)_mOR^6$, —$N(R^{12})SO_2R^8$ and —$OR^{61}$;
$R^5$ represents the hydrogen atom;
$R^6$, $R^7$, and $R^9$ which may be the same or different, each represents:
a straight- or branched-chain alkyl group containing up to four carbon atoms optionally substituted by one or more chlorine, bromine or fluorine atoms; or
a cyclopropyl group;
$R^{61}$ and $R^8$, which may be the same or different, each represents:
a straight- or branched-chain alkyl or alkenyl group containing up to four carbon atoms optionally substituted by one or more chlorine, bromine or fluorine atoms;
a straight- or branched-chain alkynyl group containing three or four carbon atoms; or
a cyclopropyl group;
$R^{12}$ represents:
the hydrogen atom;
a straight- or branched-chain alkyl or alkenyl group containing up to four carbon atoms optionally substituted by one or more chlorine, bromine or fluorine atoms;
a straight- or branched-chain alkynyl group containing three or four carbon atoms; or
a cyclopropyl group;
m represents two or three; and
n represents zero, one or two.

A further preferred class of compound within this first embodiment are those wherein:
R represents:
a methyl, ethyl, isopropyl, cyclopropyl or 1-methylcyclopropyl group;
$R^2$, $R^3$ and $R^4$ which may be the same or different, each represents:
a hydrogen, bromine, chlorine or fluorine atom; or
a straight- or branched-chain alkyl or alkenyl group containing up to four carbon atoms optionally substituted by one or more chlorine, bromine or fluorine atoms;
a group selected from —$COR^7$, —$CO_2R^6$, —$SR^9$—, —$O(CH_2)_mOR^6$, —$OR^{61}$ and —$N(R^{12})SO_2R^8$; or
a straight- or branched chain alkyl group containing up to four carbon atoms which is substituted by —$OR^6$;
$R^5$ represents the hydrogen atom;
$R^6$, $R^7$ and $R^9$ which may be the same or different, each represents a straight- or branched-chain alkyl group containing up to three carbon atoms;
$R^{61}$ represents:
a straight- or branched-chain alkyl group containing up to four carbon atoms optionally substituted by one or more chlorine, bromine or fluorine atoms;
a straight- or branched-chain alkenyl or alkynyl group containing three or four carbon atoms; or
a cyclopropyl group;
$R^8$ represents:
a straight- or branched-chain alkyl group containing up to three carbon atoms optionally substituted by one or more chlorine, bromine, or fluorine atoms; or
an allyl group optionally substituted by one or more chlorine, fluorine or bromine atoms;
$R^{12}$ represents:
the hydrogen atom;
a straight- or branched-chain alkyl group containing up to three carbon atoms optionally substituted by one or more chlorine, bromine, or fluorine atoms; or
an allyl group optionally substituted by one or more chlorine, fluorine or bromine atoms;
m represents two or three.

In a second embodiment the invention provides 2-cyano-1,3-dione derivatives of formula (I) wherein:
R represents:
a straight- or branched-chain alkyl group containing up to six carbon atoms which is optionally substituted by one or more halogen atoms; or
a cycloalkyl group containing from three to six carbon atoms optionally substituted by one or more $R^7$ groups;
$R^1$ represents the hydrogen atom;
$R^2$, $R^3$, $R^4$ and $R^5$, which may be the same or different, each represents:
the hydrogen atom;
a halogen atom;
a straight- or branched-chain alkyl, alkenyl or alkynyl group containing up to six carbon atoms optionally substituted by one or more halogen atoms;
phenyl optionally substituted by up to three groups $R^{21}$ which may be the same or different;
a straight- or branched-chain alkyl group containing up to six carbon atoms which is substituted by a group —$OR^6$;
a group selected from nitro, cyano, —$CO_2R^6$, —$COR^7$, —$S(O)_nR^9$, —$O(CH_2)_mOR^6$, —$N(R^{12})SO_2R^8$, —$OR^{61}$, —$OSO_2R^8$, —$CONR^{10}R^{15}$ and —$(CR^{13}R^{14})_r$—$S(O)_qR^8$;
provided that at least one of the groups $R^2$ to $R^5$ represents —$(CR^{13}R^{14})_r$—$S(O)_qR^8$;
$R^6$ represents a straight- or branched-chain alkyl, alkenyl or alkynyl group containing up to six carbon atoms optionally substituted by one or more halogen atoms; or
a cycloalkyl group containing from three to six carbon atoms;
$R^{61}$ represents:
a straight- or branched-chain alkyl, alkenyl or alkynyl group containing up to six carbon atoms optionally substituted by one or more halogen atoms;
a cycloalkyl group containing from three to six carbon atoms;
or phenyl optionally substituted by from one to five groups $R^{21}$ which may be the same or different;
$R^7$ represents a straight- or branched-chain alkyl group containing up to six carbon atoms optionally substituted by one or more halogen atoms; or
a cycloalkyl group containing from three to six carbon atoms;
$R^8$ represents:
a straight- or branched-chain alkyl, alkenyl or alkynyl group containing up to six carbon atoms optionally substituted by one or more halogen atoms;
a cycloalkyl group containing from three to six carbon atoms;
phenyl optionally substituted by from one to five groups $R^{21}$ which may be the same or different; or —$NR^{10}R^{11}$;
$R^9$ represents:

a straight- or branched-chain alkyl, alkenyl or alkynyl group containing up to six carbon atoms optionally substituted by one or more halogen atoms;

a cycloalkyl group containing from three to six carbon atoms; or phenyl optionally substituted by from one to five groups $R^{21}$ which may be the same or different;

$R^{10}$ represents hydrogen a straight- or branched-chain alkyl group containing up to six carbon atoms optionally substituted by one or more halogen atoms;

$R^{11}$ represents:

a straight- or branched-chain alkyl group containing up to six carbon atoms optionally substituted by one or more halogen atoms;

or a group selected from —$COR^7$, —$CO_2R^7$ and —$CONR^7R^{10}$;

where $R^{10}$ and $R^{11}$ are part of a group —$NR^{10}R^{11}$ they may, together with the nitrogen to which they are attached, may form a 5 or 6 membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{12}$ represents:

the hydrogen atom;

a straight- or branched-chain alkyl, alkenyl or alkynyl group containing up to six carbon atoms optionally substituted by one or more halogen atoms;

a cycloalkyl group containing from three to six carbon atoms;

phenyl optionally substituted by from one to five groups $R^{21}$ which may be the same or different;

or a group —$OR^{17}$;

$R^{13}$ and $R^{14}$, which may be the same or different, each represents the hydrogen atom or a straight- or branched-chain alkyl group containing up to six carbon atoms optionally substituted by one or more halogen atoms;

$R^{15}$ represents a group selected from $R^7$ and —$OR^{17}$;

where $R^{10}$ and $R^{15}$ are part of a group —$CONR^{10}R^{15}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{17}$ represents a straight- or branched-chain alkyl group containing up to six carbon atoms;

$R^{21}$ represents:

a halogen atom;

a straight- or branched-chain alkyl group containing up to three carbon atoms optionally substituted by one or more halogen atoms;

or a group selected from nitro, cyano, —$S(O)_nR^7$ and —$OR^7$;

m represents one, two or three;

n represents zero, one or two;

q represents zero, one or two; and t represents an integer from one to four; where t is greater than one the groups —$(CR^{13}R^{14})$— may be the same or different.

In this second embodiment a preferred class of compounds are those wherein:

R represents:

a straight- or branched-chain alkyl group containing up to six carbon atoms optionally substituted by one or more halogen atoms; or a cycloalkyl group containing from three to six carbon atoms optionally substituted by one or more methyl groups;

$R^2$, $R^3$, $R^4$ and $R^5$, which may be the same or different, each represents:

a hydrogen or halogen atom; or a straight- or branched-chain alkyl, alkenyl or alkynyl group containing up to six carbon atoms optionally substituted by one or more halogen atoms;

a straight- or branched-chain alkyl group containing up to six carbon atoms which is substituted by —$OR^6$; or a group selected from —$COR^7$, —$CO_2R^6$, cyano, nitro, —$O(CH_2)_mOR^6$; —$OR^{61}$, —$N(R^{12})SO_2R^8$, —$OSO_2R^8$, —$S(O)_nR^9$ and —$(CR^{13}R^{14})_tSO_qR^8$;

$R^6$ and $R^7$, which may be the same or different each represents:

a straight- or branched-chain alkyl group containing up to six carbon atoms optionally substituted by one or more halogen atoms;

or a cycloalkyl group containing three or four carbon atoms;

$R^{61}$ and $R^9$, which may be the same or different, each represents:

a straight- or branched-chain alkyl or alkenyl group containing up to six carbon atoms optionally substituted by one or more halogen atoms;

a straight- or branched-alkynyl group containing from three to six carbon atoms optionally substituted by one or more halogen atoms;

a cycloalkyl group containing three to six carbon atoms;

$R^8$ represents:

a straight- or branched-chain alkyl or alkenyl group containing up to six carbon atoms optionally substituted by one or more halogen atoms;

a straight- or branched-alkynyl group containing from three to six carbon atoms optionally substituted by one or more halogen atoms;

a cycloalkyl group containing three to six carbon atoms; or phenyl optionally substituted by from one to three groups $R^{21}$ which may be the same or different;

$R^{12}$ represents:

the hydrogen atom;

a straight- or branched-chain alkyl or alkenyl group containing up to six carbon atoms optionally substituted by one or more halogen atoms;

a straight- or branched-alkynyl group containing from three to six carbon atoms optionally substituted by one or more halogen atoms;

a cycloalkyl group containing three to six carbon atoms;

$R^{13}$ and $R^{14}$, which may be the same or different, each represents:

a hydrogen atom; or a straight- or branched-chain alkyl group containing up to six carbon atoms optionally substituted by one or more halogen atoms;

$R^{21}$ represents:

a halogen atom;

a straight- or branched-chain alkyl group containing up to three carbon atoms optionally substituted by one or more halogen atoms; or a group selected from nitro, cyano, —S(O)$_n$R$^7$ and —OR$^7$;
m represents two or three;
n represents zero, one or two;
q represents zero, one or two; and
t represents one or two.

A further preferred class of compounds within this second embodiment are those wherein:

R represents:
  a straight- or branched chain alkyl group containing up to three carbon atoms; or
  a cycloalkyl group containing thee or four carbon atoms optionally substituted by one or more methyl groups;

R$^2$, R$^3$ and R$^4$, which may be the same or different, each represents:
  a hydrogen, chlorine, bromine or fluorine atom; or
  a straight- or branched-chain alkyl or alkenyl group containing up to four carbon atoms optionally substituted by one or more chlorine, bromine or fluorine atoms;
  a straight- or branched-chain alkynyl group containing up to four carbon atoms;
  a straight- or branched-chain alkyl group containing up to four carbon atoms which is substituted by —OR$^6$; or
  a group selected from —COR$^7$, —CO$_2$R$^6$, —S(O)$_n$R$^9$, —O(CH$_2$)$_m$OR$^6$, —N(R$^{12}$)SO$_2$R$^8$, —OR$^{61}$, —(CR$^{13}$R$^{14}$)$_t$S(O)$_q$R$^8$ and —OSO$_2$R$^8$;
  provided at least one of the groups R$^2$ to R$^4$ represents —(CR$^{13}$R$^{14}$)$_t$—S(O)$_q$R$^8$;

R$^5$ represents the hydrogen atom;

R$^6$, R$^7$, R$^8$ and R$^9$, which may be the same or different, each represents:
  a straight- or branched-chain alkyl group containing up to four carbon atoms optionally substituted by one or more chlorine, bromine or fluorine atoms; or
  a cyclopropyl group;

R$^{61}$ represents:
  a straight- or branched-chain alkyl or alkenyl group containing up to four carbon atoms optionally substituted by one or more chlorine, bromine or fluorine atoms;
  a straight- or branched-chain alkynyl group containing three or four carbon atoms, or
  a cyclopropyl group;

R$^{12}$ represents:
  the hydrogen atom; or
  a straight- or branched-chain alkyl or alkenyl group containing up to four carbon atoms optionally substituted by one or more chlorine, bromine or fluorine atoms;
  a straight- or branched-chain alkynyl group containing three or four carbon atoms, or
  a cyclopropyl group;

R$^{13}$ and R$^{14}$ which may be the same or different, each represents:
  the hydrogen atom; or
  a straight- or branched-chain alkyl group containing up to three carbon atoms;
  m represents two or three;
  n represents zero, one or two;
  q represents zero, one or two; and
  t represents one.

A further preferred class of compounds of formula (I) within this second embodiment are those wherein:

R represents:
  a methyl, ethyl, isopropyl, cyclopropyl or 1-methylcyclopropyl group;

R$^2$, R$^3$ and R$^4$, which may be the same or different, each represents:
  a hydrogen, chlorine, bromine or fluorine atom; or
  a straight- or branched-chain alkyl or alkenyl group containing up to four carbon atoms optionally substituted by one or more chlorine, bromine or fluorine atoms;
  a straight- or branched-chain alkyl group containing up to three carbon atoms which is substituted by —OR$^6$; or
  a group selected from —COR$^7$, —CO$_2$R$^6$, —SR$^9$, —O(CH$_2$)$_m$OR$^6$, —OR$^{61}$, —N(R$^{12}$)SO$_2$R$^8$, —OSO$_2$R$^8$ and —(CR$^{13}$R$^{14}$)$_t$S(O)$_q$R$^8$;
  provided at least one of the groups R$^2$ to R$^4$ represents —(CR$^{13}$R$^{14}$)$_t$—S(O)$_q$R$^8$;

R$^5$ represents the hydrogen atom;

R$^6$, R$^7$, R$^8$ and R$^9$, which may be the same or different, each represents:
  a straight- or branched-chain alkyl group containing up to three carbon atoms;

R$^{61}$ represents:
  a straight- or branched-chain alkyl group containing up to four carbon atoms optionally substituted by one or more chlorine, bromine or fluorine atoms;
  a straight- or branched-chain alkenyl or alkynyl group containing three or four carbon atoms; or
  a cyclopropyl group;

R$^{12}$ represents:
  the hydrogen atom; or
  a straight- or branched-chain alkyl group containing up to three carbon atoms optionally substituted by one or more chlorine, bromine or fluorine atoms;
  an allyl group optionally substituted by one or more chlorine, bromine or fluorine atoms;

R$^{13}$ and R$^{14}$, which may be the same or different, each represents the hydrogen atom, or a methyl or ethyl group;
m represents two or three;
q represents zero, one or two; and
t represents one.

In a third embodiment the invention provides 2-cyano-1,3-dione derivatives of formula (I) wherein:

R represents:
  a straight- or branched-chain alkyl group containing up to six carbon atoms which is optionally substituted by one or more halogen atoms; or
  a cycloalkyl group containing from three to six carbon atoms optionally substituted by one or more R$^7$ groups;

R$^1$ represents the hydrogen atom;

R$^2$, R$^3$, R$^4$ and R$^5$, which may be the same or different, each represents:
  the hydrogen atom;
  a halogen atom;
  a straight- or branched-chain alkyl, alkenyl or alkynyl group containing up to six carbon atoms optionally substituted by one or more halogen atoms;
  a straight- or branched-chain alkyl group containing up to six carbon atoms which is substituted by a group —OR$^6$;
  a group selected from nitro, cyano, —CO$_2$R$^6$, —COR$^7$, —S(O)$_n$R$^9$, —O(CH$_2$)$_m$OR$^6$, —CONR$^{10}$R$^{15}$ and —OR$^{61}$;

$R^6$ represents a straight- or branched-chain alkyl, alkenyl or alkynyl group containing up to six carbon atoms optionally substituted by one or more halogen atoms; or a cycloalkyl group containing from three to six carbon atoms;

$R^{61}$ represents:
a straight- or branched-chain alkyl, alkenyl or alkynyl group containing up to six carbon atoms optionally substituted by one or more halogen atoms; or
a cycloalkyl group containing from three to six carbon atoms;

$R^7$ represents a straight- or branched-chain alkyl group containing up to six carbon atoms optionally substituted by one or more halogen atoms; or
a cycloalkyl group containing from three to six carbon atoms;

$R^9$ represents:
a straight- or branched-chain alkyl, alkenyl or alkynyl group containing up to six carbon atoms optionally substituted by one or more halogen atoms;
a cycloalkyl group containing from three to six carbon atoms;
or phenyl optionally substituted by from one to five groups $R^{21}$ which may be the same or different;

$R^{10}$ represents hydrogen or a straight- or branched-chain alkyl group containing up to six carbon atoms optionally substituted by one or more halogen atoms;

$R^{15}$ represents a group selected from $R^7$ and $—OR^{17}$; where $R^{10}$ and $R^{15}$ are part of a group $—CONR^{10}R^{15}$ they may, together with the nitrogen to which they are attached, form a 5 or 6 membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{17}$ represents a straight- or branched-chain alkyl group containing up to six carbon atoms;

$R^{21}$ represents
a halogen atom;
a straight- or branched-chain alkyl group containing up to three carbon atoms optionally substituted by one or more halogen atoms;
or a group selected from nitro, cyano, $—S(O)_nR^7$ and $—OR^7$;

m represents one, two or three;
n represents zero, one or two;
provided that at least one of the groups $R^2$ to $R^4$ represents $—S(O)_nR^9$ wherein $R^9$ represents phenyl optionally substituted by from one to five groups $R^{21}$ which may be the same or different.

Within this third embodiment, preferably $R^2$ represents a group $—S(O)_nR^9$.

In this third embodiment a preferred class of compounds of formula (I) are those wherein:

R represents:
a straight- or branched-chain alkyl group containing up to three carbon atoms which is optionally substituted by one or more chlorine, bromine or fluorine atoms; or
a cycloalkyl group containing three or four carbon atoms optionally substituted by one or more methyl groups;

$R^2$ represents $—S(O)_nR^9$ or a straight- or branched-chain alkyl group containing up to three carbon atoms;

$R^3$ and $R^4$, which may be the same or different, each represents:
a hydrogen, bromine, chlorine or fluorine atom; or
a straight- or branched-chain alkyl group containing up to four carbon atoms optionally substituted by one or more chlorine, bromine or fluorine atoms;
a straight- or branched-chain alkyl group containing up to four carbon atoms which is substituted by the group $—OR^6$ or
a group selected from $—COR^7$, $—CO_2R^6$, $—S(O)_nR^9$, $—O(CH_2)_mOR^6$ and $—OR^{61}$;

$R^5$ represents a hydrogen atom;

$R^6$ and $R^7$, which may be the same or different each represents:
a straight- or branched-chain alkyl group containing up to three carbon atoms optionally substituted by one or more chlorine, bromine or fluorine atoms; or
a cyclopropyl group;

$R^{61}$ represents:
a straight- or branched-chain alkyl or alkenyl group containing up to four carbon atoms which are optionally substituted by one or more chlorine, bromine, or fluorine atoms;
a straight or branched chain alkynyl group containing three or four carbon atoms; or
a cycloalkyl group containing three or four carbon atoms;

$R^9$ represents:
phenyl optionally substituted by one to three groups $R^{21}$ which may be the same or different;
a straight- or branched-chain alkyl group containing up to three carbon atoms optionally substituted by one or more chlorine bromine or fluorine atoms; or
a cycloalkyl group containing three or four carbon atoms;

$R^{21}$ represents:
a chlorine, bromine or fluorine atom; or
a straight- or branched-chain alkyl group containing up to three carbon atoms which is optionally substituted by one or more chlorine, bromine, or fluorine atoms; or
a group selected from nitro, cyano or $—OR^7$;

m represents two or three; and
n represents zero, one or two;
provided that at least one of $R^2$, $R^3$ or $R^4$ represents the group $—S(O)_nR^9$ wherein $R^9$ represents phenyl optionally substituted by from one to three groups $R^{21}$ and where $R^2$ is not $—S(O)_nR^9$ wherein $R^9$ represents phenyl optionally substituted by from one to three groups $R^{21}$, $R^2$ represents a straight- or branched-chain alkyl group containing up to three carbon atoms, or a group $—S(O)_nR^9$ wherein $R^9$ represents an alkyl group containing up to three carbon atoms.

A further preferred class of compounds within this third embodiment are those wherein:

R represents:
a methyl, ethyl, isopropyl, cyclopropyl or 1-methylcyclopropyl group;

$R^2$ represents $—S(O)_nR^9$ or a straight- or branched-chain alkyl group containing up to three carbon atoms;

$R^3$ and $R^4$ which may be the same or different each represents:
a hydrogen, chlorine, bromine or fluorine atom;
a straight- or branched-chain alkyl group containing up to four carbon atoms; or
a group selected from $—COR^7$, $—CO_2R^6$, $—S(O)_nR^9$ and $—OR^{61}$;

$R^5$ represents the hydrogen atom;
$R^6$ and $R^7$, which may be the same or different, each represents:
  a straight- or branched-chain alkyl group containing up to three carbon atoms; or
  a cyclopropyl group;
$R^{61}$ represents:
  a straight- or branched-chain alkyl group containing up to four carbon atoms optionally substituted by one or more chlorine, bromine or fluorine atoms; or
  a straight- or branched-chain alkenyl or alkynyl group containing three or four carbon atoms; or
  a cyclopropyl group;
$R^9$ represents:
  phenyl optionally substituted by from one to three groups $R^{21}$ which may be the same or different;
  a straight- or branched-chain alkyl group containing up to three carbon atoms optionally substituted by one or more chlorine, bromine or fluorine atoms;
$R^{21}$ represents:
  a chlorine, bromine or fluorine atom, or
  a methyl, methoxy, trifluoromethyl, trifluoromethoxy, nitro or cyano group;
  n represents zero, one or two;
  provided that at least one of $R^2$, $R^3$ or $R^4$ represents the group $—S(O)_nR^9$ wherein $R^9$ represents phenyl optionally substituted by from one to three groups $R^{21}$ and where $R^2$ is not $—S(O)_nR^9$ wherein $R^9$ represents phenyl optionally substituted by from one to three groups $R^{21}$, $R^2$ represents a straight- or branched-chain alkyl group containing up to three carbon atoms, or a group $—S(O)_nR^9$ wherein $R^9$ represents a straight- or branched-chain alkyl group containing up to three carbon atoms.

In a fourth embodiment the invention provides 2-cyano-1,3-dione derivatives of formula (I) wherein:
R represents:
  a straight- or branched-chain alkyl group containing up to six carbon atoms which is optionally substituted by one or more halogen atoms; or
  a cycloalkyl group containing from three to six carbon atoms optionally substituted by one or more $R^7$ groups;
$R^1$ represents the hydrogen atom;
$R^2$, $R^3$, $R^4$ and $R^5$, which may be the same or different, each represents:
  the hydrogen atom;
  a halogen atom;
  a straight- or branched-chain alkyl, alkenyl or alkynyl group containing up to six carbon atoms optionally substituted by one or more halogen atoms;
  a straight- or branched-chain alkyl group containing up to six carbon atoms which is substituted by a group $—OR^6$;
  a group selected from nitro, cyano, $—CO_2R^6$, $—COR^7$, $—S(O)_nR^9$, $—O(CH_2)_mOR^6$, $—CONR^{10}R^{15}$ and $—OR^{61}$;
$R^6$ represents a straight- or branched-chain alkyl, alkenyl or alkynyl group containing up to six carbon atoms optionally substituted by one or more halogen atoms; or
  a cycloalkyl group containing from three to six carbon atoms;
$R^{61}$ represents:
  a straight- or branched-chain alkyl, alkenyl or alkynyl group containing up to six carbon atoms optionally substituted by one or more halogen atoms;
  a cycloalkyl group containing from three to six carbon atoms;
  or phenyl optionally substituted by from one to five groups $R^{21}$ which may be the same or different;
$R^7$ represents a straight- or branched-chain alkyl group containing up to six carbon atoms optionally substituted by one or more halogen atoms; or
  a cycloalkyl group containing from three to six carbon atoms;
$R^9$ represents:
  a straight- or branched-chain alkyl, alkenyl or alkynyl group containing up to six carbon atoms optionally substituted by one or more halogen atoms;
  a cycloalkyl group containing from three to six carbon atoms;
  or phenyl optionally substituted by from one to five groups $R^{21}$ which may be the same or different;
$R^{10}$ represents hydrogen or a straight- or branched-chain alkyl group containing up to six carbon atoms optionally substituted by one or more halogen atoms;
$R^{15}$ represents a group selected from $R^7$ and $—OR^{17}$;
  where $R^{10}$ and $R^{15}$ are part of a group $—CONR^{10}R^{15}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;
$R^{17}$ represents a straight- or branched-chain alkyl group containing up to six carbon atoms;
$R^{21}$ represents:
  a halogen atom;
  a straight- or branched-chain alkyl group containing up to three carbon atoms optionally substituted by one or more halogen atoms;
  or a group selected from nitro, cyano, $—S(O)_nR^7$ and $—OR^7$;
  m represents one, two or three;
  n represents zero, one or two;
  provided that at least one of the groups $R^2$, $R^3$ and $R^4$ represents $—S(O)_nR^9$ wherein $R^9$ represents a group other than optionally substituted phenyl; and at least one of the groups $R^2$ to $R^5$ represents $—OR^{61}$ wherein $R^{61}$ represents phenyl optionally substituted by from one to five groups $R^{21}$ which may be the same or different.

In this fourth embodiment preferably $R^2$ represents $—OR^{61}$, wherein $R^{61}$ represents phenyl optionally substituted by from one to five groups $R^{21}$; or $—S(O)_nR^9$, wherein $R^9$ represents a group other than optionally substituted phenyl.

In this fourth embodiment a preferred class of compounds of formula (I) are those wherein:
R represents:
  a straight- or branched-chain alkyl group containing up to three carbon atoms optionally substituted by one or more chlorine, bromine or fluorine atoms;
  a cycloalkyl group containing three or four carbon atoms optionally substituted by one or more methyl groups;
$R^2$ represents:
  a straight- or branched chain alkyl, alkenyl or alkynyl group containing up to four carbon atoms;
  or a group selected from $—S(O)_nR^9$ and $—OR^{61}$;
$R^3$ and $R^4$, which may be the same or different, each represents:

a hydrogen, chlorine, bromine, or fluorine atom; or
a straight- or branched-chain alkyl, alkenyl or alkynyl group containing up to four carbon atoms optionally substituted by one or more chlorine, bromine or fluorine atoms; or
a group selected from —$COR^7$, —$CO_2R^6$; —$S(O)_nR^9$ and —$OR^{61}$;

$R^5$ represents a hydrogen atom;

$R^6$ and $R^9$, which may be the same or different, each represents:
a straight- or branched-chain alkyl or alkenyl group containing up to four carbon atoms optionally substituted by one or more chlorine, bromine or fluorine atoms; or
a cyclopropyl group;

$R^{61}$ represents:
a straight- or branched-chain alkyl or alkenyl group containing up to four carbon atoms optionally substituted by one or more chlorine, bromine or fluorine atoms;
a straight- or branched chain alkynyl group containing three or four carbon atoms;
a cycloalkyl group containing three or four carbon atoms; or
phenyl optionally substituted by one to three groups $R^{21}$ which may be the same or different;

$R^7$ represents a straight- or branched-chain alkyl group containing up to four carbon atoms optionally substituted by one or more chlorine, fluorine or bromine atoms;
or a cyclopropyl group;

$R^{21}$ represents:
a chlorine, bromine or fluorine atom; or
a straight- or branched-chain alkyl group containing up to three carbon atoms optionally substituted by one or more chlorine, bromine or fluorine atoms; or
a group selected from nitro, cyano and —$OR^7$;

n represents zero, one or two;

provided that at least one of the groups $R^2$, $R^3$ and $R^4$ represents —$S(O)_nR^9$ and at least one of the groups $R^2$ to $R^5$ represents —$OR^{61}$ wherein $R^{61}$ represents phenyl optionally substituted by from one to three groups $R^{21}$ which may be the same or different and when $R^2$ is not —$S(O)_nR^9$ or —$OR^{61}$, $R^2$ represents a straight- or branched-chain alkyl, alkenyl or alkynyl group containing up to four carbon atoms.

A further preferred class of compounds within this fourth embodiment are those wherein:

R represents:
a methyl, ethyl, isopropyl, cyclopropyl or 1-methylcyclopropyl group;

$R^2$ represents:
a straight- or branched-chain alkyl group containing up to three carbon atoms;
or a group selected from —$S(O)_nR^9$ and —$OR^{61}$;

$R^3$ and $R^4$, which may be the same or different, each represents:
a hydrogen, chlorine, bromine or fluorine atom;
a straight- or branched-chain alkyl or alkenyl group containing up to four carbon atoms optionally substituted by one or more chlorine, bromine or fluorine atoms; or
a group selected from —$OR^{61}$, —$S(O)_nR^9$, —$COR^7$ and —$CO_2R^6$;

$R^5$ represents the hydrogen atom;

$R^{61}$ represents:
a straight- or branched-chain alkyl group containing up to three carbon atoms optionally substituted by one or more chlorine, bromine or fluorine atoms;
a cyclopropyl group; or
phenyl optionally substituted by from one to three groups $R^{21}$ which may be the same or different;

$R^6$, $R^7$ and $R^9$, which may be the same or different, each represents:
a straight- or branched-chain alkyl group containing up to three carbon atoms; or
a cyclopropyl group;

$R^{21}$ represents:
a chlorine, bromine or fluorine atom; or
a group selected from methyl, methoxy, trifluoromethyl, trifluoromethoxy, cyano or nitro; and n represents zero, one or two;

provided that at least one of the groups $R^2$, $R^3$ and $R^4$ represents —$S(O)_nR^9$ and at least one of the groups $R^2$ to $R^5$ represents —$OR^{61}$ wherein $R^{61}$ represents phenyl optionally substituted by from one to three groups $R^{21}$ which may be the same or different and when $R^2$ is not —$S(O)_nR^9$ or —$OR^{61}$, $R^2$ represents a straight- or branched-chain alkyl group containing up to three carbon atoms.

In a fifth embodiment the invention provides 2-cyano-1,3-dione derivatives of formula (I) wherein:

R represents:
a straight- or branched-chain alkyl group containing up to six carbon atoms which is optionally substituted by one or more halogen atoms;
a cycloalkyl group containing from three to six carbon atoms optionally substituted by one or more $R^7$ groups;

$R^1$ represents the hydrogen atom;

$R^2$, $R^3$, $R^4$ and $R^5$, which may be the same or different, each represents:
the hydrogen atom;
a halogen atom;
a straight- or branched-chain alkyl, alkenyl or alkynyl group containing up to six carbon atoms optionally substituted by one or more halogen atoms;
a straight- or branched-chain alkyl group containing up to six carbon atoms which is substituted by a group —$OR^6$;
a group selected from nitro, cyano, —$CO_2R^6$, —$COR^7$, —$S(O)_nR^9$, —$O(CH_2)_mOR^6$, —$CONR^{10}R^{15}$ and —$OR^{61}$;

$R^6$ represents a straight- or branched-chain alkyl, alkenyl or alkynyl group containing up to six carbon atoms optionally substituted by one or more halogen atoms; or
a cycloalkyl group containing from three to six carbon atoms;

$R^{61}$ represents:
a straight- or branched-chain alkyl, alkenyl or alkynyl group containing up to six carbon atoms optionally substituted by one or more halogen atoms; or
a cycloalkyl group containing from three to six carbon atoms;

$R^7$ represents a straight- or branched-chain alkyl group containing up to six carbon atoms optionally substituted by one or more halogen atoms; or
a cycloalkyl group containing from three to six carbon atoms;

$R^9$ represents:
a straight- or branched-chain alkyl, alkenyl or alkynyl group containing up to six carbon atoms optionally substituted by one or more halogen atoms; or a cycloalkyl group containing from three to six carbon
  atoms;
$R^{10}$ represents hydrogen or a straight- or branched-chain
  alkyl group containing up to six carbon atoms option-
  ally substituted by one or more halogen atoms;
$R^{15}$ represents a group selected from $R^7$ and —$OR^{17}$;
  where $R^{10}$ and $R^{15}$ are part of a group —$CONR^{10}R^{15}$
  they may, together with the nitrogen to which they
  are attached, form a five or six membered ring
  optionally containing an oxygen or nitrogen atom in
  the ring (e.g. pyrrolidine, morpholine, pyrrole, pip-
  eridine and piperazine), wherein the ring is option-
  ally substituted by one or more alkyl groups con-
  taining up to three carbon atoms;
$R^{17}$ represents a straight- or branched-chain alkyl group
  containing up to six carbon atoms;
$R^{21}$ represents:
  a halogen atom;
  a straight- or branched-chain alkyl group containing up
    to three carbon atoms optionally substituted by one
    or more halogen atoms;
  or a group selected from nitro, cyano, —$S(O)_nR^7$ and
    —$OR^7$;
  m represents one, two or three;
  n represents zero, one or two;
  provided that at least one of the groups $R^2$, $R^3$ and $R^4$
    represents —$S(O)_nR^9$ and at least one of the groups
    $R^2$ to $R^5$ represents —$OR^{61}$ wherein $R^{61}$ represents
    a straight- or branched-chain alkenyl or alkynyl
    group containing from three to six carbon atoms
    optionally substituted by one or more halogen atoms.

In this fifth embodiment a preferred class of compounds
of formula (I) are those wherein:
R represents:
  a straight- or branched-chain alkyl group containing up
    to three carbon atoms which is optionally substituted
    by one or more chlorine, bromine or fluorine atoms;
    or
  a cycloalkyl group containing three or four carbon
    atoms optionally substituted by one or more methyl
    groups;
$R^2$, $R^3$ and $R^4$, which may the same or different, each
  represents:
  a hydrogen, chlorine, bromine or fluorine atom; or
  a straight- or branched-chain alkyl, alkenyl or alkynyl
    group containing up to four carbon atoms optionally
    substituted by one or more chlorine, bromine or
    fluorine atoms;
  a group selected from —$COR^7$, —$S(O)_nR^9$, —$CO_2R^6$
    and —$OR^{61}$;
$R^5$ represents the hydrogen atom;
$R^6$, $R^7$ and $R^9$ which may be the same or different, each
  represents:
  a straight- or branched-chain alkyl group containing up
    to four carbon atoms optionally substituted by one or
    more chlorine, bromine, or fluorine atoms; or
  a cyclopropyl group;
$R^{61}$ represents:
  a straight- or branched-chain alkyl, alkenyl, alkynyl
    group containing up to four carbon atoms optionally
    substituted by one or more chlorine, bromine or
    fluorine atoms; or
  a cycloalkyl group containing three or four carbon
    atoms;
  n represents zero, one or two;
  provided that at least one of the groups $R^2$, $R^3$ and $R^4$
    represents —$S(O)_nR^9$ and at least one of the groups $R^2$, $R^3$ and $R^4$ represents —$OR^{61}$ wherein $R^{61}$ rep-
  resents a straight- or branched-chain alkenyl or alky-
  nyl group containing up to four carbon at optionally
  substituted by one or more chlorine, bromine or
  fluorine atoms.

A further preferred class of compounds of formula (I)
within this fifth embodiment are those wherein:
R represents:
  a methyl, ethyl, isopropyl, cyclopropyl or
    1-methylcyclopropyl group;
$R^2$, $R^3$ and $R^4$, which may be the same or different, each
  represents:
  a hydrogen, chlorine, bromine or fluorine atom;
  a straight- or branched-chain alkyl or alkenyl group
    containing up to four carbon atoms optionally sub-
    stituted by one or more chlorine, bromine or fluorine
    atoms; or
  a group selected from —$S(O)_nR^9$, —$OR^{61}$, —$COR^7$
    and —$CO_2R^6$;
$R^5$ represents the hydrogen atom;
$R^{61}$ represents:
  a straight- or branched-chain alkyl or alkenyl group
    containing up to four carbon atoms optionally sub-
    stituted by one or more chlorine, bromine or fluorine
    atoms;
  a straight- or branched-chain alkynyl group containing
    three or four carbon atoms;
$R^6$, $R^7$ and $R^9$, which may be the same or different, each
  represents:
  a straight- or branched-chain alkyl group containing up
    to three carbon atoms; or
  a cyclopropyl group;
  n represents zero, one or two;
  provided that one of the groups $R^2$, $R^3$ and $R^4$ repre-
    sents —$S(O)_nR^9$ and one of the groups $R^2$, $R^3$ and $R^4$
    represents —$OR^{61}$ wherein $R^{61}$ represents a straight-
    or branched-chain alkenyl group containing up to
    four carbon atoms optionally substituted by one or
    more chlorine, bromine or fluorine atoms; or $R^{61}$
    represents a straight- or branched-chain alkynyl
    group containing three or four carbon atoms.

In a sixth embodiment the invention provides 2-cyano-1,
3-dione derivatives of formula (I) wherein:
R represents:
  a straight- or branched-chain alkyl group containing up
    to six carbon atoms which is optionally substituted
    by one or more halogen atoms; or
  a cycloalkyl group containing from three to six carbon
    atoms optionally substituted by one or more $R^7$
    groups;
$R^1$ represents the hydrogen atom;
$R^2$ represents:
  a straight- or branched-chain alkyl, alkenyl or alkynyl
    group containing up to six carbon atoms;
  or a group selected from —$OSO_2R^8$ and —$S(O)_nR^9$;
$R^3$, $R^4$ and $R^5$, which may be the same or different, each
  represents:
  the hydrogen atom;
  a halogen atom;
  a straight- or branched-chain alkyl, alkenyl or alkynyl
    group containing up to six carbon atoms optionally
    substituted by one or more halogen atoms;
  a straight- or branched-chain alkyl group containing up
    to six carbon atoms which is substituted by a group
    —$OR^6$;
  a group selected from nitro, cyano, —$CO_2R^6$, —$COR^7$,
    —$S(O)_nR^9$, —$O(CH_2)_mOR^6$, —$N(R^{12})SO_2R^8$,
    —$OR^{61}$, —$CONR^{10}R^{15}$ and —$OSO_2R^8$;

provided that at least one of the groups $R^2$ to $R^5$ represents $-OSO_2R^8$ and where $R^2$ is not $-OSO_2R^8$, $R^2$ represents a group selected from $-S(O)_nR^9$ and a straight- or branched-chain alkyl, alkenyl or alkynyl group containing up to six carbon atoms;

$R^6$ represents a straight- or branched-chain alkyl, alkenyl or alkynyl group containing up to six carbon atoms optionally substituted by one or more halogen atoms; or a cycloalkyl group containing from three to six carbon atoms;

$R^{61}$ represents:
 a straight- or branched-chain alkyl, alkenyl or alkynyl group containing up to six carbon atoms optionally substituted by one or more halogen atoms;
 a cycloalkyl group containing from three to six carbon atoms;
 or phenyl optionally substituted by from one to five groups $R^{21}$ which may be the same or different;

$R^7$ represents a straight- or branched-chain alkyl group containing up to six carbon atoms optionally substituted by one or more halogen atoms; or a cycloalkyl group containing from three to six carbon atoms;

$R^8$ represents:
 a straight- or branched-chain alkyl, alkenyl or alkynyl group containing up to six carbon atoms optionally substituted by one or more halogen atoms;
 a cycloalkyl group containing from three to six carbon atoms;
 phenyl optionally substituted by from one to five groups $R^{21}$ which may be the same or different; or $-NR^{10}R^{11}$;

$R^9$ represents:
 a straight- or branched-chain alkyl, alkenyl or alkynyl group containing up to six carbon atoms optionally substituted by one or more halogen atoms;
 a cycloalkyl group containing from three to six carbon atoms; or phenyl optionally substituted by from one to five groups $R^{21}$ which may be the same or different;

$R^{10}$ represents the hydrogen atom or a straight- or branched-chain alkyl group containing up to six carbon atoms optionally substituted by one or more halogen atoms;

$R^{11}$ represents:
 a straight- or branched-chain alkyl group containing up to six carbon atoms optionally substituted by one or more halogen atoms;
 where $R^{10}$ and $R^{11}$ are part of a group $-NR^{10}R^{11}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{12}$ represents:
 the hydrogen atom;
 a straight- or branched-chain alkyl, alkenyl or alkynyl group containing up to six carbon atoms optionally substituted by one or more halogen atoms;
 a cycloalkyl group containing from three to six carbon atoms;
 or a group $-OR^{17}$;

$R^{15}$ represents a group selected from $R^7$ and $-OR^{17}$;

where $R^{10}$ and $R^{15}$ are part of a group $-CONR^{10}R^{15}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{17}$ represents a straight- or branched-chain alkyl group containing up to six carbon atoms;

$R^{21}$ represents:
 a halogen atom;
 a straight- or branched-chain alkyl group containing up to three carbon atoms optionally substituted by one or more halogen atoms;
 or a group selected from nitro, cyano, $-S(O)_nR^7$ and $-OR^7$;

m represents one, two or three; and
n represents zero, one or two.

In this sixth embodiment preferably $R^2$ represents $-OSO_2R^8$ or $-S(O)_nR^9$.

Also in this sixth embodiment a preferred class of compounds of formula (I) are those wherein:

R represents:
 a straight- or branched-chain alkyl group containing up to six carbon atoms optionally substituted by one or more halogen atoms;
 a cycloalkyl group containing from three to six carbon atoms optionally substituted by one or more methyl groups;

$R^2$ represents:
 a straight- or branched-chain alkyl, alkenyl or alkynyl group containing up to six carbon atoms;
 or a group selected from $-OSO_2R^8$ and $-S(O)_nR^9$;

$R^3$, $R^4$ and $R^5$, which may be the same or different, each represents:
 a hydrogen or halogen atom; or
 a straight- or branched-chain alkyl, alkenyl or alkynyl group containing up to six carbon atoms optionally substituted by one or more halogen atoms;
 a straight- or branched-chain alkyl group containing up to six carbon atoms which is substituted by $-OR^6$; or
 a group selected from $-COR^7$, $-CO_2R^6$, cyano, nitro, $-O(CH_2)_mOR^6$, $-OR^{61}$, $-N(R^{12})SO_2R^8$ $-S(O)_n R^9$ and $-OSO_2R^8$;

$R^6$, $R^7$, $R^9$ and $R^{12}$, which may be the same or different, each represents:
 a straight- or branched-chain alkyl group containing up to six carbon atoms optionally substituted by one or more halogen atoms;
 or a cycloalkyl group containing three or four carbon atoms;

$R^{61}$ represents:
 a straight- or branched-chain alkyl or alkenyl group containing up to six carbon atoms optionally substituted by one or more halogen atoms;
 a straight- or branched-chain alkynyl group containing from three to six carbon atoms; or
 a cycloalkyl group containing from three to six carbon atoms;

$R^8$ represents:
 a straight- or branched-chain alkyl group containing up to four carbon atoms optionally substituted by one or more halogen atoms;
 a cycloalkyl group containing three or four carbon atoms; or phenyl optionally substituted by from one to three groups $R^{21}$ which may be the same or different;

$R^{21}$ represents:
a halogen atom; or
a straight- or branched-chain alkyl group containing up to three carbon atoms optionally substituted by one or more halogen atoms; or
a group selected from nitro, cyano, $-S(O)_nR^9$ and $-OR^7$;

m represents two or three; and n represents zero, one or two.

A further preferred class of compounds of formula (I) within this sixth embodiment are those wherein:

R represents:
a straight- or branched-chain alkyl group containing up to three carbon atoms;
a cycloalkyl group containing three or four carbon atoms optionally substituted by one or more methyl groups;

$R^2$ represents:
a straight- or branched-chain alkyl, alkenyl or alkynyl group containing up to four carbon atoms;
or a group selected from $-OSO_2R^8$ and $-S(O)_nR^9$;

$R^3$, $R^4$ and $R^5$, which may be the same or different, each represents:
a hydrogen, chlorine, bromine or fluorine atom; or
a straight- or branched-chain alkyl, alkenyl or alkynyl group containing up to four carbon atoms optionally substituted by one or more chlorine, bromine or fluorine atoms; or
a group selected from $-CO_2R^6$, $-COR^7$, $-S(O)_nR^9$, $-OR^{61}$, $-N(R^{12})SO_2R^8$, and $-OSO_2R^8$;

$R^6$, $R^7$, $R^9$ and $R^{12}$, which may be the same or different, each represents:
a straight- or branched-chain alkyl group containing up to three carbon atoms optionally substituted by one or more chlorine, bromine or fluorine atoms; or
a cyclopropyl group;

$R^{61}$ represents:
a straight- or branched-chain alkyl or alkenyl group containing up to four carbon atoms optionally substituted by one or more chlorine, bromine, or fluorine atoms;
a straight- or branched-chain alkynyl group containing three or four carbon atoms; or
a cycloalkyl group containing three or four carbon atoms;

$R^8$ represents:
a straight- or branched-chain alkyl group containing up to three carbon atoms; or
a cycloalkyl group containing three or four carbon atoms;
a phenyl ring optionally substituted by from one to three groups $R^{21}$ which may be the same or different;

$R^{21}$ represents:
a chlorine, bromine or fluorine atom, or a group selected from nitro, cyano, methyl, methoxy, trifluoromethyl and trifluoromethoxy;
n represents zero, one or two.

A further preferred class of compounds within this sixth embodiment are those wherein:

R represents:
a methyl, ethyl, isopropyl, cyclopropyl or 1-methylcyclopropyl group.

$R^2$ represents:

a straight- or branched-chain alkyl, alkenyl or alkynyl group containing up to four carbon atoms;
or a group selected from $-OSO_2R^8$ and $-S(O)_nR^9$;

$R^3$, $R^4$ and $R^5$, which may be the same or different, each represents:
a hydrogen, chlorine, bromine or fluorine atom;
a straight- or branched-chain alkyl or alkenyl group containing up to four carbon atoms optionally substituted by one or more chlorine, bromine or fluorine atoms; or
a group selected from $-S(O)_nR^9$, $-OR^{61}$, $-COR^7$, $-CO_2R^6$ and $-OSO_2R^8$;

$R^{61}$ represents:
a straight- or branched-chain alkyl group containing up to three carbon atoms optionally substituted by one or more chlorine, bromine or fluorine groups;
a straight- or branched-chain alkenyl or alkynyl containing three or four carbon atoms; or
a cyclopropyl group;

$R^6$, $R^7$, $R^8$ and $R^9$, which may be the same or different, each represents:
a straight- or branched chain alkyl group containing up to three carbon atoms; or
a cyclopropyl group; and
n represents zero, one or two.

In a seventh embodiment the invention provides 2-cyano-1,3-dione derivatives of formula (I) wherein:

R represents:
a straight- or branched-chain alkyl group containing up to six carbon atoms which is optionally substituted by one or more halogen atoms; or
a cycloalkyl group containing from three to six carbon atoms optionally substituted by one or more $R^7$ groups;

$R^1$ represents the hydrogen atom;

$R^2$, $R^3$, $R^4$ and $R^5$, which may be the same or different, each represents:
the hydrogen atom;
a halogen atom;
a straight- or branched-chain alkyl, alkenyl or alkynyl group containing up to six carbon atoms optionally substituted by one or more halogen atoms;
a straight- or branched-chain alkyl group containing up to six carbon atoms which is substituted by a group $-OR^6$;
a group selected from nitro, cyano, $-CO_2R^6$, $-COR^7$, $-S(O)_nR^9$, $-O(CH_2)_mOR^6$, $-CONR^{10}R^{15}$ and $-OR^{61}$;

$R^6$ represents a straight- or branched-chain alkyl, alkenyl or alkynyl group containing up to six carbon atoms optionally substituted by one or more halogen atoms; or
a cycloalkyl group containing three or four carbon atoms;

$R^{61}$ represents:
a straight- or branched-chain alkyl, alkenyl or alkynyl group containing up to six carbon atoms optionally substituted by one or more halogen atoms; or
a cycloalkyl group containing three or four carbon atoms;

$R^7$ represents a straight- or branched-chain alkyl group containing up to six carbon atoms optionally substituted by one or more halogen atoms; or
a cycloalkyl group containing three or four carbon atoms;

$R^9$ represents:

a straight- or branched-chain alkyl, alkenyl or alkynyl group containing up to six carbon atoms optionally substituted by one or more halogen atoms;
a cycloalkyl group containing three or four carbon atoms; or
phenyl optionally substituted by from one to five groups $R^{21}$ which may be the same or different;

$R^{10}$ represents hydrogen or a straight- or branched-chain alkyl group containing up to six carbon atoms optionally substituted by one or more halogen atoms;

$R^{15}$ represents a group selected from $R^7$ and —$OR^{17}$;
where $R^{10}$ and $R^{15}$ are part of a group —$CONR^{10}R^{15}$ they may, together with the nitrogen to which they are attached, form a five or six membered ring optionally containing an oxygen or nitrogen atom in the ring (e.g. pyrrolidine, morpholine, pyrrole, piperidine and piperazine), wherein the ring is optionally substituted by one or more alkyl groups containing up to three carbon atoms;

$R^{17}$ represents a straight- or branched-chain alkyl group containing up to six carbon atoms;

$R^{21}$ represents
a halogen atom;
a straight- or branched-chain alkyl group containing up to three carbon atoms optionally substituted by one or more halogen atoms;
or a group selected from nitro, cyano, —$S(O)_nR^7$ and —$OR^7$;

m represents one, two or three;
n represents zero, one or two;
provided that:
at least one of the groups $R^2$, $R^3$ and $R^4$ represents —$S(O)_nR^9$ wherein $R^9$ represents a straight- or branched-chain alkyl, alkenyl or alkynyl group containing up to six carbon atoms optionally substituted by one or more halogen atoms; and
at least one of the groups $R^2$ to $R^5$ represents a straight- or branched chain alkenyl or alkynyl group containing up to six carbon atoms optionally substituted by one or more halogen atoms.

In this seventh embodiment a preferred class of compounds of formula (I) are those wherein:

R represents:
a straight- or branched-chain alkyl group containing up to three carbon atoms optionally substituted by one or more chlorine, bromine or fluorine atoms; or
a cycloalkyl group containing three or four carbon atoms optionally substituted by one or more methyl groups;

$R^2$, $R^3$ and $R^4$, which may be the same or different, each represents:
a hydrogen, chlorine, bromine or fluorine atom; or
a straight- or branched-chain alkyl, alkenyl or alkynyl group containing up to four carbons optionally substituted by one or more chlorine, bromine or fluorine atoms;
a straight- or branched-chain alkyl group containing up to four carbon atoms which is substituted by —$OR^6$;
a group selected from —$COR^7$, —$CO_2R^6$, —$S(O)_nR^9$, —$O(CH_2)_mOR^6$ and —$OR^{61}$;

$R^5$ represents the hydrogen atom;

$R^6$ and $R^7$, which may be the same or different, each represents:
a straight- or branched-chain alkyl group containing up to four carbon atoms optionally substituted by one or more chlorine, bromine or fluorine atoms; or
a cyclopropyl group;

$R^{61}$ represents:
a straight- or branched-chain alkyl or alkenyl group containing up to four carbon atoms optionally substituted by one or more chlorine, bromine or fluorine atoms;
a straight- or branched-chain alkynyl group containing three or four carbon atoms; or
a cycloalkyl group containing three or four carbon atoms;

$R^9$ represents:
a straight- or branched-chain alkyl, alkenyl or alkynyl group containing up to four carbon atoms optionally substituted by one or more chlorine, bromine or fluorine atoms;
a cycloalkyl group containing three or four carbon atoms; or
phenyl optionally substituted by from one to three groups $R^{21}$ which may be the same or different;

$R^{21}$ represents:
a chlorine, bromine or fluorine atom;
a straight- or branched-chain alkyl group containing up to three carbon atoms optionally substituted by one or more chlorine, bromine or fluorine atoms; or
a group selected from nitro, cyano and —$OR^7$;

m represents two or three;
n represents zero, one or two;
provided that:
at least one of the groups $R^2$, $R^3$ and $R^4$ represents —$S(O)_nR^9$; and
at least one of the groups $R^2$, $R^3$ and $R^4$ represents a straight- or branched-chain alkenyl or alkynyl group containing up to four carbon atoms optionally substituted by one or more chlorine, bromine or fluorine atoms.

A further preferred class of compounds of formula (I) within this seventh embodiment are those wherein R represents:
a methyl, ethyl, isopropyl, cyclopropyl or 1-methylcyclopropyl group;

$R^2$, $R^3$ and $R^4$, which may be the same or different, each represents:
a hydrogen, chlorine, bromine or fluorine atom, or
a straight- or branched-chain alkyl, alkenyl or alkynyl group containing up to four carbon atoms optionally substituted by one or more chlorine, bromine or fluorine atoms;
a group selected from —$COR^7$, —$CO_2R^6$, —$S(O)_nR^9$, and —$OR^{61}$;

$R^5$ represents: the hydrogen atom;

$R^6$ and $R^7$, which may be the same or different, each represents:
a straight- or branched-chain alkyl group containing up to three carbon atoms; or
a cyclopropyl group;

$R^{61}$ represents:
a straight- or branched-chain alkyl or alkenyl group containing up to four carbon atoms optionally substituted by one or more chlorine, bromine or fluorine groups;
a straight- or branched-chain alkynyl group containing three or four carbon atoms; or
a cyclopropyl group;

$R^9$ represents:
a straight- or branched-chain alkyl group containing up to three carbon atoms; or a cyclopropyl group;

n represents zero, one or two;

provided that:

at least one of the groups $R^2$, $R^3$ and $R^4$ represents —$S(O)_nR^9$; and at least one of the groups $R^2$, $R^3$ and $R^4$ represents an alkenyl or alkynyl group containing up to four carbon atoms optionally substituted by one or more chlorine, bromine or fluorine atoms.

In an eighth embodiment the invention provides compounds of formula (I) wherein:

R represents:

straight- or branched-chain alkyl having from 1 to 6 carbon atoms, optionally substituted by one or more halogen atoms which may be the same or different; or cycloalkyl having from 3 to 6 carbon atoms, optionally bearing one or more substituents which may be the same or different selected from the group consisting of $R^{51}$ and halogen;

$R^1$ represents hydrogen;

$R^2$ and $R^4$, which may be the same or different, each represents:

a halogen atom or hydrogen atom, or straight- or branched-chain alkyl having from 1 to 6 carbon atoms, bearing a substituent —$OR^{51}$; or a member selected from the group consisting of $R^{51}$, nitro, cyano, —$S(O)_nR^{41}$, —$OR^{51}$, —$O(CH_2)_mOR^{51}$ and —$CO_2R^{51}$;

$R^3$ represents:

a halogen or hydrogen atom, or straight- or branched-chain alkyl having from 1 to 6 carbon atoms, bearing a substituent —$OR^{51}$; or a member selected from the group consisting of —$S(O)_nR^{41}$, $R^{51}$, nitro, cyano, —$OR^{51}$, —$O(CH_2)_mOR^{51}$ and —$CO_2R^{51}$;

provided that at least one of the groups $R^2$, $R^3$ and $R^4$ represents —$S(O)_nR^{41}$;

$R^5$ represents:

a halogen or hydrogen atom, or straight- or branched-chain alkyl having from 1 to 6 carbon atoms, bearing a substituent —$OR^{51}$; or a member selected from the group consisting of $R^{51}$, nitro, cyano, —$OR^{51}$, —$O(CH_2)_mOR^{51}$ and —$CO_2R^{51}$;

$R^{41}$ and $R^{51}$, which may be the same or different, each represents:

straight- or branched-chain alkyl having from 1 to 6 carbon atoms, optionally substituted by one or more halogen atoms which may be the same or different;

m is an integer from 1 to 3; and n is zero, 1 or 2;

metal complexes thereof, and agriculturally acceptable salts thereof, which possess valuable herbicidal properties.

Compounds of formula I may exist in enolic tautomeric forms that may give rise to geometric isomers around the enolic double bond.

Furthermore, in certain cases the substituents R, $R^1$, $R^2$, $R^3$, $R^4$, $R^5$, $R^{41}$ and $R^{51}$ may contribute to optical isomerism and/or stereoisomerism. All such forms are embraced by the present invention.

By the term "agriculturally acceptable salts" is meant salts the cations of which are known and accepted in the art for the formation of salts for agricultural or horticultural use. Preferably the salts are water soluble.

By the term "metal complexes" is meant compounds in which one or both of the oxygen atoms of the 1,3-dione act as chelating agents to a metal cation. Examples of such cations include zinc, manganese, cupric, cuprous, ferric, ferrous, titanium and aluminium.

Suitable salts formed by compounds of formula I which are acidic, i.e. in enolic tautomeric forms, with bases include alkali metal (e.g. sodium and potassium salts), alkaline earth metal (e.g. calcium and magnesium) salts, ammonium (e.g. dioctylmethylamine and morpholine) salts.

The compounds of this invention represent in some aspects of their activity, for example their control of important weed species such as *Setaria viridis, Setaria faberii, Echinochloa crus-galli, Avena fatua* and *Alopecurus myosuroides*, an improvement over known compounds.

In this eighth embodiment compounds of formula I wherein R is ethyl, methyl, n-propyl, isopropyl, t-butyl, cyclopropyl or 1-methylcyclopropyl are preferred (particularly where R is methyl, 1-methylcyclopropyl or, most preferably, cyclopropyl).

Also in this eighth embodiment compounds of formula I wherein $R^{41}$ is straight- or branched-chain alkyl having from 1 to 6 carbon atoms are also preferred (especially ethyl, n-propyl, sec-butyl or, most preferably, methyl).

Compounds of formula I wherein $R^5$ is hydrogen constitute a further preferred class within this eighth embodiment.

Compounds of formula I wherein $R^4$ is hydrogen, —$S(O)_nR^{41}$, halogen or —$OR^{51}$ are also preferred within this eighth embodiment (particularly hydrogen or halogen).

In one aspect of this eighth embodiment the invention is provides compounds of formula I wherein:

R represents:

straight- or branched-chain alkyl having from 1 to 6 carbon atoms, optionally substituted by one or more halogen atoms which may be the same or different; or cycloalkyl having from 3 to 6 carbon atoms, optionally bearing one or more substituents which may be the same or different selected from the group consisting of $R^{51}$ and halogen;

$R^1$ represents hydrogen;

$R^2$ represents —$S(O)_nR^{41}$;

$R^3$ and $R^5$, which may be the same or different, each represents:

a halogen or hydrogen atom, or straight- or branched-chain alkyl having from 1 to 6 carbon atoms, bearing a substituent —$OR^{51}$; or a member selected from the group consisting of $R^{51}$, nitro, cyano, —$OR^{51}$, —$O(CH_2)_mOR^{51}$ and —$CO_2R^{51}$;

provided that at least one of $R^3$ and $R^5$ is hydrogen;

$R^4$ represents:

a halogen atom or hydrogen atom, or straight- or branched-chain alkyl having from 1 to 6 carbon atoms which is substituted by —$OR^{51}$; or a member selected from the group consisting of $R^{51}$, nitro, cyano, —$SR^{41}$, —$OR^{51}$, —$O(CH_2)_mOR^{51}$, or —$CO_2R^{51}$;

$R^{41}$ and $R^{51}$, which may be the same or different, each represents:

straight- or branched-chain alkyl having from 1 to 6 carbon atoms, optionally substituted by one or more halogen atoms which may be the same or different;

m is an integer from 1 to 3; and n is zero, 1 or 2;

with the proviso that when n is zero, $R^4$ does not represent —$SR^{41}$;

and enolic tautomeric forms thereof.

In this first aspect, a preferred class of compounds of formula I (because of their herbicidal properties) are those wherein the structural variables are selected such that they meet one or more definitions selected from the group consisting of:

(a) R represents for example methyl, isopropyl, t-butyl, cyclopropyl or 1-methylcyclopropyl; and/or (b) $R^4$ represents:
a halogen atom or hydrogen atom, or
a member selected from the group consisting of —$OR^{51}$, for example methoxy, ethoxy or trifluoromethoxy, or $R^{51}$, for example methyl or trifluoromethyl, or nitro; and/or (c) $R^3$ and $R^5$, which may be the same or different, each represents:
a halogen atom or hydrogen atom,
straight- or branched-chain alkyl having from 1 to 6 carbon atoms, bearing a substituent —$OR^{51}$, for example methoxymethyl; or
a member selected from the group consisting of $R^{51}$, for example methyl or trifluoromethyl, —$OR^{51}$, for example methoxy, ethoxy or isopropoxy, —$O(CH_2)_m OR^{51}$ where m is 2 or 3, for example 2-ethoxyethoxy or 2-methoxyethoxy,
or —$CO_2R^{51}$, for example carbomethoxy, carboethoxy, or carboisopropoxy,
provided that at least one of $R^3$ and $R^5$ represent hydrogen; and/or (d) $R^{41}$ represents:
straight- or branched-chain alkyl having from 1 to 4 carbon atoms, optionally substituted by one or more halogen atoms, which may be same or different, for example isopropyl, methyl or ethyl; and/or (e) $R^{51}$ represents:
straight- or branched-chain alkyl having from 1 to 4 carbon atoms, optionally substituted by one or more halogen atoms, which may be the same or different, for example methyl, ethyl, isopropyl, or trifluoromethyl; and (f) 'halogen' represents chlorine, bromine or fluorine.

A further preferred class of compounds of formula I within this first aspect are those in which $R^5$ represents a hydrogen atom.

A further preferred class of compounds of formula I within this first aspect are those wherein:

R represents isopropyl, cyclopropyl or 1-methylcyclopropyl;

$R^3$ represents hydrogen, alkoxy or halogen, most preferably hydrogen;

$R^4$ represents hydrogen, chlorine, bromine, trifluoromethyl, methoxy or methyl;

$R^5$ represents hydrogen;

$R^{41}$ represents methyl, ethyl or isopropyl;

and n is zero, one or two, most preferably zero or two.

In a second aspect of this eighth embodiment the invention provides compounds of formula I wherein:

R represents:
straight- or branched-chain alkyl having from 1 to 6 carbon atoms, optionally substituted by one or more halogen atoms which may be the same or different; or
cycloalkyl having from 3 to 6 carbon atoms, optionally bearing one or more substituents which may be the same or different selected from the group consisting of $R^{51}$ and halogen;

$R^1$ represents hydrogen;

$R^2$ represents:
a halogen atom, or
straight- or branched-chain alkyl having from 1 to 6 carbon atoms, bearing a substituent —$OR^{51}$; or
a member selected from the group consisting of $R^{51}$, cyano, —$SR^{41}$, —$OR^{51}$, —$O(CH_2)_m OR^{51}$, and —$CO_2R^{51}$;

$R^3$ and $R^5$, which may be the same or different, each represents:
a halogen or hydrogen atom, or
straight- or branched-chain alkyl having from 1 to 6 carbon atoms, bearing a substituent —$OR^{51}$; or
a member selected from the group consisting of $R^{51}$, nitro, cyano, —$OR^{51}$, —$O(CH_2)_m OR^{51}$ and —$CO_2R^{51}$;
provided that at least one of $R^3$ and $R^5$ is hydrogen;

$R^4$ represents —$S(O)_n R^{41}$;

$R^{41}$ and $R^{51}$, which may be the same or different, each represents:
straight- or branched-chain alkyl having from 1 to 6 carbon atoms, optionally substituted by one or more halogen atoms which may be the same or different;
n is zero, 1 or 2; m is an integer from 1 to 3;
and enolic tautomeric forms thereof.

In this second aspect, particularly important classes of compounds of formula I because of their herbicidal properties are those wherein the structural variables are selected such that they meet one or more definitions selected from the group consisting of:

(a) R represents for example ethyl, methyl, n-propyl, isopropyl, t-butyl, cyclopropyl or 1-methylcyclopropyl; and/or (b) $R^2$ represents:
a halogen atom; or
a member selected from the group consisting of —$OR^{51}$, for example methoxy, ethoxy or trifluoromethoxy; or
$R^{51}$, for example methyl or trifluoromethyl; and/or (c) $R^3$ and $R^5$, which may be the same or different, each represents:
a halogen or hydrogen atom; or
straight- or branched-chain alkyl having from 1 to 6 carbon atoms, bearing a substituent —$OR^{51}$, for example methoxymethyl; or
a member selected from the group consisting of $R^{51}$, for example methyl, or trifluoromethyl; or —$OR^{51}$, for example methoxy, ethoxy or isopropoxy, —$O(CH_2)_m OR^{51}$ where m is 2 or 3, for example 2-ethoxyethoxy or 2-methoxyethoxy,
or —$CO_2R^{51}$, for example carboethoxy, carbomethoxy, or carboisopropoxy,
provided that at least one of $R^3$ and $R^5$ is hydrogen; and/or (d) $R^{41}$ represents:
straight- or branched-chain alkyl having from 1 to 4 carbon atoms, optionally substituted by one or more halogen atoms which may be the same or different, for example methyl, ethyl or trifluoromethyl; and/or (e) $R^{51}$ represents:
straight- or branched-chain alkyl having from 1 to 4 carbon atoms, optionally substituted by one or more halogen atoms which may be the same or different, for example methyl, isopropyl, or trifluoromethyl; and (f) 'halogen' means chlorine, bromine or fluorine.

A further preferred class of compounds of formula I within this second aspect are those in which $R^5$ represents a hydrogen atom.

A further preferred class of compounds of formula I are those wherein:

$R^2$ represents a member selected from the group consisting of $R^{51}$, cyano, —$SR^{41}$, —$O(CH_2)_mOR^{51}$ and —$CO_2R^{51}$, preferably $R^{51}$; and $R^{51}$ represents straight- or branched-chain alkyl having from 1 to 6 carbon atoms, preferably methyl or ethyl.

A further preferred class of compounds of formula I within this second aspect are those wherein:

R represents methyl, isopropyl, t-butyl, cyclopropyl or 1-methylcyclopropyl;

$R^2$ represents chlorine, bromine, fluorine, trifluoromethyl or methoxy;

$R^3$ represents hydrogen, chlorine or methoxy;

$R^5$ represents hydrogen;

$R^{41}$ represents methyl or ethyl; and n is 0, 1 or 2, especially 0 or 2.

In this second aspect, most preferably R is 1-methylcyclopropyl or cyclopropyl.

In a third aspect of this eighth embodiment the invention provides compounds of formula I wherein:

R represents:
straight- or branched-chain alkyl having from 1 to 6 carbon atoms, optionally substituted by one or more halogen atoms which may be the same or different; or
cycloalkyl having from 3 to 6 carbon atoms, optionally bearing one or more substituents which may be the same or different selected from the group consisting of $R^5$ and halogen;

$R^1$ represents hydrogen;

$R^2$ represents:
a hydrogen, chlorine or bromine atom, or
straight- or branched-chain alkyl having from 1 to 6 carbon atoms, bearing a substituent —$OR^{51}$; or
a member selected from the group consisting of $R^{51}$, nitro, cyano, —$S(O)_{p1}R^{41}$, —$OR^{51}$, —$O(CH_2)_mOR^{51}$ and —$CO_2R^{51}$;

$R^3$ represents —$S(O)_nR^{41}$;

$R^4$ and $R^5$, which may be the same or different, each represents:
a halogen or hydrogen atom, or
straight- or branched-chain alkyl having from 1 to 6 carbon atoms, bearing a substituent —$OR^{51}$; or
a member selected from the group consisting of $R^{51}$, nitro, cyano, —$OR^{51}$, —$O(CH_2)_mOR^{51}$, —$S(O)_qR^{41}$ and —$CO_2R^5$;

$R^{41}$ and $R^{51}$, which may be the same or different, each represents:
straight- or branched-chain alkyl having from 1 to 6 carbon atoms, optionally substituted by one or more halogen atoms which may be the same or different;
m is an integer from 1 to 3;
n is zero, 1 or 2; p1 is zero, 1 or 2; q is zero, 1 or 2;
with the proviso that when $R^2$ represents —$S(O)_pR^{41}$ at least one of the substituents p1 and n is zero;

metal complexes thereof, and agriculturally acceptable salts thereof.

In this third aspect a preferred class of compounds of formula I wherein the structural variables are selected such that they meet one or more definitions selected from the group consisting of:

(a) R represents methyl, isopropyl, t-butyl, cyclopropyl or 1-methylcyclopropyl; and/or (b) $R^2$ represents:
a hydrogen, chlorine or bromine atom, or
a member selected from the group consisting of —$OR^{51}$, for example methoxy, ethoxy or trifluoromethoxy, $R^{51}$, for example methyl or trifluoromethyl, nitro, or —$SR^{41}$; and/or (c) $R^4$ and $R^5$, which may be the same or different, each represents:
a halogen atom or hydrogen atom,
straight- or branched-chain alkyl having from 1 to 6 carbon atoms, bearing a substituent —$OR^{51}$, for example methoxymethyl; or
a member selected from the group consisting of $R^{51}$, for example methyl or trifluoromethyl, —$OR^{51}$, for example methoxy, ethoxy or isopropoxy, —$O(CH_2)_m OR^{51}$ where m is 2 or 3, for example 2-ethoxyethoxy or 2-methoxyethoxy,
—$CO_2R^{51}$, for example carbomethoxy, carboethoxy, or carboisopropoxy; or
—$S(O)_qR^{41}$,
provided that at least one of the substituents $R^4$ and $R^5$ represent hydrogen; and/or (d) $R^{41}$ represents:
straight- or branched-chain alkyl having from 1 to 4 carbon atoms, optionally substituted by one or more halogen atoms which may be same or different, for example isopropyl, methyl or ethyl; and/or (e) $R^{51}$ represents:
straight- or branched-chain alkyl having from 1 to 4 carbon atoms, optionally substituted by one or more halogen atoms, which may be the same or different, for example methyl, ethyl, isopropyl, or trifluoromethyl; and (f) 'halogen' represents chlorine, bromine or fluorine.

A further preferred class of compounds of formula I are those in which $R^5$ represents a hydrogen atom.

A further preferred class of compounds of formula I within this third aspect are those wherein:

R represents isopropyl, cyclopropyl or 1-methylcyclopropyl;

$R^2$ represents chlorine, bromine, trifluoromethyl, —$SR^{41}$, methoxy or methyl;

$R^4$ represents fluorine, chlorine, bromine, —$CF_3$, —$S(O)_qR^{41}$ or methyl, $R^5$ represents hydrogen;

$R^{41}$ represents methyl, ethyl or isopropyl;

$R^{51}$ represents methyl, ethyl or n-propyl;

q is zero, one or two.

Examples of compounds embraced by formula (I) include the following:

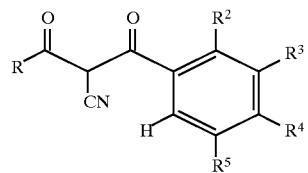

| Cpd No. | R | R² | R³ | R⁴ | R⁵ | mp(°C.) |
|---|---|---|---|---|---|---|
| 1 | cPr | Cl | H | SO2NMe2 | H | 124.5–126 |
| 2 | cPr | CF3 | H | SO2NMe2 | H | 147–153.8 |
| 3 | cPr | SO2NMe2 | H | Cl | H | |
| 4 | cPr | SO2NMe2 | H | CF3 | H | |
| 5 | cPr | SO2NMe2 | H | Br | H | |
| 6 | cPr | SO2NEt2 | H | CF3 | H | |
| 7 | cPr | SO2N(Me)CH2CH2CH3 | H | Cl | H | |
| 8 | cPr | SO2N(Me)-cPr | H | Cl | H | |
| 9 | cPr | SO2N(Et)CH2CH=CH2 | H | Cl | H | |
| 10 | cPr | CF3 | H | SO2NHMe | H | |
| 11 | cPr | CF3 | H | SO2N(Et)CH2CCH | H | |
| 12 | cPr | CF3 | H | SO2N(Me)-cyclohexyl | H | |
| 13 | cPr | 2-N(Me)SO2Me | H | NO2 | H | 203–205 |
| 14 | cPr | N(Me)SO2Me | Br | Br | H | |
| 15 | cPr | N(Me)SO2Me | Br | Cl | H | |
| 16 | cPr | N(Me)SO2Me | Cl | Br | H | |
| 17 | cPr | N(Me)SO2Me | F | F | H | |
| 18 | cPr | N(Me)SO2Me | OMe | Cl | H | |
| 19 | cPr | N(Me)SO2Me | OEt | Cl | H | |
| 20 | cPr | N(Me)SO2Me | OCH2CH2OMe | Cl | H | |
| 21 | cPr | N(Me)SO2Me | CH2OMe | Cl | H | |
| 22 | cPr | N(Me)SO2Me | CH2SMe | Cl | H | |
| 21 | cPr | N(Me)SO2Me | CH2OMe | Cl | H | |
| 22 | cPr | N(Me)SO2Me | CH2SMe | Cl | H | |
| 23 | cPr | N(Me)SO2Me | OCH2CH2OEt | Cl | H | |
| 24 | cPr | N(Me)SO2Me | CH2SEt | Cl | H | |
| 25 | cPr | N(Me)SO2Me | H | CF3 | H | |
| 26 | Me | N(Me)SO2Me | H | CF3 | H | |
| 27 | Et | N(Me)SO2Me | H | CF3 | H | |
| 28 | CH(CH3)2 | N(Me)SO2Me | H | CF3 | H | |
| 29 | cPr-1-Me | N(Me)SO2Me | H | CF3 | H | |
| 30 | cPr | N(Me)SO2Me | H | Cl | H | 127.8–128.8 |
| 31 | iPr | N(Me)SO2Me | H | Cl | H | |
| 32 | cPr-1-Me | N(Me)SO2Me | H | Cl | H | |
| 33 | cPr | N(Me)SO2Me | H | OCF3 | H | |
| 34 | iPr | N(Me)SO2Me | H | OCF3 | H | |
| 35 | cPr-1-Me | N(Me)SO2Me | H | OCF3 | H | |
| 36 | cPr | N(Me)SO2Me | H | OCH2CF3 | H | |
| 37 | cPr | N(Me)SO2Me | H | OCHF2 | H | |
| 38 | cPr | N(Me)SO2Me | H | OCCl=CF2 | H | |
| 39 | cPr | N(Me)SO2Me | H | CHF2 | H | |
| 40 | cPr | N(Me)SO2Me | OCH2CCH | Cl | H | |
| 41 | cPr | N(Me)SO2Me | OCH2CH=CH2 | Cl | H | |
| 42 | cPr | N(Me)SO2Me | SMe | Cl | H | |
| 43 | iPr | N(Me)SO2Me | SMe | Cl | H | |
| 44 | Me | N(Me)SO2Me | SMe | Cl | H | |
| 45 | Et | N(Me)SO2Me | SMe | Cl | H | |
| 46 | cPr-1-Me | N(Me)SO2Me | SMe | Cl | H | |
| 47 | cPr | N(Me)SO2Me | SO2Me | Cl | H | |
| 48 | cPr | N(Me)SO2Me | Cl | SMe | H | |
| 49 | cPr | N(Me)SO2Me | Cl | SO2Me | H | |
| 50 | cPr | N(Me)SO2Me | CH3 | SMe | H | |
| 51 | cPr | N(Me)SO2Me | C(CH3)=CH2 | Cl | H | |
| 52 | cPr | N(Me)SO2Me | H | Cl | F | |
| 53 | cPr | N(Me)SO2Me | H | F | F | |
| 54 | cPr | N(Me)SO2Me | H | SMe | F | |
| 55 | cPr | N(Me)SO2Me | H | CF3 | F | |
| 56 | cPr | N(Me)SO2Me | H | OCF3 | F | |
| 57 | cPr | N(Me)SO2Me | H | SO2Me | H | |
| 58 | cPr | N(Me)SO2Me | H | S(O)Me | H | |
| 59 | cPr | N(Me)SO2Me | H | SMe | H | |
| 60 | cPr | N(Me)SO2Me | H | OCH3 | H | |
| 61 | cPr | N(Me)SO2Me | H | Me | H | 106–108 |
| 62 | cPr | N(Me)SO2Me | H | F | H | |
| 63 | cPr | Me | H | N(Me)SO2Me | H | |
| 64 | cPr | Cl | H | N(Me)SO2Me | H | 115.8–116.6 |
| 65 | cPr | Br | OCH2CH2OMe | N(Me)SO2Me | H | |
| 66 | cPr | Br | CH2OMe | N(Me)SO2Me | H | |

-continued

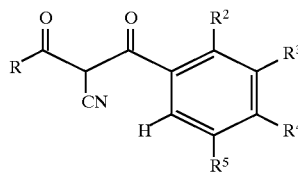

| Cpd No. | R | R² | R³ | R⁴ | R⁵ | mp(°C.) |
|---|---|---|---|---|---|---|
| 67 | cPr | Br | CH2SMe | N(Me)SO2Me | H | |
| 68 | cPr | Cl | H | N(Me)SO2Ph | H | |
| 69 | cPr | Cl | H | N(Me)SO2(Ph-4-Me) | H | |
| 70 | cPr | Cl | H | N(Me)SO2(Ph-4-Cl) | H | |
| 71 | cPr | Cl | H | N(Et)SO2(Ph-4-Me) | H | |
| 72 | cPr | CF3 | H | N(Me)SO2Me | H | |
| 73 | cPr | SO2Me | H | N(Me)SO2Me | H | |
| 74 | cPr | SMe | H | N(Me)SO2Me | H | |
| 75 | cPr | S(O)Me | H | N(Me)SO2Me | H | |
| 76 | cPr | NO2 | H | N(Me)SO2Me | H | 133–134 |
| 77 | cPr | Br | H | N(Me)SO2Me | H | |
| 78 | cPr | OMe | H | N(Me)SO2Me | H | |
| 79 | cPr | CF3 | H | NHSO2Et | H | |
| 80 | cPr | Me | H | NHSO2Et | H | |
| 81 | cPr | CF3 | H | NHSO2Me | H | |
| 82 | cPr | Me | H | NHSO2Me | H | |
| 83 | cPr | Me | H | NHSO2CH2CH=CH2 | H | |
| 84 | cPr | Cl | H | NHSO2-cPr | H | |
| 85 | cPr | Cl | H | NHSO2Me | H | 146–152 |
| 86 | cPr | SMe | N(Me)SO2Me | CF3 | H | |
| 87 | cPr | SMe | N(Me)SO2Me | Cl | H | |
| 88 | cPr | SMe | N(Me)SO2Me | Br | H | |
| 89 | cPr | SMe | N(Me)SO2Me | Me | H | |
| 90 | cPr | SMe | N(Me)SO2Me | OCF3 | H | |
| 91 | cPr | SMe | N(Me)SO2Me | Cl | H | |
| 92 | cPr | SO2CH3 | N(Me)SO2Me | Cl | H | |
| 93 | cPr | S(O)Me | N(Me)SO2Me | Cl | H | |
| 94 | cPr | Cl | N(Me)SO2Me | Cl | H | |
| 95 | cPr | Cl | N(Me)SO2Me | CF3 | H | |
| 96 | cPr | Cl | N(Me)SO2Me | SMe | H | |
| 97 | cPr | Cl | N(Me)SO2Me | OMe | H | |
| 98 | cPr | Me | N(Me)SO2Me | Me | H | |
| 99 | cPr | Me | N(Me)SO2Me | SMe | H | |
| 100 | cPr | CF3 | N(Me)SO2Me | Cl | H | |
| 101 | cPr | CF3 | N(Me)SO2Me | SMe | H | |
| 102 | cPr | CF3 | N(Me)SO2Me | Cl | H | |
| 103 | cPr | SMe | OMe | N(Me)SO2Me | H | |
| 104 | cPr | SMe | Cl | N(Me)SO2Me | H | |
| 105 | cPr | SMe | Me | N(Me)SO2Me | H | |
| 106 | cPr | SMe | Br | N(Me)SO2Me | H | |
| 107 | cPr | SMe | C(CH3)=CH2 | N(Me)SO2Me | H | |
| 108 | cPr | SMe | CH=CH2 | N(Me)SO2Me | H | |
| 109 | cPr | N(Et)SO2Me | H | Cl | H | 120–122 |
| 110 | cPr | N(Et)SO2Me | H | CF3 | H | 101.5–103.8 |
| 111 | cPr | N(Et)SO2Me | H | SMe | H | |
| 112 | cPr | N(Et)SO2Me | H | Br | H | |
| 113 | cPr | N(cPr)SO2Me | H | Cl | H | |
| 114 | cPr | N(cPr)SO2Me | H | CF3 | H | |
| 115 | cPr | N(cPr)SO2Me | H | SMe | H | |
| 116 | cPr | N(cPr)SO2Me | H | Br | H | |
| 117 | cPr | N(Et)SO2Et | H | Cl | H | |
| 118 | cPr | N(Et)SO2Et | H | CF3 | H | |
| 119 | cPr | N(Et)SO2Et | H | SMe | H | |
| 120 | cPr | N(Et)SO2Et | H | Br | H | |
| 121 | cPr | N(Me)SO2-cPr | H | CF3 | H | |
| 122 | cPr | N(Me)S02-cyclopentyl | H | CF3 | H | |
| 123 | cPr | N(CH2CF3)SO2Me | H | CF3 | H | |
| 124 | cPr | N(CH2CH=CH2)SO2Me | H | CF3 | H | |
| 125 | cPr | N(CH2CH=CCl2)SO2Me | H | CF3 | H | |
| 126 | cPr | N(Ph)SO2Me | H | CF3 | H | |
| 127 | cPr | N(Ph-4-Cl)SO2Me | H | CF3 | H | |
| 128 | cPr | N(Me)SO2Me | H | Cl | Cl | |
| 129 | cPr | N(Me)SO2Me | H | Me | Cl | |
| 130 | cPr | N(Me)SO2Me | H | Cl | OMe | |
| 131 | cPr | N(Me)SO2Me | H | Cl | OCH2CH=CH2 | |
| 132 | cPr | N(Me)SO2Me | H | CF3 | Cl | |
| 133 | cPr | N(Me)SO2Me | H | Cl | SMe | |
| 134 | cPr | N(Me)SO2CH2CH=CH2 | H | CF3 | H | |

-continued

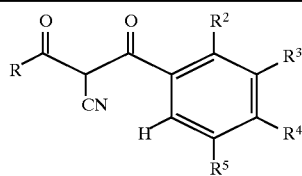

| Cpd No. | R | $R^2$ | $R^3$ | $R^4$ | $R^5$ | mp(°C.) |
|---|---|---|---|---|---|---|
| 135 | cPr | N(Me)SO2CH2C(Cl)=CH2 | H | CF3 | H | |
| 136 | cPr | N(Me)SO2Ph | H | CF3 | H | |
| 137 | cPr | N(Me)SO2(Ph-4-Cl) | H | CF3 | H | |
| 138 | cPr | N(Me)SO2(Ph-4-Me) | H | CF3 | H | |
| 139 | cPr | N(Me)SO2CH2CCH | H | CF3 | H | |
| 140 | cPr | N(Me)SO2CF3 | H | Cl | H | |
| 141 | cPr | N(Me)SO2CF3 | H | CF3 | H | |
| 142 | cPr | SMe | Cl | N(Me)SO2CF3 | H | |
| 143 | cPr | CF3 | H | N(Me)SO2CF3 | H | |
| 144 | cPr | CH2SMe | H | Cl | H | |
| 145 | iPr | CH2SMe | H | Cl | H | |
| 146 | Me | CH2SMe | H | Cl | H | |
| 147 | cPr-1-Me | CH2SMe | H | Cl | H | |
| 148 | cPr | CH2SMe | H | CF3 | H | |
| 149 | iPr | CH2SMe | H | CF3 | H | |
| 150 | Me | CH2SMe | H | CF3 | H | |
| 151 | cPr-1-Me | CH2SMe | H | CF3 | H | |
| 152 | cPr | CH2SO2Me | H | Br | H | 108 |
| 153 | iPr | CH2SMe | H | Br | H | |
| 154 | Me | CH2SMe | H | Br | H | |
| 155 | cPr-1-Me | CH2SMe | H | Br | H | |
| 156 | Et | CH2SMe | H | Br | H | |
| 157 | cPr | CH2SMe | H | Me | H | |
| 158 | cPr | CH2SMe | H | OMe | H | |
| 159 | cPr | CH2SMe | H | OCF3 | H | |
| 160 | cPr | CH2SMe | H | NO2 | H | |
| 161 | cPr | CH2SMe | H | CN | H | |
| 162 | cPr | CH2SMe | Cl | Cl | H | |
| 163 | cPr | CH2SMe | Br | Br | H | |
| 164 | cPr | CH2SMe | OMe | Cl | H | |
| 165 | cPr | CH2SMe | OEt | Cl | H | |
| 166 | cPr | CH2SMe | OCH2CH2OMe | Cl | H | |
| 167 | cPr | CH2SMe | CH2OMe | Cl | H | |
| 168 | cPr | CH2SMe | N(Me)SO2Me | Cl | H | |
| 169 | cPr | CH2SMe | N(Me)SO2Et | CF3 | H | |
| 170 | cPr | CH2SMe | H | N(Me)SO2Me | H | |
| 171 | cPr | CH2SMe | CO2Me | Cl | H | |
| 172 | cPr | CH2SMe | CO2Me | CF3 | H | |
| 173 | cPr | CH2SMe | CO2Et | Cl | H | |
| 174 | cPr | CH2SMe | CO2Et | CF3 | H | |
| 175 | cPr | CH2S(O)Me | H | Cl | H | |
| 176 | cPr | CH2S(O)Me | H | CF3 | H | |
| 177 | cPr | CH2S(O)Me | H | Br | H | |
| 178 | cPr | CH2S(O)Me | H | Me | H | |
| 179 | cPr | CH2S(O)Me | H | OMe | H | |
| 180 | cPr | CH2S(O)Me | H | OCF3 | H | |
| 181 | cPr | CH2S(O)Me | Cl | Cl | H | |
| 182 | Me | CH2S(O)Me | Cl | Cl | H | |
| 183 | cPr-1-Me | CH2S(O)Me | Cl | Cl | H | |
| 184 | iPr | CH2S(O)Me | Cl | Cl | H | |
| 185 | cPr | CH2S(O)Me | Br | Br | H | |
| 186 | cPr | CH2S(O)Me | OMe | Cl | H | |
| 187 | cPr | CH2S(O)Me | OEt | Cl | H | |
| 188 | cPr | CH2S(O)Me | CO2Me | Cl | H | |
| 189 | cPr | CH2S(O)Me | CO2Me | CF3 | H | |
| 190 | cPr | CH2SO2Me | H | Cl | H | |
| 191 | cPr | CH2SO2Me | C(O)Me | Cl | H | |
| 192 | cPr | CH2SO2Me | C(Me)=CH2 | Cl | H | |
| 193 | cPr | CH2SO2Me | H | CF3 | H | |
| 194 | cPr | CH2SO2Me | H | Br | H | |
| 195 | cPr | CH2SO2Me | H | Me | H | |
| 196 | cPr | CH2SO2Me | H | OMe | H | |
| 197 | cPr | CH2SO2Me | H | OCF3 | H | |
| 198 | cPr | CH2SO2Me | Cl | Cl | H | |
| 199 | cPr | CH2SO2Me | Br | Br | H | |
| 200 | cPr | CH2SO2Me | OMe | Cl | H | |
| 201 | cPr | CH2SO2Me | OEt | Cl | H | |
| 202 | cPr | CH2SO2Me | CO2Me | Cl | H | |

-continued

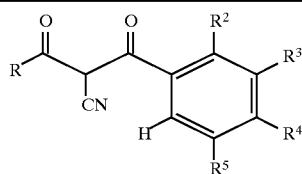

| Cpd No. | R | $R^2$ | $R^3$ | $R^4$ | $R^5$ | mp(°C.) |
|---|---|---|---|---|---|---|
| 203 | cPr | CH2SO2Me | CO2Et | CF3 | H | |
| 204 | cPr | CH2SO2Me | CO2Me | CF3 | H | |
| 205 | cPr | CH2SO2Me | C(O)NMe2 | Cl | H | |
| 206 | cPr | CH2SMe | SMe | Cl | H | |
| 207 | cPr | CH2SMe | SMe | CF3 | H | |
| 208 | cPr | CH2SMe | SO2Me | Cl | H | |
| 209 | cPr | CH2S(O)Me | SMe | Cl | H | |
| 210 | cPr | CH2SO2Me | SMe | Cl | H | |
| 211 | cPr | CH2SMe | H | SMe | H | |
| 212 | cPr | CH2SO2Me | H | SMe | H | |
| 213 | cPr | CH2S(O)Me | H | SMe | H | |
| 214 | cPr | CH2SMe | H | SO2Me | H | |
| 215 | cPr | CH2SMe | Cl | SMe | H | |
| 216 | cPr | CH2SMe | Me | SMe | H | |
| 217 | cPr | CH2SMe | OMe | SMe | H | |
| 218 | cPr | Me | CH2SMe | SMe | H | |
| 219 | Me | Me | CH2SMe | SMe | H | |
| 220 | cPr-1-Me | Me | CH2SMe | SMe | H | |
| 221 | iPr | Me | CH2SMe | SMe | H | |
| 222 | cPr | Cl | CH2SMe | SMe | H | |
| 223 | Me | Cl | CH2SMe | SMe | H | |
| 224 | cPr-1-Me | Cl | CH2SMe | SMe | H | |
| 225 | iPr | Cl | CH2SMe | SMe | H | |
| 226 | cPr | CF3 | CH2SMe | SMe | H | |
| 227 | cPr | OCF3 | CH2SMe | SMe | H | |
| 228 | cPr | OMe | CH2SMe | SMe | H | |
| 229 | cPr | SMe | Me | CH2SMe | H | |
| 230 | cPr | SMe | Cl | CH2SMe | H | |
| 231 | cPr | SMe | OMe | CH2SMe | H | |
| 232 | cPr | SMe | OEt | CH2SMe | H | |
| 233 | cPr | SMe | CO2Me | CH2SMe | H | |
| 234 | cPr | Me | SMe | CH2SMe | H | |
| 235 | cPr | CF3 | SMe | CH2SMe | H | |
| 236 | cPr | Cl | SMe | CH2SMe | H | |
| 237 | cPr | Br | SMe | CH2SMe | H | |
| 238 | cPr | OMe | SMe | CH2SMe | H | |
| 239 | cPr | OCF3 | SMe | CH2SMe | H | |
| 240 | cPr | Cl | CH2SMe | H | H | |
| 241 | cPr | CF3 | CH2SMe | H | H | |
| 242 | cPr | Me | CH2SMe | H | H | |
| 243 | cPr | OMe | CH2SMe | H | H | |
| 244 | cPr | Cl | CH2S(O)Me | H | H | |
| 245 | cPr | CF3 | CH2S(O)Me | H | H | |
| 246 | cPr | Me | CH2S(O)Me | H | H | |
| 247 | cPr | OMe | CH2S(O)Me | H | H | |
| 248 | cPr | Cl | CH2SO2Me | H | H | |
| 249 | cPr | CF3 | CH2SO2Me | H | H | |
| 250 | cPr | Me | CH2SO2Me | H | H | |
| 251 | cPr | OMe | CH2SO2Me | H | H | |
| 252 | cPr | Cl | CH2SMe | Cl | H | |
| 253 | Et | Cl | CH2SMe | Cl | H | |
| 254 | iPr | Cl | CH2SMe | Cl | H | |
| 255 | cPr | CF3 | CH2SMe | Cl | H | |
| 256 | cPr | Me | CH2SMe | Cl | H | |
| 257 | cPr-1-Me | Me | CH2SMe | Cl | H | |
| 258 | Et | Me | CH2SMe | Cl | H | |
| 259 | iPr | Me | CH2SMe | Cl | H | |
| 260 | Me | Me | CH2SMe | Cl | H | |
| 261 | cPr | OMe | CH2SMe | Cl | H | |
| 262 | cPr | Cl | CH2S(O)Me | Cl | H | |
| 263 | cPr | CF3 | CH2S(O)Me | Cl | H | |
| 264 | cPr | Me | CH2S(O)Me | Cl | H | |
| 265 | cPr | OMe | CH2S(O)Me | Cl | H | |
| 266 | cPr | Cl | CH2SO2Me | Cl | H | |
| 267 | cPr | CF3 | CH2SO2Me | Cl | H | |
| 268 | cPr | Me | CH2SO2Me | Cl | H | |
| 269 | cPr | OMe | CH2SO2Me | Cl | H | |
| 270 | cPr | Cl | CH2SMe | CF3 | H | |

-continued

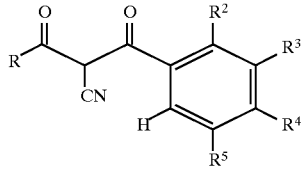

| Cpd No. | R | $R^2$ | $R^3$ | $R^4$ | $R^5$ | mp(°C.) |
|---|---|---|---|---|---|---|
| 271 | cPr | F | CH2SMe | Cl | H | |
| 272 | cPr | CH2SMe | H | Cl | Cl | |
| 273 | cPr | CH2SMe | H | Cl | F | |
| 274 | cPr | CH2SMe | H | Me | Cl | |
| 275 | cPr | Me | H | Cl | CH2SMe | |
| 276 | cPr | F | H | Cl | CH2SMe | |
| 277 | cPr | Cl | H | F | CH2SMe | |
| 278 | cPr | C(CH3)SMe | H | Cl | H | |
| 279 | cPr | C(CH3)SMe | H | CF3 | H | |
| 280 | cPr | C(CH3)SMe | Cl | Cl | H | |
| 281 | cPr | CH2SEt | H | Cl | H | |
| 282 | cPr | CH2SEt | H | CF3 | H | |
| 283 | iPR | CH2SEt | H | CF3 | H | |
| 284 | cPr-1-Me | CH2SEt | H | CF3 | H | |
| 285 | cPr | CH2SEt | Cl | Cl | H | |
| 286 | cPr | CH2(Me)S-cPr | H | Cl | H | |
| 287 | cPr | CH2S-iPr | H | Cl | H | |
| 288 | cPr | CH2SPh | H | Cl | H | |
| 289 | cPr | CH2S(Ph-4-Cl) | H | Cl | H | |
| 290 | cPr | CH2S(Ph-3,4-Cl2) | H | Cl | H | |
| 291 | cPr | CH2SCH2CH=CH2 | H | CF3 | H | |
| 292 | cPr | CH2SCH2C(Cl)=CCl2 | H | Br | H | |
| 293 | cPr | CH2SCH2CCH | H | Cl | H | |
| 294 | cPr | CH2S-cPr | H | Cl | H | |
| 295 | cPr | CH2SO2-cPr | H | Cl | H | |
| 296 | cPr | CH2S-cPr | Cl | Br | H | |
| 297 | cPr | CH2SO2-cPr | Cl | Br | H | |
| 298 | cPr | CH2S-cyclohexyl | H | Cl | H | |
| 299 | cPr | CH2SO2NMe2 | H | Cl | H | |
| 300 | cPr | CH2SO2NMe2 | Cl | Cl | H | |
| 301 | cPr | (CH2)2SMe | H | Br | H | |
| 302 | cPr | CH(Me)2SMe | H | Br | H | |
| 303 | cPr | (CH2)3SEt | H | Br | H | |
| 304 | cPr | (CH2)2SCH2CH=CH2 | H | Br | H | |
| 305 | cPr | SPh | H | SPh | H | |
| 306 | cPr | SO2Ph | H | H | SO2Me | |
| 307 | cPr | SPh | Cl | Cl | H | |
| 308 | cPr | SPh | H | Cl | H | |
| 309 | cPr | SO2Ph | H | Cl | H | |
| 310 | cPr | SO2Ph | H | CF3 | H | 153.5 |
| 311 | cPr | SPh | H | CF3 | H | 77.5 |
| 312 | cPr | S(Ph-2Cl) | H | CF3 | H | |
| 313 | cPr | S(Ph-3-Cl) | H | Cl | H | |
| 314 | cPr | S(O)(Ph-3-Cl) | H | Cl | H | |
| 315 | cPr | SO2(Ph-3-Cl) | H | Cl | H | |
| 316 | cPr | S(O)(Ph-4-Cl) | H | Cl | H | |
| 317 | cPr | S02(Ph-4-Cl) | H | Cl | H | |
| 318 | cPr | S(Ph-3-OMe) | H | Cl | H | |
| 319 | cPr | S(O)(Ph-3-OMe) | H | Cl | H | |
| 320 | cPr | SO2(Ph-3-OMe) | H | Cl | H | |
| 321 | Ph | SO2Me | H | CF3 | H | |
| 322 | Ph-3,4-F$_2$ | SO2Me | H | CF3 | H | |
| 323 | cPr | S(Ph-4-CN) | H | CF3 | H | |
| 324 | cPr | SPh | OMe | Cl | | |
| 325 | cPr | SPh | C(Me)=CH2 | Cl | | |
| 326 | cPr | SPh | SMe | Cl | H | |
| 327 | cPr | SPh | Me | SMe | H | |
| 328 | cPr | SO2Ph | Cl | SMe | H | |
| 329 | cPr | S(Ph-3-CF3) | H | CF3 | H | |
| 330 | cPr | S(Ph-3-Cl-4-CF3) | H | CF3 | H | |
| 331 | cPr | SO2(Ph-2,4-Cl2) | H | CF3 | H | |
| 332 | cPr | Me | SPh | Me | H | |
| 333 | cPr | SMe | SPh | Cl | H | |
| 334 | cPr | SO2Me | SPh | Cl | H | |
| 335 | cPr | Me | CO2Me | SPh | H | |
| 336 | Ph-3-CF$_3$ | SO2Me | H | CF3 | H | |
| 337 | Ph-3,5-(CF$_3$)$_2$ | SMe | H | Cl | H | 146–149 |
| 338 | Ph-4-OMe | SMe | H | Cl | H | |

-continued

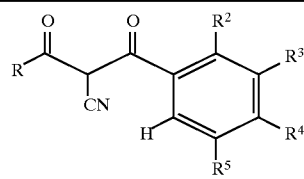

| Cpd No. | R | R² | R³ | R⁴ | R⁵ | mp(°C.) |
|---|---|---|---|---|---|---|
| 339 | Ph-4-Cl | SOMe | H | Cl | H | |
| 340 | cPr | SMe | OPh | Cl | H | |
| 341 | cPr | S(O)Me | OPh | Cl | H | |
| 342 | cPr | SO2Me | O(Ph-4-NO2) | Br | H | |
| 343 | cPr | OPh | SMe | Cl | H | |
| 344 | cPr | Me | SMe | OPh | H | |
| 345 | cPr | SMe | OPh(4-CF3) | Cl | H | |
| 346 | cPr | SMe | H | F | OPh | |
| 347 | cPr | Me | S-cPr | OPh | H | |
| 348 | cPr | iPr | SCH2CF3 | O(Ph-3,4-Cl2) | H | |
| 349 | cPr | SMe | C(CH3)=CH2 | OPh | H | |
| 350 | cPr | S(O)Et | C=CCl2 | OPh | H | |
| 351 | cPr | SO2Me | C(Cl)=CHCl | O(Ph-4-Cl) | H | |
| 352 | cPr | SMe | OCH2CH=CH2 | Cl | H | |
| 353 | cPr | S(O)Me | OCH2CH=CH2 | Cl | H | |
| 354 | cPr | SO2Me | OCH2CH=CH2 | Cl | H | |
| 355 | cPr | SMe | OCH2CCH | Cl | H | |
| 356 | cPr | S(O)Me | OCH2CCH | Cl | H | |
| 357 | cPr | SO2Me | OCH2CCH | Cl | H | |
| 358 | cPr | SMe | OCH2CH=CH2 | Br | H | |
| 359 | cPr | SO2Me | OCH2CH=CH2 | Br | H | |
| 360 | cPr | SMe | OCH2CCH | Br | H | |
| 361 | cPr | SO2Me | OCH2CCH | Br | H | |
| 362 | cPr | SMe | OCH2C(Cl)=CH2 | Cl | H | |
| 363 | cPr | SMe | OCH(Me)CH=C(Me)2 | Cl | H | |
| 364 | cPr | SMe | OC(Me)=CH2 | Cl | H | |
| 365 | cPr | SMe | OC(Cl)-=CCl2 | Cl | H | |
| 366 | cPr | SMe | OC(F)=CF2 | Cl | H | |
| 367 | cPr | SMe | OCH2CH=CHCH3 | Cl | H | |
| 368 | cPr | SMe | OCH2CCCH3 | Cl | H | |
| 369 | cPr | SMe | OCH2CCBr | Cl | H | |
| 370 | cPr | OCH2CH=CH2 | SMe | Br | H | |
| 371 | cPr | OCH2CH=CCl2 | SO2Me | F | H | |
| 372 | cPr | OCH(Me)=CCl2 | SMe | SMe | H | |
| 373 | cPr | OC(Cl)=CF2 | Cl | SO2Me | H | |
| 374 | cPr | Me | OCH2CH=CH2 | SO2Me | H | |
| 375 | cPr | Br | OCH2CCH | SO2Me | H | |
| 376 | cPr | SMe | H | Cl | OCH2CH=CH2 | |
| 377 | cPr | CF3 | SO2Me | OCH2CH=CH2 | H | |
| 378 | cPr | Et | SEt | OCH2CCH | H | |
| 379 | cPr | Me | S-cPr | OC(Cl)=CHCF3 | H | |
| 380 | cPr | S(O)Me | Cl | OC(Cl)=CF2 | H | |
| 381 | cPr | S(O)Me | Cl | OCH2C(Cl)=CCl2 | H | |
| 382 | cPr | S(O)Me | Cl | OCH(Me)CH=CMe2 | H | |
| 383 | cPr | S(O)Me | Cl | CH(Me)CCMe | H | |
| 384 | cPr | OSO2Me | H | H | H | 103.9–105.5 |
| 385 | cPr | OSO2Me | H | Cl | H | 140–140.6 |
| 386 | iPr | OSO2Me | H | Cl | H | |
| 387 | Me | OSO2Me | H | Cl | H | |
| 388 | Et | OSO2Me | H | Cl | H | |
| 389 | cPr-1-Me | OSO2Me | H | Cl | H | |
| 390 | cPr | OSO2Me | H | Br | H | |
| 391 | cPr | OSO2Me | H | CF3 | H | |
| 392 | cPr | OSO2Me | H | Me | H | |
| 393 | cPr | OSO2Me | H | H | Cl | 131.1–133.3 |
| 394 | cPr | OSO2Me | H | H | F | |
| 395 | cPr | OSO2Me | H | F | F | |
| 396 | cPr | OSO2Me | H | Cl | Cl | |
| 397 | cPr | OSO2Me | H | F | OMe | |
| 398 | cPr | OSO2Me | Cl | Cl | H | |
| 399 | cPr | OSO2Me | Br | Cl | H | |
| 400 | cPr | OSO2Me | OEt | Cl | H | |
| 401 | cPr | OSO2CF3 | H | Cl | H | |
| 402 | cPr | OSO2CF3 | H | H | Cl | |
| 403 | cPr | OSO2CF3 | Cl | Cl | H | |
| 404 | cPr | OSO2-iPr | H | H | Cl | |
| 405 | cPr | OSO2-cPr | H | H | Cl | |
| 406 | cPr | OSO2-sBu | H | H | Cl | |

-continued

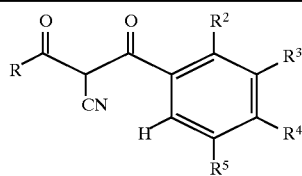

| Cpd No. | R | R² | R³ | R⁴ | R⁵ | mp(°C.) |
|---|---|---|---|---|---|---|
| 407 | cPr | SMe | OSO2Me | H | H | |
| 408 | cPr | SMe | OSO2CF3 | H | H | |
| 409 | cPr | SMe | H | OSO2Me | H | |
| 410 | cPr | SMe | H | H | OSO2Me | |
| 411 | cPr | SMe | OSO2Me | Cl | H | |
| 412 | cPr | SO2Me | OSO2Me | Cl | H | |
| 413 | cPr | S(O)Me | OSO2CH2CH=CH2 | Cl | H | |
| 414 | cPr | S(O)Me | OSO2-cPr | Cl | H | |
| 415 | cPr | S(O)Me | OSO2Et | Cl | H | |
| 416 | cPr | S(O)Me | OSO2CF3 | Cl | H | |
| 417 | cPr | S(O)Me | OSO2NMe2 | Cl | H | |
| 418 | cPr | SMe | Me | OSO2Me | H | |
| 419 | cPr | SMe | Cl | OSO2Me | H | |
| 420 | cPr | SMe | CHF2 | OSO2Me | H | |
| 421 | cPr | SMe | C(O)Me | OSO2Me | H | |
| 422 | cPr | OSO2Et | H | H | H | 54–58 |
| 423 | cPr | OSO2Et | H | Cl | H | |
| 424 | cPr | OSO2Et | H | CF3 | H | |
| 425 | cPr | OSO2Et | Cl | Cl | H | |
| 426 | cPr | OSO2Et | Br | Br | H | |
| 427 | cPr | SMe | OSO2Et | Cl | H | |
| 428 | cPr | OSO2Ph | H | Cl | H | |
| 429 | cPr | OSO2Ph | H | CF3 | H | |
| 430 | cPr | OSO2Ph | Cl | Cl | H | |
| 431 | cPr | OSO2Ph | Br | Br | H | |
| 432 | cPr | OSO2(Ph-4-Cl) | H | Cl | H | |
| 433 | cPr | OSO2(Ph-4-Cl) | H | CF3 | H | |
| 434 | cPr | OSO2(Ph-4-Cl) | Cl | Cl | H | |
| 435 | cPr | OSO2(Ph-4-Cl) | Br | Br | H | |
| 436 | cPr | OSO2NMe2 | H | H | H | 134–136.4 |
| 437 | cPr | OSO2NMe2 | H | CF3 | H | |
| 438 | cPr | OSO2NMe2 | H | Cl | H | |
| 439 | cPr | OSO2NMe2 | Cl | Cl | H | |
| 440 | cPr | OSO2N(Me)Et | H | Cl | H | |
| 441 | cPr | OSO2N(Me)-cPr | H | Cl | H | |
| 442 | cPr | OSO2N(iPr)2 | H | Cl | H | |
| 443 | cPr | Me | H | OS2N(Et)-cyclohexyl | H | |
| 444 | cPr | Me | H | OSO2NEt2 | H | |
| 445 | cPr | SMe | OSO2Ph | Cl | H | |
| 446 | cPr | SMe | OSO2(Ph-2,4-Cl2) | Cl | H | |
| 447 | cPr | SMe | OSO2(Ph-3-CF3) | Cl | H | |
| 448 | cPr | SMe | OSO2(Ph-4-NO2) | Cl | H | |
| 449 | cPr | OSO2Ph | Me | SMe | H | |
| 450 | cPr | Sme | H | F | OSO2Me | |
| 451 | cPr | SMe | H | Cl | OSO2Me | |
| 452 | cPr | SMe | H | CF3 | OSO2Me | |
| 453 | cPr | SO2Me | OSO2Me | Cl | H | |
| 454 | cPr | SMe | H | C(F)=CCl2 | H | |
| 455 | cPr | S(O)Me | H | C(F)=CCl2 | H | |
| 456 | cPr | SO2Me | H | C(F)=CCl2 | H | |
| 457 | cPr | SMe | H | CH=CCl2 | H | |
| 458 | cPr | S(O)Me | H | CH=CCl2 | H | |
| 459 | cPr | SO2Me | H | CH=CCl2 | H | |
| 460 | cPr | SMe | H | C(Cl)=CHCl | H | |
| 461 | cPr | S(O)Me | H | C(Cl)=CHCl | H | |
| 462 | cPr | SO2Me | H | C(Cl)=CHCl | H | |
| 463 | cPr | S(O)Me | Cl | C(F)=CCl2 | H | |
| 464 | cPr | S(O)Me | Cl | CH=CCl2 | H | |
| 465 | cPr | S(O)Me | Cl | C(Cl)=CHCl | H | |
| 466 | cPr | SMe | Cl | CH=C(Cl)CF3 | H | |
| 467 | cPr | SMe | Cl | CH=CBr2 | H | |
| 468 | cPr | S(O)Me | C(Me)=CH2 | Cl | H | |
| 469 | cPr | S(O)Me | C(Me)=CH2 | Br | H | |
| 470 | cPr | S(O)Me | C(Me)=CH2 | CF3 | H | |
| 471 | cPr | S(O)Me | C(Me)=CH2 | Me | H | |
| 472 | cPr | SMe | C(Me)=CH2 | Cl | H | |
| 473 | cPr | SMe | C(Me)=CH2 | Br | H | |
| 474 | cPr | SMe | C(Me)=CH2 | CF3 | H | |

-continued

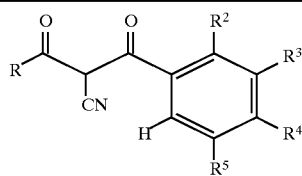

| Cpd No. | R | R² | R³ | R⁴ | R⁵ | mp(°C.) |
|---|---|---|---|---|---|---|
| 475 | cPr | SMe | C(Me)=CH2 | Me | H | |
| 476 | cPr | SO2Me | C(Me)=CH2 | Cl | H | |
| 477 | cPr | SO2Me | C(Me)=CH2 | Br | H | |
| 478 | cPr | SO2Me | C(Me)=CH2 | CF3 | H | |
| 479 | cPr | SO2Me | C(Me)=CH2 | Me | H | |
| 480 | cPr | SMe | CH=CH2 | Cl | H | |
| 481 | cPr | SMe | CH=CH2 | Br | H | |
| 482 | cPr | SMe | CH=CH2 | CF3 | H | |
| 483 | cPr | SMe | CH=CH2 | Me | H | |
| 484 | cPr | SO2Me | CH=CH2 | Cl | H | |
| 485 | cPr | SO2Me | CH=CH2 | Br | H | |
| 486 | cPr | SO2Me | CH=CH2 | CF3 | H | |
| 487 | cPr | SO2Me | CH=CH2 | Me | H | |
| 488 | cPr | SO2Me | C(Me)=CHMe | Cl | H | |
| 489 | cPr | SO2Me | C(Me)=CHMe | CF3 | H | |
| 490 | cPr | SO2Me | C(Me)C=C(Me)2 | Cl | H | |
| 491 | cPr | SO2Me | C(Me)C=C(Me)2 | CF3 | H | |
| 492 | cPr | SMe | CH=CHCH2CH3 | Br | H | |
| 493 | cPr | SMe | CH=CHCH2CH3 | OCF3 | H | |
| 494 | cPr | SO2Me | CCMe | Cl | H | |
| 495 | cPr | SO2Me | CH(Me)CCMe | Cl | H | |
| 496 | cPr | SO2Me | CH(Me)CCH | Cl | H | |
| 497 | cPr | S(O)Me | H | C(Me)=CH2 | H | |
| 498 | cPr | S(O)Me | Cl | C(Me)=CH2 | H | |
| 499 | cPr | S(O)Me | OEt | C(Me)=CH2 | H | |
| 500 | cPr | SO2Me | H | CCH | H | |
| 501 | cPr | SO2Me | Cl | CCH | H | |
| 502 | cPr | SO2Me | Br | CCH | H | |
| 503 | cPr | SO2Me | OEt | CCH | H | |
| 504 | cPr | C(Me)=CH2 | H | SO2Me | H | |
| 505 | cPr | CCH | H | SO2Me | H | |
| 506 | cPr | Cl | C(Cl)=CHCl | SO2Me | H | |
| 507 | cPr | Cl | CH=CCl2 | SO2Me | H | |
| 508 | cPr | Cl | C(F)=CF2 | SO2Me | H | |
| 509 | cPr | Cl | CH=C(Cl)CF3 | SO2Me | H | |
| 510 | cPr | Cl | CH=CBr2 | SO2Me | H | |
| 511 | cPr | C(Cl)=CHCl | H | SMe | H | |
| 512 | cPr | CH=CCl2 | H | SMe | H | |
| 513 | cPr | C(F)=CF2 | H | SMe | H | |
| 514 | cPr | CH=C(Cl)CF3 | H | SMe | H | |
| 515 | cPr | CH=CBr2 | H | SMe | H | |
| 516 | cPr | S-cyclohexyl | H | CF3 | H | oil |
| 517 | cPr | SO2-cyclohexyl | H | CF3 | H | 60–62 |
| 518 | cPr | S-cPr | H | CF3 | H | |
| 519 | cPr | SO2-cPr | H | CF3 | H | |
| 520 | cPr | S(O)-cPr | H | CF3 | H | |
| 521 | cPr | S-cyclopentyl | H | CF3 | H | |
| 522 | cPr | S-cPr | Cl | Cl | H | |
| 523 | cPr | S(O)-cPr | Cl | Cl | H | |
| 524 | cPr | SO2-cPr | Cl | Cl | H | |
| 525 | CH2Ph | SO2Me | H | CF3 | H | |
| 526 | CH2(Ph-3-CF3) | SO2Me | H | CF3 | H | |
| 527 | CH2(Ph-4-OMe) | SO2Me | H | CF3 | H | |
| 528 | cPr | SMe | C(O)NMe2 | Cl | H | |
| 529 | cPr | SMe | C(O)NH-iPr | Cl | H | |
| 530 | cPr | SMe | C(O)N(Me)Et | Cl | H | |
| 531 | cPr | SMe | H | C(O)NMe2 | H | |
| 532 | cPr | SO2Me | C(O)Me | Cl | H | |
| 533 | cPr | SO2Me | C(O)-cPr | Cl | H | |
| 534 | cPr | SO2Me | C(O)-iPr | Cl | H | |
| 535 | cyclohexyl | SO2Me | H | CF3 | H | |
| 536 | cyclopentyl | SO2Me | H | CF3 | H | |
| 537 | cPr | SMe | O(CH2)2O-cPr | Cl | H | |
| 538 | cPr | SMe | O(CH2)2OCH2CH=CH2 | Cl | H | |
| 539 | cPr | SMe | O(CH2)2OC(Cl)=CCl2 | Cl | H | |
| 540 | cPr | SMe | O(CH2)2OC(Me)C=C(Me)2 | Cl | H | |
| 541 | cPr | SMe | O(CH2)2O-cyclopentyl | Cl | H | |
| 542 | cPr | SMe | OCH2O-cPr | Cl | H | |

-continued

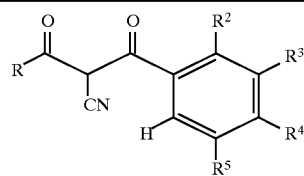

| Cpd No. | R | $R^2$ | $R^3$ | $R^4$ | $R^5$ | mp(°C.) |
|---|---|---|---|---|---|---|
| 543 | cPr | SMe | OCH2O—CH2CCH | Cl | H | |
| 544 | cPr | SO2Me | NMe2 | Cl | H | |
| 545 | cPr | SO2Me | N(Et)-cyclohexyl | Cl | H | |
| 546 | cPr | SO2Me | N(iPr)2 | Cl | H | |
| 547 | cPr | SO2Me | H | NMe2 | H | |
| 548 | cPr | SO2Me | H | N(Et)-cyclohexyl | H | |
| 549 | cPr | SO2Me | H | N(iPr)2 | H | |
| 550 | cPr | Ph | H | SMe | H | |
| 551 | cPr | Ph | H | SO2Me | H | |
| 552 | cPr | Ph | H | S(O)Me | H | |
| 553 | cPr | Ph-4-Cl | H | SO2Me | H | |
| 554 | cPr | Ph-2,4-(Me)2 | H | SO2Me | H | |
| 555 | cPr | SMe | H | Ph | H | |
| 556 | cPr | SO2Me | H | Ph | H | |
| 557 | cPr | S(O)Me | H | Ph | H | |
| 558 | cPr | SMe | H | Ph-4-Cl | H | |
| 559 | cPr | SMe | H | Ph-4-Me | H | |
| 560 | cPr | SMe | H | Ph-3-CF3 | H | |
| 561 | cPr | SO2Me | cPr | H | H | |
| 562 | cPr | SO2Me | H | cPr | H | |
| 563 | cPr | SO2Me | H | cyclopentyl | H | |
| 564 | cPr | SO2Me | cyclohexyl | Cl | H | |
| 565 | cPr | SO2Me | Cl | cPr | H | |
| 566 | cPr | OSO2CH2CN | H | H | H | |
| 567 | cPr | OSO2CO2Me | H | H | H | |
| 568 | cPr | SCH2CN | H | CF3 | H | |
| 569 | cPr | SCH2CO2Et | H | CF3 | H | |
| 570 | cPr | SO2CH2CN | H | CF3 | H | |
| 571 | cPr | SO2CH2CO2Et | H | CF3 | H | |
| 572 | cPr | CF3 | H | SCH2CO2Et | H | |
| 573 | cPr | CF3 | H | SO2CH2CO2Et | H | |
| 574 | cPr | N(CO2Me)SO2Me | H | CF3 | H | |
| 575 | cPr | N(COMe)SO2Me | H | CF3 | H | |
| 576 | cPr | N(SO2Me)2 | H | CF3 | H | |
| 577 | cPr | N(Me)SO2NMe2 | H | CF3 | H | |
| 578 | cPr | N(OMe)SO2Me | H | CF3 | H | |
| 579 | iPr | N(OMe)SO2Me | H | CF3 | H | |
| 580 | cPr-1-Me | N(OMe)SO2Me | H | CF3 | H | |
| 581 | cPr | N(O-iPr)SO2Me | H | CF3 | H | |
| 582 | cPr | N(OEt)SO2Me | H | CF3 | H | |
| 583 | cPr | SO2N(Me)CO2Et | H | CF3 | H | |
| 584 | cPr | SO2N(Me)COMe | H | CF3 | H | |
| 585 | cPr | CF3 | H | SO2NHCO2Et | H | |
| 586 | cPr | $CH_2SO_2Me$ | H | H | H | |
| 587 | cPr | Cl | H | $CH_2SMe$ | H | Oil |
| 588 | cPr | $N(OMe)SO_2Me$ | H | Cl | H | |
| 589 | cPr | $CH_2SMe$ | Br | Cl | H | |
| 590 | cPr | SMe | H | $CH_2SMe$ | H | |
| 591 | cPr | OMe | H | $CH_2SMe$ | H | |
| 592 | cPr | ⟨pyrrolidinyl-SO2⟩ | H | $CF_3$ | H | |
| 593 | cPr | ⟨piperidinyl-SO2⟩ | H | $CF_3$ | H | |
| 594 | cPr | ⟨morpholinyl-SO2⟩ | H | $CF_3$ | H | |

-continued

Structure: R-C(=O)-CH(CN)-C(=O)-phenyl ring with R² (ortho), R³ (meta), R⁴ (para), R⁵ (meta), H (other ortho)

| Cpd No. | R | R² | R³ | R⁴ | R⁵ | mp(°C.) |
|---|---|---|---|---|---|---|
| 595 | cPr | SO₂Me | C(=O)-N(pyrrolidinyl) | Cl | H | |
| 596 | cPr | SO₂Me | C(=O)-N(piperidinyl) | Cl | H | |
| 597 | cPr | SO₂Me | C(=O)-N(morpholinyl) | Cl | H | |
| 598 | cPr | SO₂Me | C(=O)-N(4-methylpiperazinyl) | Cl | H | |
| 599 | 1-(SMe)cyclopropyl-CH< | S(O)Me | Cl | Cl | H | |
| 600 | 1-(OMe)cyclopropyl-CH< | S(O)Me | Cl | Cl | H | |
| 601 | 1-F-cyclopropyl | S(O)Me | Cl | Cl | H | |
| 602 | cyclohexyl-CH₂ | SO₂Me | Cl | Cl | H | |
| 603 | cPr | SO₂-N(piperidinyl) | H | CF₃ | H | |
| 604 | cPr | SO₂-N(piperidinyl) | Cl | Cl | H | |
| 605 | cPr | OSO₂-N(pyrrolidinyl) | H | H | H | |
| 606 | cPr | SMe | OSO₂-N(morpholinyl) | Cl | H | |

-continued

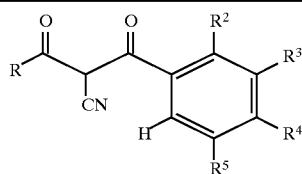

| Cpd No. | R | R² | R³ | R⁴ | R⁵ | mp(°C.) |
|---|---|---|---|---|---|---|
| 607 | cPr | OSO₂—N(morpholine) | H | H | H | |
| 608 | cPr | OSO₂—N(morpholine) | H | CF₃ | H | |
| 609 | cPr | SO₂Me | CO—N(2,6-dimethylpiperidine) | Cl | H | |
| 610 | cPr | SO₂Me | CO—N(2,6-dimethylpiperidine) | CF₃ | H | |
| 611 | cPr | SO2Me | H | H | H | 155 |
| 612 | cPr | SO2Me | H | Cl | H | 116 |
| 613 | cPr | SO2Et | H | H | H | 169 |
| 614 | cPr | SO2iPr | H | H | H | 189 |
| 615 | 1-Me-cPr | SO2Me | H | Cl | H | 122 |
| 616 | iPr | SO2Me | H | Cl | H | 115.5 |
| 617 | cPr | SO2Me | H | Me | H | 129.5 |
| 618 | cPr | SO2Me | H | OMe | H | 151.5 |
| 619 | cPr | SMe | H | Cl | H | 154.5 |
| 620 | cPr | SO2Me | H | Br | H | 159 |
| 621 | cPr | SO2Me | H | CF3 | H | 107.5 |
| 622 | cPr | SMe | Cl | Cl | H | 110–112 |
| 623 | cPr | SO2Me | Cl | Cl | H | 88–90 |
| 624 | cPr | SOMe | Cl | Cl | H | 145.1–146.7 |
| 625 | cPr | SO2sBu | H | CF3 | H | 115–117 |
| 626 | cPr | SsBu | H | CF3 | H | Gum |
| 627 | cPr | SMe | F | Cl | H | 121.2–121.6 |
| 628 | cPr | SOMe | F | Cl | H | 92.4–93.4 |
| 629 | cPr | SO2Me | F | Cl | H | 136–138.2 |
| 630 | cPr | SnPr | H | CF3 | H | 72.2–74.2 |
| 631 | cPr | SMe | Me | Me | H | 134–136 |
| 632 | cPr | SO2nPr | H | CF3 | H | 119.8–121.6 |
| 633 | cPr | SO2Me | OMe | Cl | H | 122–123 |
| 634 | cPr | SMe | Cl | Br | H | 137–139 |
| 635 | cPr | SOMe | Cl | Br | H | 156–158 |
| 636 | cPr | SO2Me | Cl | Br | H | 156–158 |
| 637 | tBu | Cl | H | SO2Me | H | 144 |
| 638 | cPr | Cl | H | SO2Me | H | 145 |
| 639 | cPr | CF3 | H | SO2Me | H | 139 |
| 640 | Et | Cl | H | SO2Me | H | 128 |
| 641 | sBu | Cl | H | SO2Me | H | 110 |
| 642 | nPr | Cl | H | SO2Me | H | 90 |
| 643 | tBu | CF3 | H | SO2Me | H | 123 |
| 644 | 1-Me-cPr | CF3 | H | SO2Me | H | 131 |
| 645 | Me | CF3 | H | SO2Me | H | 150 |
| 646 | cPr | Cl | H | SMe | H | 90.5 |
| 647 | cPr | F | H | SO2Me | H | 142 |
| 648 | cPr | Cl | H | SO2Et | H | 142 |
| 649 | cPr | CF3 | H | CF3 | H | Gum |
| 650 | cPr | CF3 | H | SOMe | H | Oil |
| 651 | cPr | OMe | H | SMe | H | 108–109 |
| 652 | Me | Br | OMe | SO2Me | H | 111 |

-continued

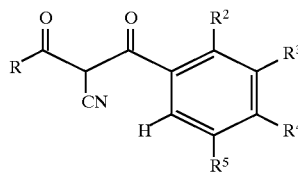

| Cpd No. | R | $R^2$ | $R^3$ | $R^4$ | $R^5$ | mp(°C.) |
|---|---|---|---|---|---|---|
| 653 | 1-Me-cPr | Cl | Cl | SO2Me | H | 179.5 |
| 654 | cPr | Cl | OMe | SO2Me | H | 147.5 |
| 655 | Me | Cl | OMe | SO2Me | H | 123 |
| 656 | cPr | Br | H | SO2Me | H | 165 |
| 657 | 1-Me-cPr | Br | H | SO2Me | H | 146 |
| 658 | 1-Me-cPr | CF3 | H | SO2Et | H | Glass |
| 659 | 1-Me-cPr | Cl | OMe | SO2Me | H | 127 |
| 660 | cPr | Cl | H | SOMe | H | 119.5 |
| 661 | cPr | Br | OMe | SMe | H | 128–129 |
| 662 | cPr | Br | OMe | SOMe | H | 185.5–187.5 |
| 663 | cPr | Br | OMe | SO2Me | H | 135.5–137.5 |
| 664 | tBu | Cl | H | SMe | H | 97–99 |
| 665 | cPr | H | SMe | Me | H | 64.7–67.9 |
| 666 | cPr | H | SO2Me | Me | H | 133.6–135.6 |
| 667 | cPr | H | SOMe | Me | H | 104.3 |

Note:
cPr = Cyclopropyl. Also, in compounds 1 through 589 and 611 through 667, subscripts have not been used, but are understood, e.g. SO2NMe2 means —SO$_2$N(CH$_3$)$_2$; SO2N(Me)CH3CH3CH3 means —SO$_2$N(CH$_3$)CH$_2$CH$_3$; OC(Cl)=Cl2 means —OC(Cl)=CCl$_2$; CH2S(Ph-3,4-Cl2) means —CH$_2$S-(3,4-dichlorophenyl); etc.

The numbers 1 to 667 are assigned to these compounds for reference and identification hereafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) may be prepared from a compound of formula (II):

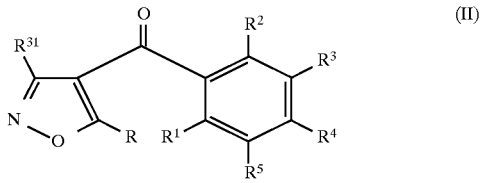

wherein R, $R^1$, $R^2$, $R^3$, $R^4$ and $R^5$ are as hereinbefore defined and $R^{31}$ represents the hydrogen atom or a group selected from a carboxylic ester, amide, nitrile and acyl.

Where $R^{31}$ represents hydrogen or an acyl group the reaction is carried out by treatment with a base. Examples of suitable bases include alkali or alkaline earth metal hydroxides or alkoxides such as sodium ethoxide or organic bases such as triethylamine.

Where $R^{31}$ represents a group such as an ester, amide or nitrile the conversion is carried out by a hydrolytic reaction. The hydrolytic reaction may be carried out in the presence of an acid or base. Acidic hydrolysis may be achieved for example using aqueous hydrochloric acid. Basic hydrolysis may be achieved for example using sodium hydroxide in a mixture of alcohol and water. The reactions are carried out at a temperature between room temperature and the reflux temperature of the mixture.

According to a further feature of the present invention compounds of formula (I) may be prepared from a compound of formula (III):

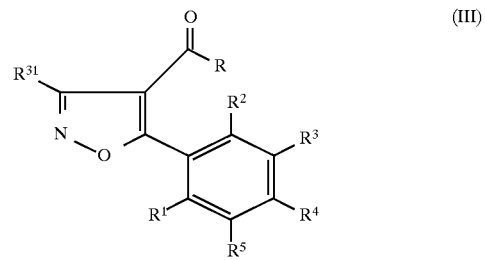

wherein R, $R^1$, $R^2$, $R^3$, $R^4$, $R^5$ and $R^{31}$ are as hereinbefore defined.

Where $R^{31}$ represents hydrogen or an acyl group the reaction is carried out by treatment with a base. Examples of suitable bases include alkali or alkaline earth metal hydroxides or alkoxides such as sodium ethoxide or organic bases such as triethylamine.

Where $R^{31}$ represents a group such as an ester, amide or nitrile the conversion is carried out by a hydrolytic reaction. The hydrolytic reaction may be carried out in the presence of an acid or base. Acidic hydrolysis may be achieved for example using aqueous hydrochloric acid. Basic hydrolysis may be achieved for example using sodium hydroxide in a mixture of alcohol and water. The reactions are carried out at a temperature between room temperature and the reflux temperature of the mixture.

According to a further feature of the present invention, compounds of formula (I) may also be prepared by the reaction of a benzoyl chloride of formula (IV):

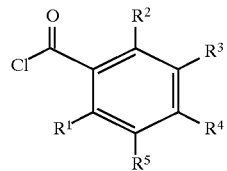

wherein $R^1$, $R^2$, $R^3$, $R^4$ and $R^5$ are as hereinbefore defined, with a beta-ketonitrile of formula (V):

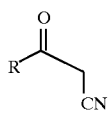

wherein R is as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

According to a further feature of the present invention, compounds of formula (I) may also be prepared by the reaction of an acid chloride of formula (VI):

wherein R is as hereinbefore defined, with a beta-ketonitrile of formula (VII):

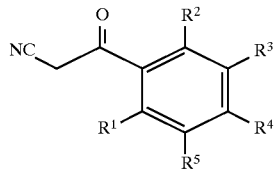

wherein $R^1$, $R^2$, $R^3$, $R^4$ and $R^5$ are as hereinbefore defined. The reaction is generally performed in the presence of a base in a solvent or solvent mixture. Suitable bases include metal hydrides, hydroxides or alkoxides (e.g. sodium or lithium hydride, sodium hydroxide, potassium hydroxide, magnesium ethoxide or magnesium methoxide). Suitable solvents include for example tetrahydrofuran; hydrocarbons such as toluene; or halogenated hydrocarbons such as dichloromethane. The reaction is generally performed at a temperature from 0° C. to reflux temperature.

According to a further feature of the present invention compounds of formula (I) may be prepared by the reaction of a benzoyl chloride of formula (IV) wherein $R^1$, $R^2$, $R^3$, $R^4$ and $R^5$ are as hereinbefore defined, with a beta-ketonitrile of formula (V) wherein R is as hereinbefore defined, via an intermediate of formula (VIII):

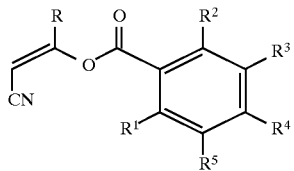

wherein R, $R^1$, $R^2$, $R^3$, $R^4$ and $R^5$ are as hereinbefore defined. The formation of the intermediate of formula (VIII) may be carried out in the presence of a mild base such as an organic base e.g. triethylamine, in an inert solvent such as acetonitrile or dichloromethane at a temperature between room temperature and the reflux temperature of the mixture. The rearrangement of the intermediate of formula (VIII) to a compound of formula (I) may be carried out optionally in situ in an inert solvent such as acetonitrile or dichloromethane in the presence of a catalyst such as a source of cyanide. Examples of such sources of cyanide are acetone cyanohydrin or an alkali metal cyanide such as potassium cyanide, optionally in the presence of a crown ether such as 18-crown-6.

According to a further feature of the present invention compounds of formula (I) may be prepared by the reaction of an acid chloride of formula (VI) wherein R is as hereinbefore defined, with a beta-ketonitrile of formula (VII) wherein $R^1$, $R^2$, $R^3$, $R^4$ and $R^5$ are as hereinbefore defined, via an intermediate of formula (IX):

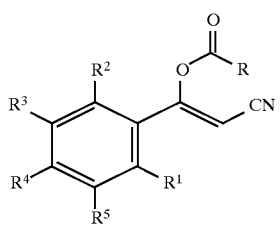

wherein R, $R^1$, $R^2$, $R^3$, $R^4$ and $R^5$ are as hereinbefore defined. The formation of the intermediate of formula (IX) may be carried out in the presence of a mild base such as an organic base e.g. triethylamine, in an inert solvent such as acetonitrile or dichloromethane at a temperature between room temperature and the reflux temperature of the mixture. The rearrangement of the intermediate of formula (IX) to a compound of formula (I) may be carried out optionally in situ in an inert solvent such as acetonitrile or dichloromethane in the presence of a catalyst such as a source of cyanide. Examples of such sources of cyanide are acetone cyanohydrin or an alkali metal cyanide such as potassium cyanide, optionally in the presence of a crown ether such as 18-crown-6.

Intermediates in the preparation of compounds of formula (I) may be prepared by the application or adaptation of known methods.

Compounds of formula (II) or (III) in which $R^{31}$ represents hydrogen may be prepared by the reaction of a compound of formula (X):

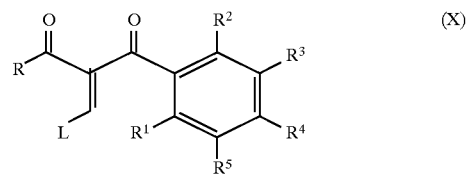

wherein $R^1$, $R^2$, $R^3$, $R^4$ and $R^5$ are as hereinbefore defined and L is —$OR^{72}$ or —$N(R^{72})_2$ and $R^{72}$ is an alkyl group, with a salt of hydroxylamine in the presence of a base or acid acceptor. The reaction is generally carried out using hydroxylamine hydrochloride in the presence of sodium acetate or an organic base such as triethylamine. The reaction is preferably performed in a solvent. Suitable solvents include alcohols such as ethanol or inert solvents such as acetonitrile. The reaction is carried out at a temperature between room temperature and the boiling point of the solvent.

Compounds of formula (X) in which L represents —OR$^{72}$ may be prepared by the reaction of a diketone of formula (XI):

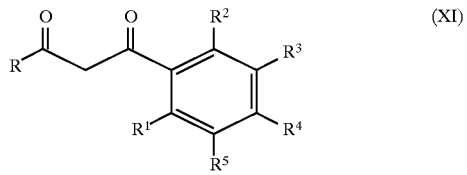

wherein R, R$^1$, R$^2$, R$^3$, R$^4$ and R$^5$ are as hereinbefore defined, with an ortho ester, HC(OR$^{72}$)$_3$. The reaction is generally carried out using triethyl orthoformate in the presence of an acid catalyst such as acetic anhydride. The reaction is carried out at a temperature between room temperature and the boiling point of the mixture.

Compounds of formula (X) in which L represents —N(R$^{72}$)$_2$ may be prepared by the reaction of a diketone of formula (XI) with an amide acetal of formula (R$^{72}$)$_2$N—CH(OR$^{72}$)$_2$. The reaction is optionally carried out in an inert solvent such as toluene at a temperature between room temperature and the boiling point of the mixture.

Compounds of formula (II) wherein R$^{31}$ represents an ester, nitrile or acyl group may be prepared by the reaction of a compound of formula (XII):

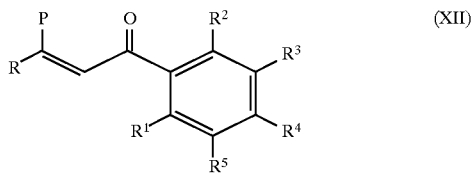

wherein R, R$^1$, R$^2$, R$^3$, R$^4$ and R$^5$ are as hereinbefore defined and P is a leaving group such as N,N-dialkylamino, with a compound of formula R$^{31}$—C(Z)=NOH wherein R$^{31}$ represents an ester, nitrile or acyl group and Z is a halogen atom. Generally Z is a chlorine or bromine atom. The reaction is generally performed in an inert solvent such as toluene or dichloromethane either in the presence of a base such as triethylamine or a catalyst such as a 4 Angstrom molecular sieve or fluoride ion.

Compounds of formula (XII) may be prepared by the reaction of a compound of formula CH$_2$=C(R$^{31}$)(P), wherein R$^{31}$ and P are as hereinbefore defined, with a benzoyl chloride of formula (IV). The reaction is generally carried out in the presence of an organic base such as triethylamine in an inert solvent such as toluene or dichloromethane at a temperature between –20° C. and room temperature.

Compounds of formula (II) or (III) wherein R$^{31}$ represents an ester, nitrile or acyl group may be prepared by the reaction of a compound of formula (XI) with a compound of formula R$^{31}$—C(Z)=NOH wherein R$^{31}$ represents an ester, nitrile or acyl group and Z is as hereinbefore defined. Generally Z is a chlorine or bromine atom. The reaction is generally performed in an inert solvent such as dichloromethane or acetonitrile in the presence of a base.

Examples of suitable bases are alkaline earth metal alkoxides such as magnesium methoxide and the reaction is carried out a temperature between room temperature and the reflux temperature of the mixture.

Compounds of formula (II) or (III) wherein R$^{31}$ represents an amide group may be prepared by the reaction of the corresponding compound of formula (II) or (III) in which R$^{31}$ represents an ester group with ammonia or an amine. The reaction is carried out in a solvent or solvent mixture such as aqueous ethanol at a temperature between room temperature and the reflux temperature of the mixture.

Compounds of formula (III) in which R$^{31}$ represents hydrogen may be prepared by the reaction of a compound of formula (XIII):

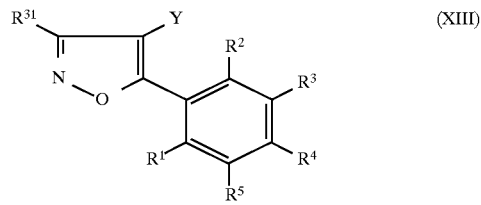

in which R$^{31}$ represents hydrogen and Y represents a carboxy group, or a reactive derivative thereof (such as a carboxylic acid chloride or carboxylic ester) or a cyano group, with an appropriate organometallic reagent such as a Grignard reagent or an organolithium reagent, to introduce the group —COR into the 4-position of the isoxazole ring. The reaction is generally carried out in an inert solvent such as ether or tetrahydrofuran, at a temperature from 0° C. to the reflux temperature of the solvent.

Compounds of formula (III) in which R$^{31}$ is an ester, nitrile or acyl group may be prepared by the reaction of a compound of formula (XIV):

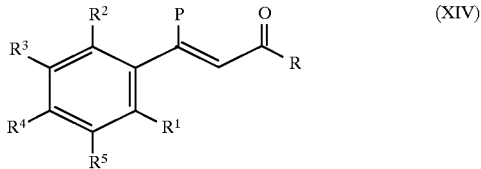

wherein P is a leaving group such as N,N-dialkylamine with a compound of formula R$^{31}$C(Z)=N—OH wherein Z is as hereinbefore defined and R$^{31}$ is an ester, nitrile or acyl group. Generally Z is chlorine or bromine. The reaction is generally performed in an inert solvent such as toluene or dichloromethane either in the presence of a base such as triethylamine or a catalyst such as a 4A molecular sieve or fluoride ion.

Compounds of formula (XIII) in which R$^{31}$ is a hydrogen atom and Y is —CO$_2$-alkyl or —CN may be prepared by the reaction of a compound of formula (XV):

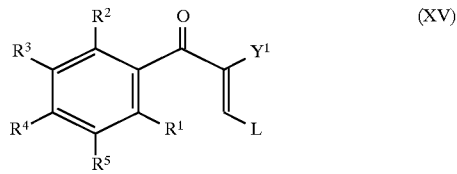

wherein Y$^1$ represents CO$_2$-alkyl or —CN and L is as hereinbefore described, with a salt of hydroxylamine such as hydroxylame hydrochloride, in a solvent such as ethanol or acetonitrile, optionally in the presence of a base or acid acceptor such as triethylamine or sodium acetate.

Compounds of formula (XIII) in which R$^{31}$ represents hydrogen and Y represents a carboxylic acid or carboxylic acid chloride may be prepared from the corresponding compound of formula (XIII) in which $R^{31}$ represents hydrogen and Y represents a carboxylic ester group by the hydrolysis of said ester group and conversion, as necessary, of the acid thus obtained to the acid chloride, e.g. by heating with thionyl chloride.

Compounds of formula (XV) may be prepared by the reaction of a compound of formula (VII) or a ketoester of formula (XVI):

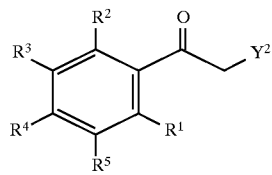

wherein $R^1$, $R^2$, $R^3$, $R^4$ and $R^5$ are as hereinbefore defined and $Y^2$ represents —$CO_2$-alkyl, with either triethyl orthoformate in the presence of acetic anhydride at the reflux temperature of the mixture or with dimethylformamide dimethylacetal optionally in an inert solvent such as toluene at a temperature from room temperature to the reflux temperature of the mixture.

Compounds of formula (XIV) may be prepared by the reaction of a compound of formula (XVII):

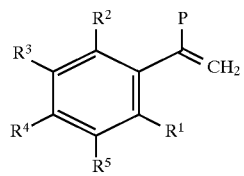

wherein $R^1$, $R^2$, $R^3$, $R^4$, $R^5$ and P is as hereinbefore defined, with an acid chloride of formula (VI) wherein R is as hereinbefore defined, in an inert solvent such as dichloromethane or toluene, in the presence of a base such as triethylamine.

Acid chlorides of formula (IV) or (VI) are generally known or can be prepared from the corresponding carboxylic acid according to commonly accepted methods, for example by using thionyl chloride in chloroform at reflux.

Beta-ketonitriles of formula (V) may be prepared from acid chlorides of formula (VI) by a number of methods well known in the chemical literature. For example, see Krauss, et al, Synthesis, 1983, 308, or Muth, et al, J. Org. Chem, 1960, 25, 736. Alternatively beta-ketonitriles of formula (V) may be prepared by the reaction of an ester of formula R—$CO_2$Et, wherein R is as hereinbefore defined, with acetonitrile. This reaction is described in the literature for example see the article by Abramovitch and Hauser, J. Am. Chem. Soc., 1942, 64, 2720.

Beta-ketonitriles of formula (VII) may be prepared from benzoyl chlorides of formula (IV) or from ethyl benzoates of formula (XVIII):

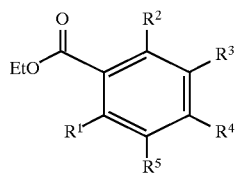

wherein $R^1$, $R^2$, $R^3$, $R^4$ and $R^5$ are as hereinbefore defined, in a manner analogous to the preparation of beta-ketonitriles of formula (V) set forth above.

Compounds of formula (V), (XI), (XIV), (XVI), (XVII) and (XVIII) are known or may be prepared by the application and adaptation of known methods.

Agriculturally acceptable salts and metal complexes of compounds of formula (I) may be prepared by known methods.

The following examples illustrate the preparation of compounds of general formula (I). In the present specification b.p. means boiling point, m.p. means melting point. Where the letters NMR appear, the characteristics of the proton nuclear magnetic resonance spectrum follow. Unless otherwise specified the percentages are by weight.

EXAMPLE 1

Sodium metal (0.11 g) was dissolved in absolute ethanol with stirring and was cooled to ambient temperature. 4-(2-Cyclohexylsulphonyl-4-trifluoromethybenzoyl)-5-cyclopropylisoxazole (1.5 g) in absolute ethanol was added and the resulting solution was stirred at ambient temperature for 3 hours. It was poured into ice/water, acidified to pH1 with concentrated hydrochloric acid and the resultant white suspension was allowed to warm to ambient temperature before it was extracted with ethyl acetate. The combined organic extracts were washed with water and dried (magnesium sulphate). Evaporation of the solvent gave a light-brown solid (1.3 g) of 2-cyano-1-(2-cyclohexylsulphonyl-4-trifluoromethylphenyl)-3-cyclopropylpropan-1,3-dione (compound 517) m.p. 60°–62° C.

By proceeding in a similar manner the following compounds of formula (I) were prepared from the appropriately substituted starting materials.

| Cpd No | R | $R^1$ | $R^2$ | $R^3$ | $R^4$ | $R^5$ | mp (°C.) or NMR |
|---|---|---|---|---|---|---|---|
| 13 | cPr | H | N(Me)$SO_2$Me | H | $NO_2$ | H | 203–205 |
| 64 | cPr | H | Cl | H | N(Me)$SO_2$Me | H | 115.8–116.6 |
| 76 | cPr | H | $NO_2$ | H | N(Me)$SO_2$Me | H | 133–134 |
| 310 | cPr | H | $SO_2$Ph | H | $CF_3$ | H | 153.5 |
| 311 | cPr | H | SPh | H | $CF_3$ | H | 77.5 |
| 516 | cPr | H | S-cHex | H | $CF_3$ | H | a |

Note:
cPr represents cyclopropyl
cHex represents cyclohexyl
a NMR (CDCl$_3$): 1.15(m, 9H), 1.55(m, 1H), 1.7(m, 2H), 1.9(m, 2H), 2.3(m, 1H), 3.15(m, 1H), 7.5(m, 2H), 7.7(s, 1H), 17.25(bs, 1H).

EXAMPLE 2

4-(2-Methylsulphonylmethyl-4-bromobenzoyl)-5-cyclopropylisoxazole (0.3 g) in dichloromethane was treated at ambient temperature with triethylamine (0.124 ml) and the reaction mixture was stirred at ambient temperature for 3.33 hours. It was treated with 2M hydrochloric acid, diluted with dichloromethane and brine, extracted with more dichloromethane and dried (sodium sulphate). Evaporation of solvent gave a beige gum (0.3 g). This was triturated with diisopropyl ether to give 2-cyano-3-cyclopropyl-1-(2-methylsulphonylmethyl-4-bromophenyl)-propan-1,3-dione, (compound 152) as a white solid (0.24 g), m.p. 108° C.

By proceeding in a similar manner the following compounds of formula (I) were prepared from the appropriately substituted starting materials.

| Cpd No. | R | $R^1$ | $R^2$ | $R^3$ | $R^4$ | $R^5$ | m.p. (°C.) |
|---|---|---|---|---|---|---|---|
| 1 | cPr | H | Cl | H | $SO_2NMe_2$ | H | 124.5–126 |
| 2 | cPr | H | $CF_3$ | H | $SO_2NMe_2$ | H | 147–153.8 |
| 30 | cPr | H | $N(Me)SO_2Me$ | H | Cl | H | 127.8–128.5 |
| 61 | cPr | H | $N(Me)SO_2Me$ | H | Me | H | 106–108 |
| 85 | cPr | H | CL | H | $NHSO_2Me$ | H | 146–152 |
| 109 | cPr | H | $N(Et)SO_2Me$ | H | Cl | H | 120–122 |
| 384 | cPr | H | $OSO_2Me$ | H | H | H | 103.9–105.5 |
| 385 | cPr | H | $OSO_2Me$ | H | Cl | H | 140–140.6° C. |
| 393 | cPr | H | $OSO_2Me$ | H | H | Cl | 131.1–133.3 |
| 422 | cPr | H | $OSO_2Et$ | H | H | H | 54–58 |
| 436 | cPr | H | $OSO_2NMe_2$ | H | H | H | 134–136.4 |
|  | cPr | H | Cl | | $CH_2SMe$ | H | (a) |

Note:
cPr represents cyclopropyl.

(a) NMR ($CDCl_3$): 1.2(2H,M), 1.4(2H,m), 1.95(3H,s), 2.3(1H,m), 3.6(2H,s), 7.3(1H,dd), 7.4(2H,m), 17.4(1H,brs).

EXAMPLE 3

[Alpha-(cyanomethylene)-4-chloro-2-(methylsulphenyl) benzyl]3,5-bis(trifluoromethyl)benzoate (0.9 g) in acetonitrile was treated with potassium cyanide (0.038 g), triethylamine (0.37 ml) and 18-crown-6 (0.005 g) at room temperature. The reaction mixture was stirred for 22 hours. After evaporating the solvent, the residue was dissolved in dichloromethane and washed with hydrochloric acid (2M) and water. The organic extract was dried (magnesium sulphate), filtered and evaporated to give 3-[3,5-bis (trifluoromethyl)phenyl]-2-cyano-1-[4-chloro-2-methylsulphenylphenyl]-propan-1,3-dione (compound 337, 0.85 g) m.p. 146°–149° C.

EXAMPLE 4

Cyanoacetic acid (8.5 g) was dissolved in dry tetrahydrofuran (THF) (250 ml), placed under an inert atmosphere and the solution was cooled using a dry ice-acetone bath. Butyl lithium (80 ml of a 2.5M solution in hexane) was added dropwise over 1 hour. During the addition the internal reaction temperature was maintained below –65° C. The reaction mixture was stirred in the dry ice-acetone bath for 1 hour, the cooling bath removed, and the reaction stirred for an additional hour during which time the internal temperature rose to 15° C. The resultant reaction mixture was cooled to –70° C. and cyclopropanecarbonyl chloride (5.2 g) in THF (50 ml) added dropwise over 20 minutes, while keeping the temperature of the reaction mixture below –65° C. The reaction mixture was thus stirred for 1 hour and then allowed to warm to room temperature overnight. The resultant mixture was acidified by the addition of 2N HCl (200 ml) and then diluted with $CH_2Cl_2$ (500 ml). The layers were separated and the aqueous layer was extracted with $CH_2Cl_2$. The combined organic layers were dried, filtered; the solvents were removed to give 7.5 g of an orange oil. The crude is product was chromatographed on silica gel to afford 4.0 g of 3-cyclopropyl-3-oxopropanonitrile as a pale orange oil, $^1$H-NMR ($CDCl_3$): d 0.9–1.3 (m, 4H), 1.9–2.1 (m, 1H), 3.66 (s, 2H).

To a mixture of absolute ethanol (7 ml) and $CCl_4$ (1 ml) under an inert atmosphere and at room temperature was added magnesium turnings (0.13 g). The reaction mixture was stirred. To the reaction mixture was added 3-cyclopropyl-3-oxopropanonitrile (0.54 g) in absolute ethanol (3 ml) and the resultant suspension progressively warmed during 30 minutes. The resultant yellow solution was evaporated to dryness. The solid was suspended in dry toluene (15 ml) and the resulting mixture warmed to 50° C. A solution of 2-(methylsulphonyl)benzoyl chloride in dry toluene (5 ml) was added. The resultant reaction mixture was stirred at 50° C. for 30 minutes, heated to reflux for 1 hour, cooled to room temperature, and allowed to sit overnight. To the reaction mixture was added 6N HCl (50 ml) and the two layers stirred vigorously until all the solid had dissolved. The layers were separated and the aqueous layer was extracted with ether. The organic extracts were combined with the organic layer and extracted with saturated $NaHCO_3$ solution. The basic extracts were acidified to pH 5 by the addition of concentrated HCl. The resulting mixture was extracted with ether. The ethereal extracts were combined, washed with water, dried, filtered, and evaporated; 0.5 g of a sticky red gum was obtained. This material was chromatographed on silica gel to afford 0.10 g of 2-cyano-3-cyclopropyl-1-[2-(methylsulphonyl)phenyl] propan-1,3-dione, COMPOUND 611, as a light orange solid, m.p. 155° C.

The compounds listed below may be prepared in manner similar to the method described above.

COMPOUND 612: 1-[4-chloro-2-(methylsulphonyl) phenyl]-2-cyano-3-cyclopropylpropan-1,3-dione, m.p. 116° C., starting from 3-cyclopropyl-3-oxopropanonitrile and 4-chloro-2-(methylsulphonyl)-benzoyl chloride.

COMPOUND 613: 2-cyano-1-cyclopropyl-3-[2-(ethylsulphonyl)phenyl]propan-1,3-dione, m.p. 169° C., starting from 3-cyclopropyl-3-oxopropanonitrile and 2-(ethylsulphonyl)benzoyl chloride.

COMPOUND 614: 2-cyano-1-cyclopropyl-3-[2-(1-methylethylsulphonyl)phenyl]propan-1,3-dione, m.p. 189° C., starting from 3-cyclopropyl-3-oxopropanonitrile and 2-(1-methylethylsulphonyl)benzoyl chloride.

EXAMPLE 5

A suspension of 4-[4-chloro-2-(methylsulphonyl) benzoyl]-5-cyclopropylisoxazole (2.2 g) in ethanol was added to a solution of sodium ethoxide in ethanol (prepared from sodium (0.2 g) and ethanol). The mixture was stirred at room temperature for 2 hours then poured into water and acidified to pH 1. It was extracted with ethyl acetate, washed with water, dried ($MgSO_4$) and filtered. The filtrate was evaporated to dryness and the residue was recrystallised from ethyl acetate and cyclohexane to give 1-[4-chloro-2-(methylsulphonyl)phenyl]-2-cyano-3-cyclopropylpropan-1, 3-dione, COMPOUND 612, (1.7 g) as a light brown solid, m.p. 116° C.

By proceeding in a similar manner the following compounds of formula I were prepared from the appropriately substituted starting materials.

COMPOUND 611: 2-cyano-3-cyclopropyl-1-[2-(methylsulphonyl)phenyl]propan-1,3-dione, m.p. 155° C., starting from 5-cyclopropyl-4-[2-(methylsulphonyl) benzoyl]isoxazole.

COMPOUND 613: 2-cyano-1-cyclopropyl-3-[2-(ethylsulphonyl)phenyl]propan-1,3-dione, m.p. 169° C., starting from 5-cyclopropyl-4-[2-(ethylsulphonyl)benzoyl] isoxazole.

COMPOUND 614: 2-cyano-1-cyclopropyl-3-[2-(1-methylethylsulphonyl)phenyl]propan-1,3-dione, m.p. 189° C., starting from 5-cyclopropyl-4-[2-(1-methylethylsulphonyl)benzoyl]isoxazole.

COMPOUND 615: 1-[4-chloro-2-(methylsulphonyl) phenyl]-2-cyano-3-(1-methylcyclopropyl)propan-1,3-dione, m.p. 122° C., starting from 4-[4-chloro-2-(methylsulphonyl)benzoyl]-5-(1-methylcyclopropyl)isoxazole.

COMPOUND 616: 1-[4-chloro-2-(methylsulphonyl)phenyl]-2-cyano-4-methylpentan-1,3-dione, m.p. 115.5° C., starting from 4-[4-chloro-2-(methylsulphonyl)benzoyl]-5-(1-methylethyl)isoxazole.

COMPOUND 617: 2-cyano-3-cyclopropyl-1-[4-methyl-2-(methylsulphonyl)phenyl]propan-1,3-dione, m.p. 129.5° C., starting from 5-cyclopropyl-4-[4-methyl-2-(methylsulphonyl)-benzoyl]isoxazole.

COMPOUND 618: 2-cyano-3-cyclopropyl-1-[4-methoxy-2-(methylsulphonyl)phenyl]propan-1,3-dione, m.p. 151.5° C., starting from 5-cyclopropyl-4-[4-methoxy-2-(methylsulphonyl)-benzoyl]isoxazole.

COMPOUND 619: 1-[4-chloro-2-(methylsulphenyl)phenyl]-2-cyano-3-cyclopropylpropan-1,3-dione, m.p. 154.5° C., starting from 4-[4-chloro-2-(methylsulphenyl)benzoyl]-5-cyclopropylisoxazole.

COMPOUND 620: 1-[4-bromo-2-(methylsulphonyl)phenyl]-2-cyano-3-cyclopropylpropan-1,3-dione, m.p. 159° C., starting from 4-[4-bromo-2-(methylsulphonyl)benzoyl]-5-cyclopropylisoxazole.

COMPOUND 621: 2-cyano-3-cyclopropyl-1-[2-(methylsulphonyl)-4-trifluoromethylphenyl]propan-1,3-dione, m.p. 107.5° C., starting from 5-cyclopropyl-4-[2-(methylsulphonyl)-4-trifluoromethylbenzoyl]isoxazole.

COMPOUND 622: 2-cyano-3-cyclopropyl-1-(3,4-dichloro-2-methylsulphenylphenyl)propan-1,3-dione, m.p. 110°–112° C., starting from 5-cyclopropyl-4-(3,4-dichloro-2-methylsulphenylbenzoyl)isoxazole.

COMPOUND 625: 2-cyano-3-cyclopropyl-1-[2-(1-methylpropylsulphonyl)-4-trifluoromethylphenyl]propan-1,3-dione, m.p. 115°–117° C., starting from 5-cyclopropyl-4-[2-(1-methylpropylsulphonyl)-4-trifluoromethylbenzoyl]isoxazole.

COMPOUND 626: 2-cyano-3-cyclopropyl-1-[2-(1-methylpropylsulphenyl)-4-trifluoromethylphenyl]propan-1,3-dione, as a brown gum, NMR (CDCl$_3$) 0.9(3H,t), 1.2(5H,m), 1.4(2H,m), 1.5(2H,m), 2.3(1H,m), 3.2(1H,m), 7.5(2H,m), 7.7(1H,s), starting from 5-cyclopropyl-4-[2-(1-methylpropylsulphenyl)-4-trifluoromethylbenzoyl]isoxazole.

COMPOUND 627: 1-(4-chloro-3-fluoro-2-methylsulphenylphenyl)-2-cyano-3-cyclopropylpropan-1,3-dione, m.p. 121.2°–122.60° C., starting from 4-(4-chloro-3-fluoro-2-methylsulphenylbenzoyl)-5-cyclopropylisoxazole.

COMPOUND 628: 1-(4-chloro-3-fluoro-2-methylsulphinylphenyl)-2-cyano-3-cyclopropylpropan-1,3-dione, m.p. 92.4°–93.40° C., starting from 4-(4-chloro-3-fluoro-2-methylsulphinylbenzoyl)-5-cyclopropylisoxazole.

COMPOUND 629: 1-(4-chloro-3-fluoro-2-methylsulphonylphenyl)-2-cyano-3-cyclopropylpropan-1,3-dione, m.p. 136°–138.2° C., starting from 4-(4-chloro-3-fluoro-2-methylsulphonylbenzoyl)-5-cyclopropylisoxazole.

COMPOUND 633: 1-(4-chloro-3-methoxy-2-methylsulphonylphenyl)-2-cyano-3-cyclopropylpropan-1,3-dione, m.p. 122°–123° C., starting from 4-(4-chloro-3-methoxy-2-methylsulphonylbenzoyl)-5-cyclopropylisoxazole.

EXAMPLE 6

Triethylamine (0.5 ml) was added to 5-cyclopropyl-4-(3,4-dichloro-2-methylsulphonylbenzoyl)isoxazole (1.0 g) in dichloromethane. The mixture was stirred at room temperature for 2.5 hours and evaporated to dryness. The residue was suspended in hydrochloric acid (2M) and was extracted with dichloromethane. The organic layer was washed with water, dried (Na$_2$SO$_4$) and filtered. The filtrate was evaporated to dryness to give 2-cyano-3-cyclopropyl-1-(3,4-dichloro-2-methylsulphonylphenyl)propan-1,3-dione (COMPOUND 623) as a white solid, m.p. 88°–90° C.[45]

By proceeding in a similar manner the following compounds of formula I were prepared:

COMPOUND 624: 2-cyano-3-cyclopropyl-1-(3,4-dichloro-2-methylsulphinylphenyl)propan-1,3-dione, m.p. 145.1°–146.7° C., starting from 5-cyclopropyl-4-(3,4-dichloro-2-methylsulphinylbenzoyl)isoxazole.

COMPOUND 630: 2-cyano-3-cyclopropyl-1-[2-(n-propylsulphenyl)-4-trifluoromethylphenyl]propan-1,3-dione, m.p. 72.2°–74.2° C., starting from 5-cyclopropyl-4-[2-(n-propylsulphenyl)-4-trifluoromethylbenzoyl]isoxazole.

COMPOUND 631: 2-cyano-3-cyclopropyl-1-(3,4-dimethyl-2-methylsulphenylphenyl)propan-1,3-dione, m.p. 134°–136° C., starting from 5-cyclopropyl-4-(3,4-dimethyl-2-methylsulphenylbenzoyl)isoxazole.

COMPOUND 632: 2-cyano-3-cyclopropyl-1-[2-(n-propylsulphonyl)-4-trifluoromethylphenyl]propan-1,3-dione, m.p. 119.8°–121.6° C., starting from 5-cyclopropyl-4-[2-(n-propylsulphonyl)-4-trifluoromethylbenzoyl]isoxazole.

COMPOUND 634: 1-(4-bromo-3-chloro-2-methylsulphenylphenyl)-2-cyano-3-cyclopropylpropan-1,3-dione, m.p. 137°–139° C., starting from 4-(4-bromo-3-chloro-2-methylsulphenylbenzoyl)-5-cyclopropylisoxazole.

COMPOUND 635: 1-(4-bromo-3-chloro-2-methylsulphinylphenyl)-2-cyano-3-cyclopropylpropan-1,3-dione, m.p. 156°–158° C., starting from 4-(4-bromo-3-chloro-2-methylsulphinylbenzoyl)-5-cyclopropylisoxazole.

COMPOUND 636: 1-(4-bromo-3-chloro-2-methylsulphonylphenyl)-2-cyano-3-cyclopropylpropan-1,3-dione, m.p. 156°–158° C., starting from 4-(4-bromo-3-chloro-2-methylsulphonylbenzoyl)-5-cyclopropylisoxazole.

EXAMPLE 7

To a mixture of absolute ethanol (10 ml) and carbon tetrachloride (1 ml) under an inert atmosphere and at room temperature was added magnesium turnings (0.2 g). The reaction mixture was stirred; almost immediately a reaction started (effervescence observed). To the reaction mixture was added 4,4-dimethyl-3-oxopentanonitrile (1 g) in absolute ethanol (4 ml) and the resulting suspension gently warmed until all the magnesium had reacted (approximately 30 min.). The resultant yellow solution was evaporated to dryness, dry toluene (30 ml) was added and the solvents evaporated. The solid was suspended in dry toluene (20 ml) and the resulting mixture warmed to 50° C. A slurry of 2-chloro-4-(methylsulphonyl)benzoyl chloride in dry toluene (10 ml) was added. The reaction mixture was heated at reflux for 1 hour, cooled to room temperature and allowed to sit overnight. To the reaction mixture was added 6N HCl (70 ml) and the two layers stirred vigorously until all the solid had dissolved. The layers were separated and the aqueous layer was extracted with ether (twice with 30 ml portions). The organic extracts were combined with the organic layer and extracted with saturated sodium hydrogen carbonate solution (three times with 50 ml portions). The basic extracts were acidified to pH 6 by the careful addition of concentrated HCl and the resultant solution was extracted with ether. The ethereal extracts were combined, washed with water and dried (magnesium sulphate). After removal of the drying agent by filtration, evaporation of the solvents afforded 0.85 g of a light brown solid. This material was suspended in boiling cyclohexane and enough ethyl acetate was added to dissolve the solid. After cooling to room temperature the precipitate was recovered by filtration and dried to afford 0.6 g of 1-[2-chloro-4-(methylsulphonyl)phenyl]-2-cyano-4,4-dimethylpentan-1,3-dione, COMPOUND 637, as a light brown solid, m.p. 144° C.

The compounds listed below may be prepared in manner similar to the method described above.

COMPOUND 638: 1-[2-chloro-4-(methylsulphonyl)phenyl]-2-cyano-3-cyclopropylpropan-1,3-dione, m.p. 145° C., starting from 3-cyclopropyl-3-oxopropanonitrile and 2-chloro-4-(methylsulphonyl)benzoyl chloride.

COMPOUND 639: 2-cyano-3-cyclopropyl-1-[4-(methylsulphonyl)-2-trifluoromethylphenyl]propan-1,3-dione, m.p. 139° C., starting from 3-cyclopropyl-3-oxopropanonitrile and 4-(methylsulphonyl)-2-trifluoromethylbenzoyl chloride.

COMPOUND 640: 1-[2-chloro-4-(methylsulphonyl)phenyl]-2-cyanopentan-1,3-dione, m.p. 128° C., starting from 3-oxopentanonitrile and 2-chloro-4-(methylsulphonyl)benzoyl chloride.

COMPOUND 641: 1-[2-chloro-4-(methylsulphonyl)phenyl]-2-cyano-4-methylhexan-1,3-dione, m.p. 110° C., starting from 3-oxo-4-methylhexanonitrile and 2-chloro-4-(methylsulphonyl)benzoyl chloride.

COMPOUND 642: 1-[2-chloro-4-(methylsulphonyl)phenyl]-2-cyanohexan-1,3-dione, m.p. 90° C., starting from 3-oxohexanonitrile and 2-chloro-4-(methylsulphonyl)benzoyl chloride.

COMPOUND 643: 2-cyano-4,4-dimethyl-1-[4-(methylsulphonyl)-2-trifluoromethylphenyl]pentan-1,3-dione, m.p. 123° C., starting from 4,4-dimethyl-3-oxopentanonitrile and 4-(methylsulphonyl)-2-trifluoromethylbenzoyl chloride.

COMPOUND 644: 2-cyano-1-[4-(methylsulphonyl)-2-trifluoromethylphenyl]-3-(1-methylcyclopropyl)propan-1,3-dione, m.p. 131° C., starting from 3-(1-methylcyclopropyl)-3-oxopropanonitrile and 4-(methylsulphonyl)-2-trifluoromethylbenzoyl chloride.

COMPOUND 645: 2-cyano-1-[4-(methylsulphonyl)-2-trifluoromethylphenyl]butan-1,3-dione, m.p.150° C., starting from 3-oxobutanonitrile and 4-(methylsulphonyl)-2-trifluoromethylbenzoyl chloride.

COMPOUND 646: 1-[2-chloro-4-(methylsulphenyl)phenyl]-2-cyano-3-cyclopropylpropan-1,3-dione, m.p. 90.5° C., starting from 3-cyclopropyl-3-oxopropanonitrile and 2-chloro-4-(methylsulphenyl)benzoyl chloride.

COMPOUND 647: 2-cyano-3-cyclopropyl-1-[2-fluoro-4-(methylsulphonyl)phenyl]propan-1,3-dione, m.p 142° C., starting from 3-cyclopropyl-3-oxopropanonitrile and 2-fluoro-4-(methylsulphonyl)benzoyl chloride.

COMPOUND 648: 1-[2-chloro-4-(ethylsulphonyl)phenyl]-2-cyano-3-cyclopropylpropan-1,3-dione, m.p. 142° C., starting from 3-cyclopropyl-3-oxopropanonitrile and 2-chloro-4-(ethylsulphonyl)benzoyl chloride.

COMPOUND 649: 2-cyano-3-cyclopropyl-1-[4-(methylsulphenyl)-2-trifluoromethylphenyl]propan-1,3-dione as a yellow gum, $^1$H NMR (CDCl$_3$): 1.2 (m,2H), 1.4 (m,2H), 2.3 (m,1H), 2.4 (s,3H), 7.3–7.6 (m,3H), starting from 3-cyclopropyl-3-oxopropanonitrile and 4-(methylsulphenyl)-2-trifluoromethyl benzoyl chloride.

EXAMPLE 8

5-Cyclopropyl-4-[2-methoxy-4-(methylsulphenyl)benzoyl]-isoxazole (1.0 g) was added to a solution of sodium ethoxide in ethanol (prepared from sodium (0.12 g) and ethanol). The mixture was stirred at room temperature for 2 hours, poured into water and acidified to pH 1 by addition of hydrochloric acid. The resultant suspension was extracted with ether, washed with water, dried (MgSO$_4$) and filtered. The filtrate was evaporated to dryness and the residue was triturated with ether and filtered to give 2-cyano-3-cyclopropyl-1-[2-methoxy-4-(methylsulphenyl)phenyl]propan-1,3-dione, COMPOUND 651, (0.88 g) as a cream solid, m.p. 108°–109° C.

By proceeding in a similar manner the following compounds were prepared from the appropriately substituted starting materials.

COMPOUND 638: 1-[2-chloro-4-(methylsulphonyl)phenyl]-2-cyano-3-cyclopropylpropan-1,3-dione, m.p. 145° C., starting from 4-[2-chloro-4-(methylsulphonyl)benzoyl]-5-cyclopropylisoxazole.

COMPOUND 639: 2-cyano-3-cyclopropyl-1-[4-(methylsulphonyl)-2-trifluoromethylphenyl]propan-1,3-dione, m.p. 139° C., starting from 5-cyclopropyl-4-[4-(methylsulphonyl)-2-trifluoromethylbenzoyl]isoxazole.

COMPOUND 640: 1-[2-chloro-4-(methylsulphonyl)phenyl]-2-cyanopentan-1,3-dione, m.p. 128° C., starting from 4-[2-chloro-4-(methylsulphonyl)benzoyl]-5-ethylisoxazole.

COMPOUND 641: 1-[2-chloro-4-(methylsulphonyl)phenyl]-2-cyano-4-methylhexan-1,3-dione, m.p. 110° C., starting from 4-[2-chloro-4-(methylsulphonyl)benzoyl]-5-(1-methylpropyl)isoxazole.

COMPOUND 642: 1-[2-chloro-4-(methylsulphonyl)phenyl]-2-cyanohexan-1,3-dione, m.p. 90° C., starting from 4-[2-chloro-4-(methylsulphonyl)benzoyl]-5-propylisoxazole.

COMPOUND 643: 2-cyano-4,4-dimethyl-1-[4-(methylsulphonyl)-2-trifluoromethylphenyl]pentan-1,3-dione, m.p. 123° C., starting from 5-(1,1-dimethylethyl)-4-[4-(methylsulphonyl)-2-trifluoromethylbenzoyl]isoxazole.

COMPOUND 644: 2-cyano-1-[4-(methylsulphonyl)-2-trifluoromethylphenyl]-3-(1-methylcyclopropyl)propan-1, 3-dione, m.p. 131° C., starting from 5-(1-methylcyclopropyl)-4-[4-(methylsulphonyl)-2-trifluoromethylbenzoyl]isoxazole.

COMPOUND 645: 2-cyano-1-[4-(methylsulphonyl)-2-trifluoromethylphenyl]butan-1,3-dione, m.p. 150° C., starting from 5-methyl-4-[4-(methylsulphonyl)-2-trifluoromethylbenzoyl]isoxazole.

COMPOUND 646: 1-[2-chloro-4-(methylsulphenyl)phenyl]-2-cyano-3-cyclopropylpropan-1,3-dione, m.p. 90.5° C., starting from 4-[2-chloro-4-(methylsulphenyl)benzoyl]-5-cyclopropylisoxazole.

COMPOUND 647: 2-cyano-3-cyclopropyl-1-[2-fluoro-4-(methylsulphonyl)phenyl]propan-1,3-dione, m.p. 142° C., starting from 5-cyclopropyl-4-[2-fluoro-4-(methylsulphonyl)benzoyl]isoxazole.

COMPOUND 648: 1-[2-chloro-4-(ethylsulphonyl)phenyl]-2-cyano-3-cyclopropylpropan-1,3-dione, m.p. 142° C., starting from 4-[2-chloro-4-(ethylsulphonyl)benzoyl]-5-cyclopropylisoxazole.

COMPOUND 649: 2-cyano-3-cyclopropyl-1-[4-(methylsulphenyl)-2-trifluoromethylphenyl]propan-1,3-dione as a yellow gum, $^1$H NMR(CDCl$_3$):d 1.2(m,2H),1.4 (m,2H), 2.3 (m,1H), 2.4(s,3H), 7.3–7.6(m,3H), starting from 5-cyclopropyl-4-[4-(methylsulphenyl)-2-trifluoromethylbenzoyl]isoxazole.

COMPOUND 650: 2-cyano-3-cyclopropyl-1-[4-(methylsulphinyl)-2-trifluoromethylphenyl)propan-1,3- dione, $^1$H NMR (CDCl$_3$) 1,3(m,2H), 1,5(m,2H), 2.3(m,1H), 2.7(s,3H), 7.6–8.0(m,3H), starting from 5-cyclopropyl-4-[4-(methylsulphinyl)-2-trifluoromethylbenzoyl]isoxazole.

COMPOUND 652: 1-[2-bromo-3-methoxy-4-(methylsulphonyl)phenyl]-2-cyanobutan-1,3-dione, m.p. 111° C., starting from 4-[2-bromo-3-methoxy-4-(methylsulphonyl)benzoyl]-5-methylisoxazole.

COMPOUND 653: 1-[2,3-dichloro-4-(methylsulphonyl)phenyl]-2-cyano-3-(1-methylcyclopropyl)propan-1,3-dione, m.p. 179.5° C., starting from 4-[2,3-dichloro-4-(methylsulphonyl)benzoyl]-5-(1-methylcyclopropyl)isoxazole.

COMPOUND 654: 1-[2-chloro-3-methoxy-4-(methylsulphonyl)phenyl]-2-cyano-3-cyclopropylpropan-1,3-dione, m.p. 147.5° C., starting from 4-[2-chloro-3-methoxy-4-(methylsulphonyl)benzoyl]-5-cyclopropylisoxazole.

COMPOUND 655: 1-[2-chloro-3-methoxy-4-(methylsulphonyl)phenyl]-2-cyanobutan-1,3-dione, m.p. 123° C., starting from 4-[2-chloro-3-methoxy-4-(methylsulphonyl)benzoyl]-5-methyl isoxazole.

COMPOUND 656: 1-[2-bromo-4-(methylsulphonyl)phenyl]-2-cyano-3-cyclopropylpropan-1,3-dione, m.p. 165° C., starting from 4-[2-bromo-4-(methylsulphonyl)benzoyl]-5-cyclopropylisoxazole.

COMPOUND 657: 1-[2-bromo-4-(methylsulphonyl)phenyl]-2-cyano-3-(1-methylcyclopropyl)propan-1,3-dione, m.p. 146° C., starting from 4-[2-bromo-4-(methylsulphonyl)benzoyl]-5-(1-methylcyclopropyl)isoxazole.

COMPOUND 658: 2-cyano-3-(1-methylcyclopropyl)-1-[4-(ethylsulphonyl)-2-trifluoromethylphenyl]propan-1,3-dione as a glass, $^1$H NMR (DMSO-D$_6$): 0.5 (m,2H), 0.85 (m,2H), 1.3(t,3H), 1.35(s,3H), 3.05(q,2H), 7.1–7.7(m,3H), starting from 4-[4-(ethylsulphonyl)-2-trifluoromethylbenzoyl]-5-(1-methylcyclopropyl)isoxazole.

COMPOUND 659: 1-[2-chloro-3-methoxy-4-(methylsulphonyl)phenyl]-2-cyano-3-(1-methylcyclopropyl)propan-1,3-dione, m.p. 127° C., starting from 4-[2-chloro-3-methoxy-4-(methylsulphonyl)benzoyl]-5-(1-methylcyclopropyl)isoxazole.

COMPOUND 660: 1-[2-chloro-4-(methylsulphinyl)phenyl]-2-cyano-3-cyclopropylpropan-1,3-dione, m.p. 119.5° C., starting from 4-[2-chloro-4-(methylsulphinyl)benzoyl]-5-cyclopropylisoxazole.

EXAMPLE 9

Triethylamine (0.58 g) was added to a stirred solution of 4(2-bromo-3-methoxy-4-methylsulphenylbenzoyl)-5-cyclopropylisoxazole (2.0 g) in dichloromethane and the mixture was stirred at room temperature for 3 hours. The mixture was evaporated to dryness and the residue triturated with ether and filtered. The solid was re-dissolved in dichloromethane and washed with hydrochloric acid (2M). The organic layer was washed with water, dried (MgSO$_4$) and filtered. The filtrate was evaporated to dryness and the residue triturated with ether and filtered to give 1-(2-bromo-3-methoxy-4-methylsulphenylphenyl)-2-cyano-3-cyclopropylpropan-1,3-dione (COMPOUND 661, 1.33 g) as a white solid, m.p. 128°–129° C.

By proceeding in a similar manner the following compounds were prepared from the appropriately substituted starting materials.

COMPOUND 662: 1-(2-bromo-3-methoxy-4-methylsulphinylphenyl)-2-cyano-3-cyclopropylpropan-1,3-dione, m.p. 185.5°–187.5° C., starting from 4-(2-bromo-3-methoxy-4-methylsulphinylbenzoyl)-5-cyclopropylisoxazole.

COMPOUND 663: 1-(2-bromo-3-methoxy-4-methylsulphonylphenyl)-2-cyano-3-cyclopropylpropan-1,3-dione, m.p. 135.5°–137.5° C., starting from 4-(2-bromo-3-methoxy-4-methylsulphonylbenzoyl)-5-cyclopropylisoxazole.

EXAMPLE 10

Triethylamine (1.78 g) was added to a stirred solution of 4,4-dimethyl-3-oxopentanenitrile (2.0 g) in dichloromethane and the mixture was stirred at room temperature for 2 hours. A solution of 2-chloro-4-methylsulphenylbenzoyl chloride (3.02 g) in dichloromethane was added and the mixture stirred at room temperature overnight. Acetone cyanohydrin (1.36 g) was added and the mixture stirred for 4 days, then filtered. The filtrate was washed with hydrochloric acid (2M), water, aqueous sodium bicarbonate solution, water, then dried (MgSO$_4$) and filtered. The filtrate was evaporated to dryness and the residue purified by column chromatography (hexane, ethyl acetate and acetic acid). The main fraction was washed with aqueous sodium hydroxide (2M), water, dried and evaporated to dryness to give 1-(2-chloro-4-methylsulphenylphenyl)-2-cyano-4,4-dimethylpentan-1,3-dione (COMPOUND 664, 0.16 g) as a white solid, m.p. 97°–99° C.

EXAMPLE 11

Triethylamine (0.5 g) was added to a solution of 5-cyclopropyl-4-(4-methyl-3-methylsulphenylbenzoyl)isoxazole (0.66 g) in dichloromethane. The mixture was stirred at room temperature overnight. Further triethylamine (0.2 g) was added and the mixture was stirred for a further 24 hours. Hydrochloric acid (2M) was added and the layers were separated. The organic layer was washed with aqueous sodium chloride solution, dried (Na$_2$SO$_4$) and filtered. The filtrate was evaporated to dryness to give 2-cyano-3-cyclopropyl-1-(4-methyl-3-methylsulphenylphenyl)propan-1,3-dione (COMPOUND 665, 0.12 g) as an orange gum which solidified, m.p. 64.7°–67.9° C.

By proceeding in a similar manner the following compounds may be prepared from the appropriately substituted starting materials.

COMPOUND 666: 2-cyano-3-cyclopropyl-1-(4-methyl-3-methylsulphonylphenyl)propan-1,3-dione, m.p. 133.6°–135.6° C., starting from 5-cyclopropyl-4-(4-methyl-3-methylsulphonylbenzoyl)isoxazole.

COMPOUND 667: 2-cyano-3-cyclopropyl-1-(4-methyl-3-methylsulphinylphenyl)propan-1,3-dione, m.p. 104.3° C., starting from 5-cyclopropyl-4-(4-methyl-3-methylsulphinylbenzoyl)isoxazole.

REFERENCE EXAMPLE 1

A mixture of 5-cyclopropyl-4-(2-phenylsulphenyl-4-trifluoromethyl)benzoylisoxazole (1 g) and 3-chloroperoxybenzoic acid (1 g) in dichloromethane was stirred at room temperature for 1 hour. The precipitate was filtered and the filtrate washed with aqueous sodium metabisulphite, aqueous sodium bicarbonate, dried over anhydrous sodium sulphate and filtered. The dichloromethane was evaporated to give 5-cyclopropyl-4-(2-phenylsulphonyl-4-trifluoromethyl)-benzoylisoxazole as a white solid, m.p. 174° C.

By proceeding in a similar manner the following compounds of formula (II) were prepared from the appropriately substituted starting materials.

| $R^{31}$ | R | $R^1$ | $R^2$ | $R^3$ | $R^4$ | $R^5$ | m.p. (°C.) |
|---|---|---|---|---|---|---|---|
| H | cPr | H | $SO_2$-cHex | H | $CF_3$ | H | 49.6–51 |
| H | cPr | H | $CH_2SO_2Me$ | H | Br | H | 153.6–154.8 |

Note:
cPr represents cyclopropyl
cHex represents cyclohexyl

REFERENCE EXAMPLE 2

A mixture of 3-cyclopropyl-2-ethoxymethylene-1-(2-phenylsulphenyl-4-trifluoromethylphenyl)propan-1,3-dione (7 g), hydroxylamine hydrochloride (1.24 g) and sodium acetate (1.5 g) in ethanol was stirred at 25° C. for 2 hours. The mixture was then poured into water and extracted with ethyl acetate. The solution was dried over anhydrous sodium sulphate and filtered. The filtrate was evaporated and the residue purified by column chromatography on silica, using a mixture of ethyl acetate and hexane as eluent. The resulting solution was evaporated and the residue crystallized from cyclohexane to give 3.06 g of 5-cyclopropyl-4-(2-phenylsulphenyl-4-trifluoromethylbenzoyl)isoxazole, m.p. 115° C.

By proceeding in a similar manner the following compounds of formula (II) were prepared from the appropriately substituted starting materials.

| $R^{31}$ | R | $R^1$ | $R^2$ | $R^3$ | $R^4$ | $R^5$ | m.p. (°C.) or NMR |
|---|---|---|---|---|---|---|---|
| H | cPr | H | Cl | H | $SO_2NMe_2$ | H | 113–115 |
| H | cPr | H | Cl | H | $NHSO_2Me$ | H | 122.8–124.5 |
| H | cPr | H | $OSO_2Me$ | H | Cl | H | 71–73 |
| H | cPr | H | $OSO_2Me$ | H | H | H | a |
| H | cPr | H | $CF_3$ | H | $SO_2NMe_2$ | H | 133.6–135.2 |
| H | cPr | H | $N(Me)SO_2Me$ | H | Cl | H | 128.3–130.8 |
| H | cPr | H | $OSO_2Et$ | H | H | H | b |
| H | cPr | H | $CH_2SMe$ | H | Br | H | 84.2–85.7 |
| H | cPr | H | $OSO_2NMe_2$ | H | H | H | c |
| H | cPr | H | $OSO_2Me$ | H | H | Cl | 110–113 |

Note:
cPr represents cyclopropyl
a NMR ($CDCl_3$) 1.1–1.2(m, 2H) 1.25–1.35(m, 2H) 2.5–2.6(m, 1H) 3.1(s, 3H) 7.3–7.6(m, 4H) 8.2(s, 1H).
b NMR ($CDCl_3$) 1.15–1.3(m, 2H) 1.3–1.4(m, 2H) 1.45(t, 3H) 2.55–2.7(m, 1H), 3.3(q, 2H) 7.35–7.7(m, 4H) 8.25(s, 1H).
c NMR ($CDCl_3$) 1.15–1.25(m, 2H) 1.25–1.35(m, 2H) 2.55–2.7(m, 1H) 2.35(s, 6H) 7.35–7.6(m, 4H) 8.25(s, 1H).

REFERENCE EXAMPLE 3

Hydroxylamine hydrochloride (0.76 g) was added to a mixture of 1-[4-chloro-2-(N-ethyl-N-methylsulphonylamino)phenyl]-3-cyclopropyl-2-dimethylaminomethylenepropan-1,3-dione(3.83 g) in ethanol. The mixture was stirred for 1 hour and evaporated to dryness. The residue was dissolved in dichloromethane and washed with water, dried ($MgSO_4$) and filtered. The filtrate was evaporated to dryness and the residue was purified by chromatography eluted with a mixture of cyclohexane, dichloromethane and ethyl acetate. The product was triturated with a mixture of ether and hexane and filtered to give 4-[4-chloro-2-(N-ethyl-N-methylsulphonylamino)benzoyl]-5-cyclopropylisoxazole (0.81 g) as a white solid, m.p. 114°–115.8° C.

By proceeding in a similar manner the following compounds of formula (II) were prepared from the appropriately substituted starting materials.

| $R^{31}$ | R | $R^1$ | $R^2$ | $R^3$ | $R^4$ | $R^5$ | mp (°C.) |
|---|---|---|---|---|---|---|---|
| H | cPr | H | S-cHex | H | $CF_3$ | H | 83.4–84.2 |
| H | cPr | H | $CH_2SMe$ | H | Br | H | 84.2–85.6 |
| H | cPr | H | $N(Me)SO_2Me$ | H | $NO_2$ | H | 113–115 |
| H | cPr | H | Cl | H | $N(Me)SO_2Me$ | H | 92.4–94.2 |
| H | cPr | H | $NO_2$ | H | $N(Me)SO_2Me$ | H | 116–117 |
| H | cPr | H | $N(Me)SO_2Me$ | H | Me | H | 120–122 |

Note:
cPr represents cyclopropyl
cHex represents cyclohexyl

REFERENCE EXAMPLE 4

A mixture of 3-cyclopropyl-1-(2-phenylsulphenyl-4-trifluoromethylphenyl)propan-1,3-dione (6.0 g) and triethylorthoformate (4.9 g) in acetic anhydride was stirred and heated at reflux for 3 hours. It was cooled and evaporated. The residue was treated with toluene and re-evaporated to dryness to give 1-cyclopropyl-2-ethoxymethylene-3-(2-phenylsulphenyl-4-trifluoromethylphenyl)propan-1,3-dione (6.7 g) as a red oil.

By proceeding in a similar manner the following compounds were prepared from the appropriately substituted starting materials.

| R | $R^1$ | $R^2$ | $R^3$ | $R^4$ | $R^5$ |
|---|---|---|---|---|---|
| cPr | H | Cl | H | $SO_2NMe_2$ | H |
| cPr | H | Cl | H | $NHSO_2Me$ | H |
| cPr | H | $OSO_2Me$ | H | Cl | H |
| cPr | H | $OSO_2Me$ | H | H | H |
| cPr | H | $CF_3$ | H | $SO_2NMe_2$ | H |
| cPr | H | $N(Me)SO_2Me$ | H | Cl | H |
| cPr | H | $OSO_2Et$ | H | H | H |
| cPr | H | $OSO_2NMe_2$ | H | H | H |
| cPr | H | $OSO_2Me$ | H | H | Cl |

Note:
cPr represents cyclopropyl

REFERENCE EXAMPLE 5

A mixture of 1-[4-chloro-2-(N-ethyl-N-methylsulphonylamino)phenyl]-3-cyclopropylpropan-1,3-dione (3.5 g) and dimethylformamide dimethyl acetal (1.5 ml) in dichloromethane was stirred at room temperature overnight and heated at reflux for 3 days. After cooling the mixture was evaporated to dryness to give 1-[4-chloro-2-(N-ethyl-N-methylsulphonylaminophenyl]-3-cyclopropyl-2-dimethylaminomethylenepropan-1,3-dione (3.83 g) as an orange gum which was not purified further.

By proceeding in a similar manner the following compounds were prepared from the appropriately substituted starting materials.

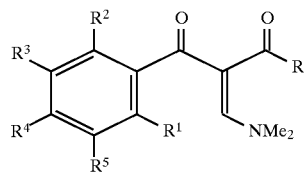

| R | R¹ | R² | R³ | R⁴ | R⁵ |
|---|----|----|----|----|----|
| cPr | H | S-cHex | H | CF₃ | H |
| cPr | H | CH₂SMe | H | Br | H |
| cPr | H | N(Me)SO₂Me | H | NO₂ | H |
| cPr | H | Cl | H | N(Me)SO₂Me | H |
| cPr | H | NO₂ | H | N(Me)SO₂Me | H |
| cPr | H | N(Me)SO₂Me | H | Me | H |

Note:
cPr represents cyclopropyl
cHex represents cyclohexyl

REFERENCE EXAMPLE 6

A solution of methyl (2-phenylsulphenyl-4-trifluoromethyl)benzoate (8 g) and cyclopropyl methyl ketone (4.2 g) in tetrahydrofuran was added to a suspension of sodium hydride (1.65 g of 80% NaH in oil) in tetrahydrofuran at 60° C. After the addition was complete the temperature was kept at 60° C. for a further 15 minutes. The mixture was then cooled to 25° C. and poured into water. An aqueous solution of hydrochloric acid was added to the mixture to pH 1. The mixture was extracted with ethyl acetate, dried over anhydrous sodium sulphate, filtered and evaporated. The residue was purified by chromatography on silica, using ethyl acetate as eluent to give, after evaporation of the solvent, 3-cyclopropyl-1-(2-phenylsulphenyl-4-trifluoromethylphenyl)-propan-1,3-dione as a red oil (8.07 g), NMR (CDCl₃) 0.9(2H,m), 1.25(2H,m), 1.70(1H,m), 6.05 (1H,s), 7.1(1H,s), 7.3–7.5(6H,m), 7.6(1H,s).

By proceeding in a similar manner 3-cyclopropyl-1-(2-methylsulphenylmethyl-4-bromophenyl)-propan-1,3-dione, NMR(CDCl₃) 0.9–11(m,4H) 1.6–1.75(m,1H) 2.05(s,3H) 3.9(s,2H) 6.0(s,1H) 7.35(d,1H) 7.45(d,1H) 7.6(s,1H) 15.9–16.2(bs,1H) was prepared.

REFERENCE EXAMPLE 7

A suspension of magnesium (0.47 g) in methanol was warmed gently to initiate reaction and then heated at reflux until all of the magnesium had dissolved. It was cooled slightly and t-butyl 3-cyclopropyl-3-oxopropionate (2.39 g) was added. The mixture was stirred and heated at reflux for 25 minutes then evaporated to dryness. It was dissolved in toluene and re-evaporated to dryness. The residue was again dissolved in toluene and 2-chloro-4-(methylsulphonylamino)benzoyl chloride (3.2 g) was added. The mixture was stirred at room temperature overnight. Hydrochloric acid (2M) was added and the mixture was stirred. The layers were separated and the organic layer was dried (MgSO₄) and filtered. The filtrate was evaporated to give t-butyl 2-[2-chloro-4-(methylsulphonylamino) benzoyl]-3-cyclopropyl-3-oxopropionate (3.7 g) as a white solid, m.p. 137°–140° C.

t-Butyl 2-[2-chloro-4-(methylsulphonylamino)benzoyl]-3-cyclopropyl-3-oxopropionate (2 g) was dissolved in toluene and p-toluenesulphonic acid (0.2 g) was added. The mixture was stirred and heated at reflux for 0.5 hours. It was cooled, washed with water, dried (MgSO₄) and filtered. The filtrate was evaporated to dryness to give 1-[2-chloro-4-(methylsulphonylamino)phenyl]-3-cyclopropylpropan-1,3-dione (1.48 g) as a white solid, m.p. 119.9°–121.6° C.

By proceeding in a similar manner the following compounds of formula (XI) were prepared from the appropriately substituted starting materials without isolation of the intermediate ester.

| R | R¹ | R² | R³ | R⁴ | R⁵ | m.p. (°C.) or NMR |
|---|----|----|----|----|----|-------------------|
| cPr | H | Cl | H | SO₂NMe₂ | H | 71.5–76.5 |
| cPr | H | OSO₂Me | H | Cl | H | a |
| cPr | H | OSO₂Me | H | H | H | b |
| cPr | H | CF₃ | H | SO₂NMe₂ | H | — |
| cPr | H | N(Me)SO₂Me | H | Cl | H | 93.3–96.5 |
| cPr | H | OSO₂Et | H | H | H | c |
| cPr | H | ScHex | H | CF₃ | H | d |
| cPr | H | OSO₂NMe₂ | H | H | H | 51–59 |
| cPr | H | OSO₂Me | H | H | Cl | e |
| cPr | H | N(Me)SO₂Me | H | NO₂ | H | – |
| cPr | H | N(Et)SO₂Me | H | Cl | H | f |
| cPr | H | Cl | H | N(Me)SO₂Me | H | – |
| cPr | H | NO₂ | H | N(Me)SO₂Me | H | – |
| cPr | H | N(Me)SO₂Me | H | Me | H | g |

Note:
cPr represents cyclopropyl
cHex represents cyclohexyl
a NMR (CDCl₃) 0.8–0.9(m, 2H) 1.0–1.15(m, 2H) 1.6–1.7(m, 1H) 3.05(s, 3H) 6.1(s, 1H) 7.25(d, 1H) 7.35(s, 1H) 7.55(d, 1H).
b NMR (CDCl₃) 0.9–1.05(m, 2H) 1.1–1.2(m, 2H) 1.7–1.8(m, 1H) 3.1(s, 3H) 6.15(s, 1H) 7.25–7.5(m, 3H) 7.65(d, 1H) 15.85–16.3(bs, 1H).
c NMR (CDCl₃) 0.9–1.1(m, 2H) 1.2–1.3(m, 2H) 1.5(t, 3H) 1.7–1.85(m, 1H) 3.3(q, 2H) 6.2(s, 1H) 7.3–7.55(m, 3H) 7.75(d, 1H) 15.9–16.2(bs, 1H).
d NMR (CDCl₃) 0.8–2.1(m, 15H) 3.1–3.3(m, 1H) 6.0(s, 1H) 7.35(d, 1H) 7.5(d, 1H) 7.6(s, 1H) 15.6–16.0(bs, 1H).
e NMR (CDCl₃) 0.9–1.15(m, 2H) 1.2–1.3(m, 2H) 1.7–1.85(m, 1H) 3.15(s, 3H) 6.2(s, 1H) 7.3–7.55(m, 2H) 7.75(s,1H) 15.85–16.25(bs, 1H).
f NMR (CDCl₃) 0.9–1.4(m, 7H) 1.7–1.9(m, 1H) 3.0(s, 3H) 3.65(q, 2H) 6.1(s, 1H) 7.4(m, 2H) 7.55(d, 1H) 16.0–16.3(bs, 1H)
g NMR (CDCl₃) 0.9–1.1(m, 2H) 1.15–1.25(m, 2H) 1.7–1.85(m, 1H) 2.35(s, 3H) 2.95(s, 3H) 3.25(s, 3H) 6.1(s, 1H) 7.15(d, 1H) 7.2(s, 1H) 7.5(d, 1H) 16.1–16.3(bs, 1H).

REFERENCE EXAMPLE 8

3,5-Bis(trifluoromethyl)benzoyl chloride (1.15 g) in acetonitrile was added to a stirred solution of 4-chloro-2-methylsulphenylbenzoyl-acetonitrile (1 g) and triethylamine (0.62 ml) in acetonitrile at room temperature. The reaction mixture was stirred for 4 hours. After evaporating the solvent, the residue was chromatographed using dichloromethane/hexane to give [(alpha-cyanomethylene)-4-chloro-2-methylsulphenylbenzyl] 3,5-bis(trifluoromethyl)benzoate (1.33 g), m.p. 130°–132° C.

REFERENCE EXAMPLE 9 n Butyl lithium (2.5M in hexane, 55.24 ml) was added under an inert atmosphere to a stirred cooled solution of cyanoacetic acid (pre-dried, 5.9 g) in tetrahydrofuran whilst maintaining the temperature below −70° C. for 1 hour and then allowed to warm to approximately +10° C. for a further 1 hour.

The mixture was re-cooled to approximately −78° C. and a solution of 4-chloro-2-methylsulphenylbenzoyl chloride (7.7 g) in tetrahydrofuran (40 ml) was added over 30 minutes. The mixture was stirred at approximately −78° C. for 12 hours, then allowed to warm to room temperature for 8 hours.

The mixture was treated with hydrochloric acid (2M, 500 ml) and stirred for 2 hours. The organic layer was separated, dried (magnesium sulphate), filtered and evaporated to give a brown solid. Recrystallisation from toluene gave 4-chloro-2-methylsulphenylbenzoyl-acetonitrile (6.3 g), m.p. 139°–141° C.

Benzoyl chlorides were prepared by heating the appropriately substituted benzoic acids with thionyl chloride. The excess thionyl chloride was removed by evaporation the benzoyl chlorides thus obtained were used without further purification.

REFERENCE EXAMPLE 10

A mixture of 2-phenylsulphenyl-4-trifluoromethylbenzoic acid (11.5 g), thionyl chloride (11.4 g), dimethylformamide (0.2 ml) and dichloroethane was heated at reflux for 90 minutes. The solution was then concentrated under reduced pressure and the residue was dissolved in methanol and heated at reflux for one hour. The resulting solution was poured into aqueous sodium bicarbonate and extracted with ether. The organic phase was dried over anhydrous sodium sulphate, filtered and evaporated. The resulting material was crystallised from hexane to give methyl 2-phenylsulphenyl-4-trifluoromethylbenzoate (10.5 g) as white crystals, m.p. 58° C.

REFERENCE EXAMPLE 11

A mixture of 2-phenylsulphenyl-4-trifluoromethylbenzonitrile (9 g), concentrated sulphuric acid (27 ml) and water was heated at reflux for 10 hours. The mixture was then cooled, poured into water and extracted with dichloromethane. The organic extract was extracted with aqueous sodium hydroxide. The resulting aqueous solution was acidified with aqueous hydrochloric acid to pH 1. The suspension was extracted with dichloromethane, dried over anhydrous sodium sulphate, filtered and after evaporation of the dichloromethane 2-phenylsulphenyl-4-trifluoromethylbenzoic acid was obtained as a white solid (7.5 g), m.p. 161° C.

REFERENCE EXAMPLE 12

2-Cyclohexylsulphenyl-4-trifluoromethylbenzonitrile (10.55 g) was added to a mixture of sodium hydroxide (52.75 g) in aqueous ethanol and the resultant mixture was stirred and heated at reflux for 23 hours. It was cooled, diluted with water and filtered. The filtrate was acidified and extracted with dichloromethane, washed with water, dried (MgSO$_4$) and filtered to give 2-cyclohexylsulphenyl-4-trifluoromethylbenzoic acid (10.7 g) as an off-white solid m.p. 115.4°–116.4° C.

REFERENCE EXAMPLE 13

A mixture of 2-nitro-4-trifluoromethylbenzonitrile (8.64 g), thiophenol (4.4 g), potassium carbonate (6.9 g) in acetonitrile was heated at reflux for 4 hours. After cooling, the mixture was poured into water and extracted with dichloromethane. The organic extract was dried over anhydrous sodium sulphate, filtered and concentrated under reduced pressure. The residue was triturated with hexane to give 2-phenylsulphenyl-4-trifluoromethylbenzonitrile as a white solid (9.5 g), m.p. 51° C.

By proceeding in a similar manner 2-cyclohexylsulphenyl-4-trifluoromethyl-benzonitrile, NMR (CDCl$_3$) 1.1–2.0(m,10H) 3.25(m,1H) 7.4(d,1H) 7.55 (s,1H) 7.65(d,1H) was prepared from the appropriately substituted starting material.

REFERENCE EXAMPLE 14

2N Sodium hydroxide solution (20 ml) was added to a stirred solution of methyl 4-chloro-2-(N-methyl-N-methylsulphonylamino)benzoate (2.75 g) in methanol. The mixture was stirred at reflux for 0.5 hours. After cooling, the mixture was acidified with 2N hydrochloric acid and extracted with ethyl acetate. The organic extracts were combined, dried and evaporated to yield 4-chloro-2-(N-methyl-N-methylsulphonylamino)benzoic acid as a white solid (2.45 g), m.p. 161°–164° C.

By proceeding in a similar manner, the following compounds were prepared:
2-(N-methyl-N-methylsulphonylamino)-4-nitrobenzoic acid NMR (DMSO-d$_6$) 3.1(s,3H) 3.3(s,3H) 7.95(d,1H) 8.3(d, 1H) 8.4(s,1H) 13.3–13.8(bs,1H);
4-chloro-2-(N-ethyl-N-methylsulphonylamino)benzoic acid m.p. 148°–151° C.;
2-chloro-4-(N-methyl-N-methylsulphonylamino)benzoic acid m.p.152°–153° C.;
4-(N-methyl-N-methylsulphonylamino)-2-nitrobenzoic acid m.p. 177°–178.6° C.; and
4-methyl-2-(N-methyl-N-methylsulphonylamino)benzoic acid m.p. 185°–187° C.

REFERENCE EXAMPLE 15

Potassium carbonate (12.5 g) was added to a stirred solution of methyl 4-chloro-2-(N-methylsulphonylamino) benzoate (7.5 g) in acetone. The mixture was stirred for 15 minutes and methyl iodide (8.0 g) was added. The resultant mixture was stirred at room temperature for 1 hour and left to stand overnight. The mixture was evaporated to dryness and the residue was dissolved in ethyl acetate and washed with sodium hydroxide solution (2M) and water, dried (anhydrous MgSO$_4$) and filtered. The filtrate was evaporated to dryness to give methyl 4-chloro- 2-(N-methyl-N-methylsulphonylamino)benzoate (4.9 g) as a white solid, m.p. 73°–75° C.

By proceeding in a similar manner the following compounds were prepared from the appropriately substituted starting materials. methyl 2-chloro-4-(N-methyl-N-methylsulphonylamino)benzoate, NMR (DMSO-d$_6$) 3.05(s, 3H) 3.35(s,3H) 3.85(s,3H) 7.5(d,1H) 7.6(s,1H) 7.85(d,1H); methyl 2-(N-methyl-N-methylsulphonylamino)-4-nitrobenzoate, NMR (DMSO-d$_6$) 3.05(s,3H) 3.25(s,3H) 3.8 (s,3H) 8.0(d,1H) 8.3(d,1H) 8.4(s,1H); and ethyl 4-chloro-2-(N-ethyl-N-methylsulphonylamino)benzoate, NMR (CDCl$_3$) 1.1(t,3H) 1.35(t,3H) 2.9(s,3H) 3.65(q,2H) 4.3(q, 2H) 7.3(d,1H) 7.35(s,1H) 7.8(d,1H).

REFERENCE EXAMPLE 16

Methyl iodide (22.0 ml) was added to a stirred suspension of 4-methyl-2-(N-methylsulphonylamino)benzoic acid (8.0 g) and anhydrous potassium carbonate (24.2 g) in acetone and the mixture was stirred and heated at reflux overnight. The mixture was cooled and filtered and the filtrate was evaporated to dryness. The residue was dissolved in dichloromethane and washed with aqueous sodium bicarbonate solution, water, dried (MgSO$_4$) and filtered. The filtrate was evaporated to dryness to give methyl 4-methyl-2-(N-methyl-N-methylsulphonylamino)benzoate (8.36 g) as a cream solid, m.p. 100°–103° C.

By proceeding in a similar manner methyl 4-(N-methyl-N-methylsulphonylamino)-2-nitrobenzoate, NMR (CDCl$_3$) 2.95(s,3H) 3.4(s,3H) 3.9(s,3H) 7.7(d,1H) 7.75(d,1H) 7.85 (s,1H) was prepared from the appropriately substituted starting material.

REFERENCE EXAMPLE 17

A solution of methanesulphonyl chloride (6.3 g) in dichloromethane was added to a stirred, cooled (0°–5° C.) solution of methyl 2-amino-4-chlorobenzoate (9.5 g) in dichloromethane. Triethylamine (7.1 g) was then added and the mixture was stirred at 0°–5° C. for 10 minutes and then at room temperature for 0.5 hours.

The mixture was diluted with 2N hydrochloric acid. The organic phase was separated, washed with water, dried and evaporated.

The crude product was purified by column chromatography to yield methyl 4-chloro-2-(N-methylsulphonylamino) benzoate as a white solid, (3.6 g) m.p. 125.5°–128.1° C.

REFERENCE EXAMPLE 18

Concentrated sulphuric acid (20 ml) was added to a suspension of 2-chloro-4-(N-methylsulphonylamino) benzoic acid (10.3 g) in methanol and the mixture was stirred and heated at reflux for 22 hours. It was cooled, evaporated to dryness and diluted with water, extracted with ethyl acetate, washed with aqueous sodium bicarbonate solution, water, dried ($MgSO_4$) and filtered. The filtrate was evaporated to dryness to give methyl 2-chloro-4(N-methylsulphonylamino)benzoate(10.0 g) as an off-white solid, NMR (DMSO-$d_6$) 3.15(s,3H) 3.85(s,3H) 7.2(d,1H) 7.3(s,1H) 7.85(d,1H) 10.5(s,1H).

By proceeding in a similar manner methyl 2-(N-methylsulphonylamino)-4-nitrobenzoic acid NMR ($CDCl_3$) 3.15 (s,3H) 4.0(s,3H) 7.9(d,1H) 8.25(d,1H) 8.5(s,1H) 10.65 (s,1H) was prepared from the appropriately substituted starting material.

REFERENCE EXAMPLE 19

A mixture of 2-chloro-4-(N-methylsulphonylamino) benzoic acid and 2-chloro-4-[N,N-bis(methysulphonyl) amine]benzoic acid (3.6 g) in aqueous sodium hydroxide (2M) and methanol was stirred and heated at reflux for 0.5 hours. It was cooled and the methanol was removed by evaporation. The aqueous residue was acidified and the product was filtered off to give 2-chloro-4-(N-methylsulphonylamino)benzoic acid (3.4 g) as a white solid, m.p. 256°–258° C.

By proceeding in a similar manner the following compound was prepared from the appropriately substituted starting materials. 2-(N-methylsulphonylamino)-4-nitrobenzoic acid, NMR (DMSO-$d_6$) 3.3(s,3H) 7.9(d,1H) 8.2(d,1H) 8.35 (s,1H) 10.5–11.1(bs,1H).

REFERENCE EXAMPLE 20

An aqueous solution of sodium hydroxide (11.0 g) was added to a solution of a mixture of methyl 4-methyl-2-(N,N-bis(methysulphonyl)amino]benzoate and methyl 4-methyl-2-(N-methylsulphonylamino)benzoate(23.26 g) in methanol and the resulting suspension was heated at reflux for 1 hour. It was cooled and the methanol was removed by evaporation. The aqueous solution was acidified and the resultant solid was filtered off to give 4-methyl-2-(N-methylsulphonylamino)benzoic acid (16.42 g) as a cream solid, m.p. 202°–205° C.

By proceeding in a similar manner the following compound was prepared from the appropriately substituted starting materials.

4-(N-methylsulphonylamino)-2-nitrobenzoic acid, NMR (DMSO-$d_6$) 3.2(s,3H) 7.5(d,1H) 7.6(s,1H) 7.9(d,1H) 10.8 (s,1H) 13.3–14.1(bs,1H).

REFERENCE EXAMPLE 21

Methanesulphonyl chloride (5.72 g) was added to a stirred, cooled (0° C.) mixture of 4-amino-2-chlorobenzoic acid (6.9 g) and triethylamine (13.1 g) in acetonitrile. The mixture was then stirred at room temperature for 3.5 hours. Triethylamine (4 g) was added and the mixture was cooled to 0° C. and further methanesulphonyl chloride (3.8 g) was added. The mixture was then stirred at room temperature for one hour. The mixture was filtered and the filtrate evaporated. The residue was dissolved in 2N sodium hydroxide solution and washed with diethyl ether. The aqueous solution was acidified to pH 2–3 with 2N hydrochloric acid and then extracted with ethyl acetate. The organic extracts were evaporated. The residue was triturated with diethyl ether to yield a mixture of 2-chloro-4-(N-methylsulphonylamino) benzoic acid and 2-chloro-4-[N,N-bis(methylsulphonyl) amino]benzoic acid.

REFERENCE EXAMPLE 22

Methanesulphonyl chloride (12.2 ml) was added to a stirred, cooled solution of methyl 2-amino-4-methylbenzoate (10.3 g) and triethylamine (19.5 ml) in dichloromethane while maintaining the temperature below 0° C. The mixture was stirred at room temperature for 4 hours. Hydrochloric acid (2M) was added and the layers were separated. The organic layer was washed with water, dried ($MgSO_4$) and filtered. The filtrate was evaporated to dryness to give a mixture of methyl 4-methyl-2-[N,N-bis (methylsulphonyl]amino]benzoate and methyl 4-methyl-2-(N-methylsulphonylamino)benzoate (18.26 g) as a yellow solid which was not further purified.

By proceeding in a similar manner 4-[N,N-bis-(methylsulphonyl)amino]-2-nitrobenzoic acid was prepared from the appropriately substituted starting material.

REFERENCE EXAMPLE 23

A mixture of methyl 2-(methylsulphonyloxy)benzoate (6.9 g) in hydrochloric acid (6M) was heated at reflux for 0.75 hours. The cooled mixture was diluted with ether and extracted with ethyl acetate. The organic layer was washed with aqueous sodium chloride solution, dried ($MgSO_4$) and filtered. The filtrate was evaporated to dryness to give 2-(methylsulphonyloxy)benzoic acid (6.1 g) as a white solid m.p. 125°–126° C.

By proceeding in a similar manner the following compounds were prepared from the appropriately substituted starting materials. 4-Chloro-2-(methylsulphonyloxy) benzoic, acid m.p. 167°–170° C.

2-(Ethylsulphonyloxy)benzoic acid, m.p. 101.7°–103.2° C.
2-(N,N-Dimethylaminosulphonyloxy)benzoic acid, m.p. 108.5°–111.5° C.
5-Chloro-2-(methylsulphonyloxy)benzoic acid, m.p. 148°–156° C.

REFERENCE EXAMPLE 24

Methane sulphonyl chloride (7.0 g) was added to a stirred, cooled mixture of methyl 4-chlorosalicylate (10.0 g) and triethylamine (8.0 g) in dichloromethane while maintaining the temperature at 0° C. The mixture was then stirred at room temperature for half and hour and left to stand overnight. The mixture was washed with hydrochloric acid (2M) saturated aqueous sodium bicarbonate solution, water, dried ($Na_2SO_4$) and filtered. The filtrate was evaporated to dryness to give methyl 4-chloro- 2-(methylsulphonyloxy)benzoate (11.7 g) as an orange solid m.p. 82.5°–84.5° C.

By proceeding in a similar manner the following compounds were prepared from the appropriately substituted starting materials.

Methyl 2-(ethylsulphonyloxy)benzoate NMR (CDCl$_3$) 1.5(t,3H), 3.4(q,2H) 3.85(s,3H), 7.25–7.4(m,2H), 7.5(m, 1H), 7.9(d,1H).

Methyl 5-chloro-2-(methylsulphonyloxy)benzoate NMR (CDCl$_3$) 3.3(s,3H), 3.95(s,3H), 7.35(d,1H), 7.55(d,1H), 7.95 (s,1H).

REFERENCE EXAMPLE 25

Dimethylaminosulphonyl chloride (17.2 g) was added to a mixture of methyl salicyclate (15.2 g) and potassium carbonate (27.6 g) in acetonitrile. The mixture was stirred at room temperature for 1 hour. TDA-1(2.0 g) was added and the mixture stirred at room temperature for 24 hours. The mixture was filtered and the filtrate was evaporated to dryness. The residue was dissolved in dichloromethane, washed with water, dried (MgSO$_4$) and filtered. The filtrate was evaporated to dryness and the residue was triturated with ether. The solid was filtered off and purified by chromatography eluted with dichloromethane to give methyl 2-(dimethylaminosulphonyloxy)benzoate (17.4 g) as a white solid m.p. 75.5°–76.5° C.

REFERENCE EXAMPLE 26

A mixture of methyl 4-bromo-2-(bromomethyl)benzoate (12 g) and sodium thiomethoxide (2.5 g) in toluene was stirred at 100° C. for 2 hours. The mixture was then cooled, poured into water and extracted with ethyl acetate. The organic layer was separated, washed with brine, dried (anhydrous sodium sulphate) and evaporated to afford a brown oil which was purified by column chromatography on silica gel giving methyl 4-bromo-2-(methylsulphenylmethyl)benzoate (4.1 g) as white crystals, m.p. 79.3° C.

REFERENCE EXAMPLE 27

Isoamyl nitrite (150 ml) was added to a stirred mixture of 4-(N,N-dimethylaminosulphonyl)-2-trifluoromethylbenzamide (15.1 g) in acetic acid and concentrated sulphuric acid while maintaining the temperature at 70°–80° C. It was cooled, poured into water and extracted with ethyl acetate, washed with water, dried (MgSO$_4$) and filtered to give 4-(N,N-dimethylaminosulphonyl)-2-trifluoromethylbenzoic acid (11.2 g) as a white solid, m.p. 188.9°–189.4° C.

REFERENCE EXAMPLE 28

Hydrogen peroxide (30%, 100 ml) was added to a stirred mixture of 4-(N,N-dimethylaminosulphonyl)-2-trifluoromethylbenzonitrile (20.37 g) and sodium hydroxide (1.0 g) in ethanol under an inept atmosphere maintaining the temperature at 40°–45° C. The mixture was stirred and heated at that temperature for 3.5 hours. It was cooled, poured into water, sodium chloride was added and it was extracted with ethyl acetate, washed with water, dried (MgSO$_4$) and filtered. The filtrate was evaporated to dryness and the residue was re-crystallized from a mixture of ethyl acetate and toluene to give 4-(N,N-dimethylaminosulphonyl)-2-trifluoromethylbenzamide (16.44 g) as white crystals, m.p. 149°–156° C.

REFERENCE EXAMPLE 29

Sodium nitrite (0.7 g) in water was added to a stirred cooled solution of 4-amino-2-trifluoromethylbenzonitrile (1.86 g) in a mixture of acetic acid and concentrated hydrochloric acid while maintaining the temperature below 5° C. The mixture was stirred at 0° C. for 0.5 hours then poured into a mixture of liquid sulphur dioxide (10 ml), cupric chloride (0.6 g) and acetic acid at −20° C. The mixture was allowed to warm slowly to room temperature and stirred for 0.75 hours. It was poured into water and extracted with dichloromethane, washed with water, dried (MgSO$_4$) and filtered. The filtrate was evaporated to dryness and the residue was redissolved in dichloromethane and the solution was cooled to 0° C. Liquid dimethylamine (10 ml) was added and the mixture was left to stand overnight. The mixture was evaporated to dryness and the residue was dissolved in ethyl acetate and washed with water, dried (MgSO$_4$) and filtered. The filtrate was evaporated to dryness to give 4-(N,N-dimethylaminosulphonyl)2-trifluoromethylbenzonitrile (2.05 g) as a beige solid, m.p. 133.4°–135.8° C.

By proceeding in a similar manner 2-chloro-4-(N,N-dimethylaminosulphonyl)benzoic acid, m.p. 181.4°–182.4° C. was prepared from the appropriately substituted starting material.

REFERENCE EXAMPLE 30

Sodium acetate (1.93 g) was added to a mixture of 1-[4-chloro-2-(methylsulphonyl)phenyl]-3-cyclopropyl-2-ethoxymethylenepropan-1,3-dione (8.4 g) and hydroxylamine hydrochloride (1.64 g) in ethanol with stirring. The mixture was stirred at room temperature overnight. It was evaporated and the residue was dissolved in ethyl acetate, washed with water, dried (anhydrous magnesium sulphate) and filtered. The filtrate was evaporated to dryness and the residue was recrystallized from ether to give 4-[4-chloro-2-(methylsulphonyl)benzoyl]-5-cyclopropylisoxazole (4.4 g) as an off-white solid, m.p. 183°–185° C.

By proceeding in a similar manner the following compounds of formula below were prepared from the appropriately substituted starting materials:

| R | $R^3$ | $R^4$ | $R^5$ | $R^{41}$ | n | m.p. |
|---|---|---|---|---|---|---|
| Cp | H | H | H | Me | 2 | 119° C. |
| Cp | H | H | H | isoPr | 2 | 106° C. |
| 1-Me—Cp | H | Cl | H | Me | 2 | 136° C. |
| isoPr | H | Cl | H | Me | 2 | 134° C. |
| Cp | H | Me | H | Me | 2 | 163.5° C. |
| Cp | H | MeO | H | Me | 2 | 179° C. |
| Cp | H | Cl | H | Me | 0 | 100° C. |
| Cp | H | Br | H | Me | 2 | 194° C. |
| Cp | H | CF$_3$ | H | Me | 2 | 133.5° C. |
| Cp$^{58}$ | Cl | Cl | H | Me | 0 | 83.5–84.5 |
| Cp | F | Cl | H | Me | 0 | 73–74 |
| Cp | Me | Me | H | Me | 0 | 100–102 |
| Cp | Cl | Br | H | Me | 0 | 93–94 |
| Cp | OMe | Cl | H | Me | 0 | NMR(a) |

Note:
Cp represents cyclopropyl.
(a) NMR (CDCl$_3$) 1.2(2H, m), 1.4(2H, m), 2.4(3H, s), 2.6(1H, m), 4.0(3H, s), 7.05(1H, d), 7.45(1H, d), 8.15(1H, s).

REFERENCE EXAMPLE 31

A mixture of 3-cyclopropyl-2-(N,N-dimethylaminomethylene)-1-[2-(1-methylpropylsulphenyl)-

4-trifluoromethylphenyl]propan-1,3-dione (11.9 g) and hydroxylamine hydrochloride (2.3 g) in ethanol was stirred at room temperature overnight. The mixture was cooled (ice bath) and a solid filtered off, washed with a small amount of cold ethanol, then water, and dried to give 5-cyclopropyl-4-[2-(1-methylpropylsulphenyl)-4-trifluoromethylbenzoyl]isoxazole (3.8 g) as a white solid, m.p. 75.6°–76.4° C.

By proceeding in a similar manner 5-cyclopropyl-4-[2-(n-propylsulphenyl)-4-trifluoromethylbenzoyl]isoxazole was prepared, m.p. 79°–80° C.

REFERENCE EXAMPLE 32

3-Chloroperoxybenzoic acid (2.0 g) was added to a solution of 5-cyclopropyl-4-[3,4-dichloro-2-(methylsulphenyl)benzoyl]isoxazole (1.86 g) in dichloromethane while maintaining the temperature around −15° C. The mixture was stirred at −15° C. for 1 hour and at room temperature for 1 hour. It was recooled to −15° C. and filtered. The filtrate was evaporated to dryness and the residue was purified by dry column flash chromatography eluted with a mixture of ethyl acetate and n-hexane. The product was recrystallized from a mixture of ethyl acetate and n-hexane to give 5-cyclopropyl-4-[3,4-dichloro-2-(methylsulphinyl)benzoyl]isoxazole (0.3 g) as a white solid, m.p. 110°–112° C.

By proceeding in a similar manner the following compounds were prepared from the appropriately substituted starting materials:

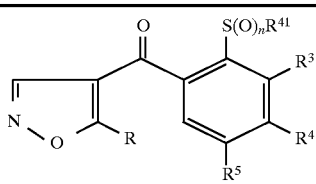

| R | $R^{41}$ | $R^3$ | $R^4$ | $R^5$ | n | m.p (°C.) |
|---|---|---|---|---|---|---|
| Cp | Me | Cl | Cl | H | 2 | 149–150 |
| Cp | Me | F | Cl | H | 1 | 136–137 |
| Cp | Me | F | Cl | H | 2 | 151–152 |
| Cp | nPr | H | $CF_3$ | H | 2 | 116.8–118.8 |
| Cp | Me | OMe | Cl | H | 2 | 63–67 |
| Cp | Me | Cl | Br | H | 1 | 133–134 |
| Cp | Me | Cl | Br | H | 2 | 147–148 |

Note:
Cp represents Cyclopropyl.

REFERENCE EXAMPLE 33

Hydrogen peroxide (30%, 4.7 ml) was added to a stirred, cooled solution of 5-cyclopropyl-4-[2-(1-methylpropylsulphenyl)4-trifluoromethylbenzoyl]isoxazole and acetic anhydride (2.0 ml) maintaining the temperature below 0° C. The reaction mixture was stirred at 0° C. for 0.5 hours and at room temperature for 1 hour, then heated at 85° C. for 1 hour. After cooling to room temperature the mixture was washed with water and extracted with ethyl acetate. The organic phase was washed with brine, aqueous ferrous sulphate solution, brine, dried (sodium sulphate) and filtered. The filtrate was evaporated to give 5-cyclopropyl-4-[2-(1-methylpropylsulphonyl)-4-trifluoromethyl-benzoyl]isoxazole (2.4 g) as an orange solid, m.p. 89°–91° C.

REFERENCE EXAMPLE 34

A mixture of 1-[4-chloro-2-(methylsulphonyl)phenyl]-3-cyclopropylpropan-1,3-dione (7.1 g) and triethyl orthoformate (6.9 g) in acetic anhydride was stirred and heated at reflux for 2 hours. The mixture was evaporated to dryness, toluene was added and the solution was re-evaporated to give 1-[4-chloro-2-(methylsulphonyl)phenyl]-3-cyclopropyl-2-ethoxymethylenepropan-1,3-dione (8.4 g) as a red gum which was not purified further.

By proceeding in a similar manner the following compounds were prepared from the appropriately substituted starting materials:

| R | $R^3$ | $R^4$ | $R^5$ | $R^{41}$ | n |
|---|---|---|---|---|---|
| Cp | H | H | H | Me | 2 |
| Cp | H | H | H | Et | 2 |
| Cp | H | H | H | isoPr | 2 |
| 1-Me—Cp | H | Cl | H | Me | 2 |
| IsoPr | H | Cl | H | Me | 2 |
| Cp | H | Me | H | Me | 2 |
| Cp | H | MeO | H | Me | 2 |
| Cp | H | Cl | H | Me | 0 |
| Cp | H | Br | H | Me | 2 |
| Cp | H | $CF_3$ | H | Me | 2 |
| Cp | Cl | Cl | H | Me | 0 |
| Cp | F | Cl | H | Me | 0 |
| Cp | Me | Me | H | Me | 0 |
| Cp | OMe | Cl | H | Me | 0 |
| Cp | Cl | Br | H | Me | 0 |

Note:
Cp represents Cyclopropyl

REFERENCE EXAMPLE 35

A mixture of 3-cyclopropyl-1-[2-(1-methylpropylsulphenyl)-4-trifluoromethylphenyl]propan-1,3-dione (10.2 g) and dimethylformamide dimethyl acetal (3.9 g) in toluene was stirred at room temperature overnight. The mixture was evaporated to dryness to give 3-cyclopropyl-2-(N,N-dimethylaminomethylene)-1-[2-(11-methylpropylsulphenyl)-4-trifluoromethylphenyl]propan-1,3-dione (11.9 g).

By proceeding in a similar manner 3-cyclopropyl-2-(N,N-dimethylaminomethylene)-1-[2-(n-propylsulphenyl)-4-trifluoromethylphenyl]propan-1,3-dione was prepared.

REFERENCE EXAMPLE 36

A mixture of t-butyl 1-[4-chloro-2-(methylsulphonyl)benzoyl]-3-cyclopropyl-3-oxopropionate (9.5 g) and 4-toluenesulphonic acid (1.5 g) in toluene was stirred and heated at reflux for 3 hours. After cooling, the mixture was washed with water, dried (anhydrous magnesium sulphate) and filtered. The filtrate was evaporated to dryness to give 1-[4-chloro-2-(methylsulphonyl)phenyl]-3-cyclopropylpropan-1,3-dione, (7.1 g) as an orange gum, NMR ($CDCl_3$): 0.8–1.2 (m,4H), 1.5–1.9 (m,1H), 3.25(s,3H), 5.8 (s,1H), 7.3–7.6(m,2H), 7.9 (s,1H).

By proceeding in a similar manner the following compounds were prepared from the appropriately substituted starting materials:

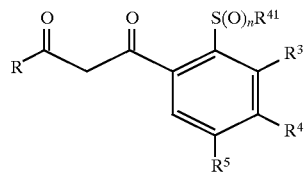

| R | $R^3$ | $R^4$ | $R^5$ | $R^{41}$ | n | mp/NMR (CDCl$_3$) |
|---|---|---|---|---|---|---|
| Cp | H | H | H | Me | 2 | mp: 94.5° C. |
| Cp | H | H | H | Et | 2 | NMR: 0.9–1.3(m, 4H) 1.3(t, 3H) 1.5–1.9(m, 1H) 3.5(q, 2H) 5.85(s, 1H) 7.3–8.1(m, 4H). |
| Cp | H | H | H | iPr | 2 | mp: 140.5° C. |
| 1-MeCp | H | Cl | H | Me | 2 | NMR: 0.7–1.0(m, 2H) 1.1–1.6 (m, 5H) 3.3(s, 3H) 5.8(s, 1H) 7.3–7.6(m, 2H) 7.95(s, 1H). |
| IsoPr | H | Cl | H | Me | 2 | NMR: 1.15(d, 6H) 2.4–2.8(m, 1H) 3.3(s, 3H) 5.7(s, 1H) 7.4–7.6(m, 2H) 7.9(s, 1H). |
| Cp | H | Br | H | Me | 2 | NMR: 0.9–1.35(m, 4H) 1.5–1.9(m, 1H) 3.45(s, 3H) 6.0(s, 1H) 7.5(d, 1H) 7.95(d, 1H) 8.4(s, 1H). |
| Cp | H | CF$_3$ | H | Me | 2 | NMR: 0.8–1.4(m, 4H) 1.5–1.8(m, 1H) 3.3(s, 3H) 5.85(s, 1H) 7.5(d, 1H) 7.8(d, 1H) 82(2, 1H). |
| Cp | H | CF$_3$ | H | secBu | 0 | — |
| Cp | H | CF$_3$ | H | nPr | 0 | — |

Note:
Cp represents cyclopropyl.

REFERENCE EXAMPLE 37

Magnesium turnings (0.46 g) were suspended in methanol and carbon tetrachloride (0.5 ml) was added. The mixture was stirred and heated at reflux for 10 minutes. t-Butyl 3-cyclopropyl-3-oxopropionate (3.5 g) was added and the mixture was stirred and heated at reflux for 0.5 hours. After cooling, the solution was evaporated to dryness and the residue was dissolved in toluene. The solution was evaporated to dryness and the residue was redissolved in toluene. 4-Methyl-2-(methylsulphonyl)benzoyl chloride (4.0 g) was added to the toluene solution and the mixture was stirred overnight. Aqueous hydrochloric acid (2M) was added and the resulting layers were separated. The organic layer was dried by azeotropic removal of water. 4-Toluenesulphonic acid (0.3 g) was added and the mixture was stirred and heated at reflux for 5 hours. After cooling, the mixture was washed with water, dried (anhydrous magnesium sulphate) and filtered. The filtrate was evaporated to dryness and the residue was triturated with a mixture of petroleum spirit and ether to give 3-cyclopropyl-1-[4-methyl-2-(methylsulphonyl)phenyl]propan-1,3-dione (3.8 g) as a brown solid, m.p. 129°–131° C.

By proceeding in a similar manner the following compounds were prepared from the appropriately substituted starting materials:

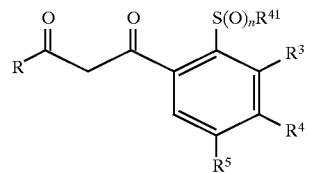

| R | $R^3$ | $R^4$ | $R^5$ | $R^{41}$ | n | mp/NMR (CDCl$_3$) |
|---|---|---|---|---|---|---|
| Cp | H | MeO | H | Me | 2 | 101° C. |
| Cp | H | Cl | H | Me | 0 | NMR (a) |
| Cp$^{70}$ | Cl | Cl | H | Me | 0 | 57–58.5 |
| Cp | F | Cl | H | Me | 0 | — |
| Cp | Me | Me | H | Me | 0 | NMR (b) |
| Cp | OMe | Cl | H | Me | 0 | NMR (c) |
| Cp | Cl | Br | H | Me | 0 | NMR (d) |

Note:
Cp represents cyclopropyl.
(a) NMR (CDCl$_3$): 0.7–1.35(m, 4H), 1.4–1.9(m, 1H), 2.4(s, 3H), 6.1(s, 1H), 7.0–7.9(m, 3H).
(b) NMR (CDCl$_3$); 0.8(m, 2H), 1.05(m, 2H), 1.6(m, 1H), 2.2(s, 3H), 2.25(s, 3H), 2.4(s, 3H), 5.8(s, 1H), 7.05(s, 2H), 15.75–16.0(bs, 1H).
(c) NMR (CDCl$_3$): 0.8–1.4(m, 4H), 1.5–1.9(m, 1H), 2.45(s, 3H), 4.0(s, 3H), 6.0(s, 1H), 7.15(d, 1H).
(d) NMR (CDCl$_3$): 1.0(m, 2H), 1.2(m, 2H), 1.75(m. 1H), 2.5(s, 3H), 5.95(s, 1H), 7.2(d, 1H), 7.65(d, 1H), 15.7–16.1(bs, 1H).

REFERENCE EXAMPLE 38

Carbon tetrachloride (2 ml) was added to a mixture of magnesium (0.57 g) and t-butyl 3-cyclopropyl-3-oxopropionate (4.36 g) in methanol. The mixture was stirred for 0.5 hours. It was evaporated to dryness and the residue was dissolved in toluene. The solution was evaporated to dryness and the residue was suspended in acetonitrile. 4-Chloro-2-(methylsulphonyl)benzoyl chloride (6.0 g) was added and the mixture was stirred for 3 hours. It was evaporated to dryness and the residue was dissolved in ethyl acetate. The mixture was washed with aqueous hydrochloric acid (2M), water, dried (anhydrous magnesium sulphate) and filtered. The filtrate was evaporated to dryness to give t-butyl 2-[4-chloro-2-(methylsulphonyl)benzoyl]-3-cyclopropyl-3-oxopropionate (9.6 g) as a brown oil which was not further purified.

By proceeding in a similar manner the following compounds were prepared from the appropriately substituted starting materials:

| R | $R^3$ | $R^4$ | $R^5$ | $R^{41}$ | n |
|---|---|---|---|---|---|
| Cp | H | H | H | Me | 2 |
| Cp | H | H | H | Et | 2 |
| Cp | H | H | H | isoPr | 2 |
| 1-MeCp | H | Cl | H | Me | 2 |
| IsoPr | H | Cl | H | Me | 2 |
| Cp | H | Br | H | Me | 2 |
| Cp | H | CF$_3$ | H | Me | 2 |
| Cp$^{72}$ | H | CF$_3$ | H | secBu | 0 |
| Cp | H | CF$_3$ | H | nPr | 0 |

Note:
Cp represents cyclopropyl.

Benzoyl chlorides were prepared by heating the appropriately substituted benzoic acids at reflux with thionyl chloride for 3 hours. The excess thionyl chloride was removed by evaporation and the benzoyl chlorides were used directly without further purification.

REFERENCE EXAMPLE 39

Potassium permanganate (316 g) was added with stirring to a suspension of 4-bromo-2-(methylsulphenyl)toluene (90.5 g) in water whilst maintaining the mixture at reflux. The mixture was stirred and heated at reflux for 3 hours. The mixture was filtered and the residue was washed with hot water. The filtrate was cooled to room temperature and extracted with ethyl acetate. The aqueous solution was acidified to pH 1, saturated with sodium chloride and extracted with ethyl acetate. The organic layer was washed with water, dried (anhydrous magnesium sulphate) and filtered. The filtrate was evaporated to dryness to give 4-bromo-2-(methylsulphonyl)benzoic acid (44.6 g) as a light brown solid, m.p. 220°–220.5° C.

By proceeding in a similar manner the following compounds were prepared from the appropriately substituted starting materials:

4-chloro-2-(methylsulphonyl)benzoic acid; NMR (CDCl$_3$+DMSO-d6): 3.34 (s,3H), 7.5–7.8(m,2H), 7.9 (s,1H), 8.2–8.6 (bs,1H).

REFERENCE EXAMPLE 40

Hydrogen peroxide (30%) was added to a cooled solution of 2-(methylsulphenyl)-4-trifluoromethylbenzoic acid (6.0 g) and acetic anhydride (3.6 ml) in acetic acid at 10° C. The mixture was allowed to warm slowly to room temperature and stirred for 0.5 hours. It was stirred and heated at 65° C. for 3 hours. After cooling, the mixture was poured into ice and extracted with ether. The organic layer was washed with water, aqueous ferrous sulphate solution, dried (anhydrous magnesium sulphate) and filtered. The filtrate was evaporated to dryness to give 2-(methylsulphonyl)-4-trifluoromethylbenzoic acid (5.54 g) as a white solid, m.p. 155.5°–156.5° C.

REFERENCE EXAMPLE 41

A solution of potassium peroxymonosulphate (23.8 g) in water was added to a solution of 4-methyl-2-(methylsulphenyl)benzoic acid (4.7 g) in methanol. The mixture was stirred for 5 hours and left to stand overnight at room temperature. The methanol was removed by evaporation and the resulting suspension was diluted with water and extracted with chloroform. The organic layer was dried (anhydrous magnesium sulphate) and filtered. The filtrate was evaporated to dryness and the residue was triturated with a mixture of ether and cyclohexane to give 4-methyl-2-(methylsulphonyl)benzoic acid (4.4 g) as a cream solid, m.p. 174°–174.5° C.

By proceeding in a similar manner the following compound was prepared from the appropriately substituted starting material:

4-methoxy-2-(methylsulphonyl)benzoic acid, m.p. 180°–180.5° C.

REFERENCE EXAMPLE 42 n-Butyllithium (2.5M solution in hexane; 25 ml) was added under an inert atmosphere to a stirred solution of 4-bromo-3-(methylsulphenyl)benzotrifluoride (16.4 g) in ether whilst maintaining the temperature below −70° C. The mixture was stirred at −70° C. for 2 hours and then poured onto solid carbon dioxide pellets. The mixture was stirred for 10 minutes and aqueous hydrochloric acid was added. The layers were separated and the aqueous layer was extracted with ether. The combined organic layers were washed with water, dried (anhydrous magnesium sulphate) and filtered. The filtrate was evaporated and the residue was triturated with cyclohexane and filtered to give 2-(methylsulphenyl)-4-trifluoromethylbenzoic acid (12.4 g) as a white solid, NMR (CDCl$_3$)+DMSO-d$_6$): 2.45 (s,3H), 7.2(d,1H), 7.3(s,1H), 8.0(d,1H), 10.7–11.1(bs,1H).

By proceeding in a similar manner the following compound was prepared from the appropriately substituted starting material:

4-methyl-2-(methylsulphenyl)benzoic acid m.p. 178.5°–179° C.

REFERENCE EXAMPLE 43 t-Butyl nitrite (4 ml) was added to a mixture of 5-chloro-2-methylaniline (4 g) and dimethyl disulphide (26.3 g) in chloroform. After the reaction started t-butyl nitrite (17.7 ml) and 5-chloro-2-methylaniline (16 g) were added simultaneously. The mixture was stirred at room temperature for 2 hours and left to stand overnight. The mixture was washed with water, aqueous hydrochloric acid (2M), water, dried (anhydrous magnesium sulphate) and filtered. The filtrate was evaporated to dryness to give 4-chloro-2-(methylsulphenyl)toluene (24.6 g) as a red oil, NMR (CDCl$_3$): 2.2 (s,3H), 2.4 (s,3H), 6.85 (s,2H), 7.0 (s,1H).

By proceeding in a similar manner the following compounds were prepared from the appropriately substituted starting materials:

4-bromo-3-(methylsulphenyl)benzotrifluoride, b.p. 84°–88° C. at 2 mm Hg;

4-bromo-3-(methylsulphenyl)toluene, b.p. 118°–124° C. at 7 mm Hg;

REFERENCE EXAMPLE 44

A cooled solution of sodium nitrite (5.8 g) in concentrated sulphuric acid (50 ml) was added to a stirred solution of 4-methyl-3-(methylsulphenyl)aniline (12.8 g) in glacial acetic acid at 20° C. The resulting suspension was added to a mixture of copper (I) bromide (12 g), aqueous hydrobromic acid (48.50%) and ice. The mixture was stirred at room temperature for 3 hours then diluted with water and extracted with ethyl acetate. The organic layer was washed with water, aqueous sodium hydroxide (2M), dried (anhydrous magnesium sulphate) and filtered. The filtrate was evaporated to dryness. The residue was triturated with hot cyclohexane and filtered. The filtrate was evaporated to dryness to give 4-bromo-2-(methylsulphenyl)toluene (8.6 g) as a brown oil, NMR (CDCl$_3$): 2.15(s,3H), 2.2(s,3H), 6.5–7.1 (m,3H).

REFERENCE EXAMPLE 45

Concentrated hydrochloric acid (128 ml) was added slowly to a suspension of 2-(methylsulphenyl)-4-nitrotoluene (36.6 g) in methanol. Iron powder (36 g) was added with stirring whilst maintaining the temperature below 50° C. The mixture was stirred at room temperature for 4 hours. The mixture was poured into water neutralized (by the addition of sodium carbonate), filtered and the residue was extracted with dichloromethane. The aqueous layer was extracted with dichloromethane and the combined organic layers were washed with aqueous sodium chloride solution, dried (anhydrous magnesium sulphate) and filtered. The filtrate was evaporated to dryness and the residue was purified by column chromatography on silica eluted with a mixture of ethyl acetate and n-hexane to give 4-methyl-3-(methylsulphenyl)aniline (12.8 g) as an orange solid, NMR (CDCl$_3$) 2.2(s,3H), 2.35(s,3H), 3.45(s,2H), 6.1–6.9(m,3H).

REFERENCE EXAMPLE 46

A solution of sodium nitrite (4.53 g) in water was added to a stirred suspension of 3,4-dichloroanthranillic acid (15 g) in acetic acid and concentrated hydrochloric acid while maintaining the temperature below 5° C. The mixture was stirred at below 5° C. for 2 hours then poured into a solution of dimethyl disulphide (8.4 g) and copper powder (0.1 g) in acetic acid. The mixture was stirred at room temperature for 1 hour and poured into water. The solid was filtered off, dried and recrystallized from cyclohexane to give 3,4-dichloro-2-(methylsulphenyl)benzoic acid (12.02 g) as a pale yellow solid, NMR (DMSO-D$_6$) 2.4(s,3H), 7.5(d,1H), 7.7(d,1H), 13.5(bs,1H).

REFERENCE EXAMPLE 47 n-Butyl lithium (2.5M in hexane; 180 ml) was added with cooling to a solution of 4-chloro-3-fluorobenzoic acid (37.5 g) in dry tetrahydrofuran while maintaining the temperature below −40° C. The mixture was stirred at −30° to −40° C. for 3 hours. Dimethyl disulphide (60.5 g) was added and the mixture was stirred at −40° C. for 0.5 hours and at room temperature overnight. Hydrochloric acid (2M) was added and the layers were separated. The aqueous layer was extracted with ether and the combined organic layers were extracted with aqueous sodium hydroxide (2M) and water. The aqueous extracts were combined and acidified to pH 1 and extracted with ether, washed with water, dried (Na$_2$SO$_4$) and filtered. The filtrate was evaporated to dryness and the residue was triturated with n-hexane and filtered to give 4-chloro-3-fluoro-2-methylsulphenylbenzoic acid (32.84 g) as a yellow solid, m.p. 149.5°–150.5° C.

REFERENCE EXAMPLE 48

A solution of potassium carbonate (10.67 g) in water was added to a solution of ethyl 3,4-dimethyl-2-methylsulphenylbenzoate (21.19 g) in ethanol. The mixture was heated at reflux for 0.5 hours then partially evaporated. Water was added and the mixture was acidified to pH 1. The solid was filtered off and washed with water to give 3,4-dimethyl-2-methylsulphenylbenzoic acid (18.39 g) as a white solid, m.p. 117.8°–120.3° C.

REFERENCE EXAMPLE 49

A solution of methanethiol (22 ml) in dry dimethyl formamide was added to a mixture of ethyl 3,4-dimethyl-2-nitrobenzoate (21.54 g) and potassium carbonate (20.02 g) in dry dimethyl formamide while maintaining the temperature below −15° C. The mixture was stirred at −10° C. for 0.5 hours and at room temperature for 3 days. Water was added and the mixture was extracted with ether, washed with water, dried (MgSO$_4$) and filtered. The filtrate was evaporated to dryness and the residue was purified by chromatography eluted with a mixture of ethyl acetate and hexane (8:1) to give ethyl 3,4-dimethyl-2-methylsulphenylbenzoate (21.25 g) as a clear oil, NMR (CDCl$_3$) 1.4(t,3H), 2.3(s,3H), 2.35(s,3H), 2.55(s,3H), 4.4(q,2H), 7.1(d,1H), 7.2(d,1H).

REFERENCE EXAMPLE 50

A mixture of 2-[4-chloro-3-methoxy-2-(methylsulphenyl) phenyl]-4,4-dimethyloxazoline (9.0 g) and hydrochloric acid (5M) was stirred and heated at reflux for 5 hours. After cooling, the mixture was diluted with water and extracted with dichloromethane. It was dried (magnesium sulphate), filtered and the filtrate was evaporated to dryness to give 4-chloro-3-methoxy-2-(methylsulphenyl) benzoic acid as a white solid, m.p. 98°–99° C.

REFERENCE EXAMPLE 51 n-Butyllithium (2.5M in hexane, 54 ml) was added with cooling to a stirred solution of 2-(4-chloro-3-methoxyphenyl)-4,4-dimethyloxazoline (27.0 g) in tetrahydrofuran while maintaining the temperature below −40° C. The mixture was stirred at −78° C. overnight. A solution of dimethyl disulphide (26.5 g) in tetrahydrofuran was added dropwise and the mixture was stirred at −40° C. overnight. After allowing to warm to room temperature the mixture was treated with hydrochloric acid (2M). The organic layer was washed with water, dried (magnesium sulphate) and filtered. The filtrate was evaporated to dryness and the residue was purified by dry column flash chromatography eluted with a mixture of ethyl acetate and n-hexane to give 2-[4-chloro-3-methoxy-2-(methylsulphenyl) phenyl]-4,4-dimethyloxazoline (11.1 g) as a white solid, m.p. 50°–52° C.

REFERENCE EXAMPLE 52 n-Butyllithium (2.5M in hexane; 8.8 ml) was added to a stirred cooled solution of di-isopropylamine (2.22 g) in dry tetrahydrofuran, maintaining the temperature below −40° C. The mixture was stirred for 0.5 hours then a solution of 4-bromo-3-chlorobenzoic acid (2.36 g) in dry tetrahydrofuran was added. The mixture was stirred at −40° C. for 6 hours. Dimethyl disulphide (2.82 g) was added and the mixture was stirred at −40° C. for 1 hour and at room temperature overnight. Hydrochloric acid (2M) was added and the layers were separated. The organic layer was washed with water, dried (magnesium sulphate) and filtered. The filtrate was evaporated to dryness and the residue was recrystallized from a mixture of ethyl acetate and hexane to give 4-bromo-3-chloro-2-methylsulphenylbenzoic acid (0.98 g) as a solid, m.p. 128°–130° C.

REFERENCE EXAMPLE 53

A solution of 2-(1-methylpropylsulphenyl)-4-trifluoromethylbenzonitrile (8.6 g) in ethanol was added to a solution of sodium hydroxide (47.3 g) in water and the resultant mixture was heated at reflux for 24 hours. It was poured into water and acidified to pH 1. The mixture was extracted with ethyl acetate, washed with water, dried (MgSO$_4$) and filtered. The filtrate was evaporated to dryness to give 2-(1-methylpropylsulphenyl)-4-trifluoromethylbenzoic acid (8.1 g) as a white solid, m.p. 99.8°–101° C.

By proceeding in a similar manner 2-propylsulphenyl-4-trifluoromethylbenzoic acid, m.p. 141.2°–142.2° C. was prepared from the appropriately substituted starting material.

REFERENCE EXAMPLE 54

A mixture of 2-nitro-4-trifluoromethylbenzonitrile (10.8 g), 1-methyl-1-propanethiol (7.5 g) and potassium carbonate (8.3 g) in acetonitrile was stirred and heated at reflux for 8 hours. It was cooled, water was added and the layers were separated. The aqueous layer was extracted with ethyl acetate and the combined organic layers were washed with water, dried (magnesium sulphate) and filtered. The filtrate was evaporated to dryness and the residue was purified by chromatography eluted with a mixture of ethyl acetate and cyclohexane to give 2-(1-methylpropylsulphenyl)-4-trifluoromethylbenzonitrile (11.2 g) as a yellow oil NMR (CDCl$_3$); 1.0(t,3H), 1.35(d,3H), 1.7(m,2H), 3.45(m,1H), 7.5 (d,1H), 7.7(s,1H), 7.75(d,1H).

By proceeding in a similar manner 2-propylsulphenyl-4-trifluoromethylbenzonitrile, NMR(CDCl$_3$) 1.0(t,3H), 1.7(m,2H), 3.0(t,2H), 7.4(d,1H), 7.5(s,1H), 7.65(d,1H), was prepared from the appropriately substituted starting material.

REFERENCE EXAMPLE 55

Cyanoacetic acid (8.5 g) was dissolved in dry THF (300 ml), placed under an inert atmosphere and the solution cooled using a dry ice-acetone bath. Butyllithium (80 ml of a 2.5M solution in hexane) was added dropwise over 1 hour. During the addition the internal reaction temperature was maintained below −65° C. The reaction mixture was stirred in the dry ice-acetone bath for 1 hour and then the bath was removed and the reaction stirred for an additional hour, during which time the internal temperature rose to −45° C. The resultant reaction mixture was cooled to −70° C. and trimethylacetyl chloride (6.0 g) in THF (50 ml) added dropwise over 30 minutes while keeping the temperature of the reaction mixture below −65° C. The reaction mixture was allowed to stir in a dry ice-acetone bath for 1 hour and then allowed to warm to room temperature overnight. The resultant mixture was acidified by the addition of 2N HCl (200 ml) and diluted with CH$_2$Cl$_2$ (500 ml). The layers were separated and the aqueous layer was extracted with CH$_2$Cl$_2$. The combined organic layers were dried (MgSO$_4$) and, after removal of the drying agent by filtration, the solvents were removed. The residue was dissolved in ether (200 ml) and the etheral solution extracted with 2N NaOH (twice with 50 ml portions). To the combined aqueous extracts was added conc. HCl to adjust the solution to pH 1. The resulting mixture was extracted with ether. The combined extracts were dried (MgSO$_4$) and, after removal of the drying agent by filtration, the solvents were removed to afford 5.6 g of 4,4-dimethyl-3-oxopentanonitrile as an orange oil which slowly solidified; m.p. 60° C.

REFERENCE EXAMPLE 56

Cyanoacetic acid (8.5 g) was dissolved in dry THF (250 ml), placed under an inert atmosphere and the solution was cooled using a dry ice-acetone bath. Butyl lithium (80 ml of a 2.5M solution in hexane) was added dropwise over 1 hour. During the addition the internal reaction temperature was maintained below −65° C. The reaction mixture was stirred in the dry ice-acetone bath for 1 hour, the cooling bath removed, and the reaction stirred for an additional hour during which time the internal temperature rose to 15° C. The resultant reaction mixture was cooled to −70° C. and cyclopropane-carbonyl chloride (5.2 g) in THF (50 ml) added dropwise over 20 min. while keeping the temperature of the reaction mixture below −65° C. The reaction mixture was thus stirred for 1 hour, and then allowed to warm to room temperature overnight. The resultant mixture was acidified by the addition of 2N HCl (200 ml) and then diluted with dichloromethane (500 ml). The layers were separated and the aqueous layer was extracted with dichloromethane. The combined organic layers were dried, filtered; the solvents were removed to give 7.5 g of an orange oil. The crude product was chromatographed on silica gel to afford 4.0 g of 3-cyclopropyl-3-oxopropanonitrile as a pale orange oil, NMR (CDCl$_3$): d 0.9–1.3 (m, 4H), 1.9–2.1 (m, 1H), 3.66 (s, 2H).

REFERENCE EXAMPLE 57

Triethylamine (0.9 g) was added to a mixture of 1-[2-chloro-4-(methylsulphonyl)phenyl]-3-cyclopropyl-2-ethoxymethylenepropan-1,3-dione (3.5 g) and hydroxylamine hydrochloride (1.0 g) in acetonitrile and the mixture was stirred at room temperature for 1 hour and left to stand overnight. The mixture was evaporated to dryness and the residue was partitioned between ethyl acetate and water. The organic layer was dried (magnesium sulphate) and filtered. The filtrate was evaporated to dryness and the residue was purified by column chromatography on silica eluted with ethyl acetate and toluene. The product was recrystallized from ethyl acetate and cyclohexane to give 4-[2-chloro-4-(methylsulphonyl)benzoyl]-5-cyclopropylisoxazole (0.98 g) as a white solid, m.p. 116° C.

By proceeding in a similar manner the following compounds were prepared from the appropriately substituted starting materials.

| R | R$^2$ | R$^3$ | R$^5$ | R$^{41}$ | n | m.p. |
|---|---|---|---|---|---|---|
| Cp | CF$_3$ | H | H | Me | 2 | 146° C. |
| Cp | Cl | OMe | H | Me | 2 | 94° C. |

Cp represents cyclopropyl.

REFERENCE EXAMPLE 58

Sodium acetate (7.87 g) was added to a stirred mixture of 3-cyclopropyl-2-ethoxymethylene-1-[2-methoxy-4-(methylsulphenyl)phenyl]propan-1,3-dione (30.6 g) and hydroxylamine hydrochloride (8.0 g) in ethanol. The mixture was stirred at room temperature overnight, then evaporated to dryness. The residue was dissolved in ethyl acetate, washed with water, dried (anhydrous magnesium sulphate) and filtered. The filtrate was evaporated to dryness and the residue was triturated with ether and filtered to give 5-cyclopropyl-4-[2-methoxy-4-(methylsulphenyl)benzoyl]isoxazole as a white solid, m.p. 107.5°–108.5° C.

By proceeding in a similar manner the following compounds were prepared from the appropriately substituted starting materials.

| R | R$^2$ | R$^3$ | R$^5$ | R$^{41}$ | n | m.p./NMR |
|---|---|---|---|---|---|---|
| Et | Cl | H | H | Me | 2 | 90° C. |
| secBu | Cl | H | H | Me | 2 | 128° C. |
| nPr | Cl | H | H | Me | 2 | 113° C. |
| t-Bu | CF$_3$ | H | H | Me | 2 | 150° C. |
| 1-MeCp | CF$_3$ | H | H | Me | 2 | 142° C. |
| Me | CF$_3$ | H | H | Me | 2 | 92° C. |

-continued

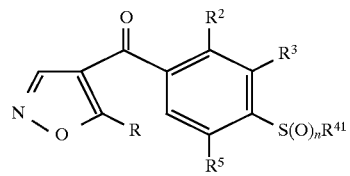

| R | R² | R³ | R⁵ | R⁴¹ | n | m.p./NMR |
|---|---|---|---|---|---|---|
| Cp | Cl | H | H | Me | 0 | NMR (a) |
| Cp | F | H | H | Me | 2 | 116° C. |
| Cp | Cl | H | H | Et | 2 | 102° C. |
| Cp | CF₃ | H | H | Me | 0 | 63° C. |
| Me | Br | MeO | H | Me | 2 | 104° C. |
| 1-MeCp | Cl | Cl | H | Me | 2 | 86° C. |
| Me | Cl | MeO | H | Me | 2 | 117° C. |
| Cp | Br | H | H | Me | 2 | 110° C. |
| 1-MeCp | Br | H | H | Me | 2 | 121° C. |
| 1-MeCp | CF₃ | H | H | Et | 2 | 126° C. |
| 1-MeCp | Cl | MeO | H | Me | 2 | 85° C. |
| Cp[85] | Br | MeO | H | Me | 0 | 86.4–87° C. |
| Cp | Br | MeO | H | Me | 2 | 130.2–131.4° C. |

Note:
Cp represents Cyclopropyl
(a) NMR (CDCl₃) 1.15(m, 2H) 1.25(m, 2H) 2.45(s, 3H) 2.55(m, 1H) 7.1(d, 1H) 7.2(s, 1H) 7.3(d, 1H) 8.15(s, 1H)

REFERENCE EXAMPLE 59

3-Chloroperbenzoic acid (1.3 g) was added to a solution of 4-[2-chloro-4-(methylsulphenyl)benzoyl]-5-cyclopropylisoxazole (2.0 g) in dichloromethane whilst maintaining the temperature below −15° C. The mixture was stirred at −15° C. for 2 hours and allowed to warm to room temperature. The mixture was stirred for 2 hours and then recooled to −15° C. 3-Chloroperbenzoic acid (0.7 g) was added and the mixture was stirred at −15° C. for 1 hour and at room temperature for 1 hour. A solution of sodium metabisulphite was added. The organic layer was washed with water, dried (magnesium sulphate) and filtered. The filtrate was evaporated to dryness and the residue was purified by column chromatography on silica eluted with ethyl acetate and hexane (3:2) to give 4-[2-chloro-4-(methylsulphinyl)benzoyl]-5-cyclopropylisoxazole (1.3 g) as a white solid, m.p.117° C.

By proceeding in a similar manner the following compounds were prepared from the appropriately substituted starting materials:

5-cyclopropyl-4-[4-(methylsulphinyl)-2-trifluoromethylbenzoyl]isoxazole, m.p.152° C.,
4-[2-bromo-3-methoxy-4-methylsulphinylbenzoyl]-5-cyclopropylisoxazole, m.p.111°–114.8° C.[87]

REFERENCE EXAMPLE 60

A mixture of 1-[2-chloro-4-(methylsulphonyl)phenyl]pentan-1,3-dione (7.0 g), triethyl orthoformate (7.2 g) and acetic anhydride was stirred and heated at reflux for 4 hours. The mixture was cooled and evaporated to dryness. Toluene was added to the residue and then re-evaporated to give 1-[2-chloro-4-(methylsulphonyl)phenyl]-2-ethoxymethylenepentan-1,3-dione (7.18 g) as a sticky orange solid which was not purified further.

By proceeding in a similar manner the following compounds were prepared from the appropriately substituted starting materials.

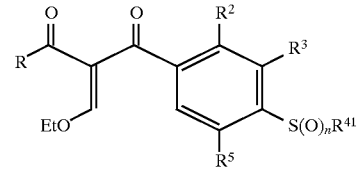

| R | R² | R³ | R⁵ | R⁴¹ | n |
|---|---|---|---|---|---|
| sec-Bu | Cl | H | H | Me | 2 |
| n-Pr | Cl | H | H | Me | 2 |
| t-Bu | CF₃ | H | H | Me | 2 |
| 1-MeCp | CF₃ | H | H | Me | 2 |
| Me | CF₃ | H | H | Me | 2 |
| Cp | Cl | H | H | Me | 0 |
| Cp | F | H | H | Me | 2 |
| Cp | Cl | H | H | Et | 2 |
| Cp | CF₃ | H | H | Me | 0 |
| Cp | OMe | H | H | Me | 0 |
| Me | Br | OMe | H | Me | 2 |
| 1-MeCp | Cl | Cl | H | Me | 2 |
| Cp | Cl | OMe | H | Me | 2 |
| Me | Cl | OMe | H | Me | 2 |
| Cp | Br | H | H | Me | 2 |
| 1-MeCp | Br | H | H | Me | 2 |
| 1-MeCp | CF₃ | H | H | Et | 2 |
| 1-MeCp | Cl | OMe | H | Me | 2 |
| Cp | Br | MeO | H | Me | 0 |
| Cp | Br | MeO | H | Me | 2 |

Note: Cp represents cyclopropyl

REFERENCE EXAMPLE 61

A mixture of crude t-butyl 2-[2-chloro-4-(methylsulphonyl)benzoyl]-3-oxopentanoate (12.0 g) and 4-toluenesulphonic acid (0.1 g) in toluene was stirred and heated at reflux for 3.5 hours. After cooling, the mixture was washed with water, dried (MgSO₄) and filtered. The filtrate was evaporated to dryness and the residue was triturated with ether and filtered to give 1-[2-chloro-4-(methylsulphonyl)phenyl]pentan-1,3-dione (7.02 g) as a white solid NMR(CDCl₃): 1.2(t,3H) 2.45 (q,2H) 3.0(s,3H) 5.9(s,1H) 7.5–8.0(m,3H).

By proceeding in a similar manner the following compounds were prepared from the appropriately substituted starting materials:

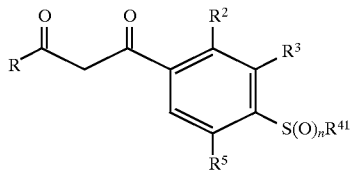

| R | $R^2$ | $R^3$ | $R^5$ | $R^{41}$ | n | m.p./NMR(CDCl$_3$) |
|---|---|---|---|---|---|---|
| secBu | Cl | H | H | Me | 2 | NMR:0.7–1.7(m, 8H)2.4(m, 1H) 3.05(s, 3H)5.9(s, 1H)7.5–7.9(m, 3H) |
| n-Pr | Cl | H | H | Me | 2 | NMR:1.0(t, 3H)1.7(m, 2H)2.3(t, 2H) 3.0(s, 3H)5.9(s, 1H)7.5–7.9(m, 3H) |
| t-Bu | CF$_3$ | H | H | Me | 2 | NMR:1.2(s, 9H)3.0(s, 3H)5.7(s, 1H) 7.5(d, 1H)7.9(d, 1H)8.1(s, 1H) |
| 1-MeCp | CF$_3$ | H | H | Me | 2 | NMR:0.8(m, 2H)1.2(m, 5H) 3.0(s, 3H)5.6(s, 1H)7.5(d, 1H) 7.9(d, 1H)8.0(s, 1H) |
| Me | CF$_3$ | H | H | Me | 2 | NMR(CDCl$_3$):2.2(s, 3H)3.1(s, 3H) 5.8(s, 1H)7.75(d, 1H)8.15(d, 1H) 8.3(s, 1H) |
| Cp | Cl | H | H | Me | 0 | NMR:0.8–1.3(m, 4H)1.6–1.9(m, 1H) 2.5(s, 3H)6.1(s, 1H)6.9–7.6(m, 3H) |
| Cp | F | H | H | Me | 2 | NMR:0.9–1.3(m, 4H)1.7–2.1(m, 1H) 3.05(s, 3H)6.3(s, 1H)7.4–8.0(m, 3H) |
| Cp | Cl | H | H | Et | 2 | NMR:0.9–1.4(m, 7H)1.5–1.9(m, 1H) 3.1(q, 2H)6.0(s, 1H)7.5–7.9(m, 3H) |
| Cp | CF$_3$ | H | H | Me | 0 | m.p. 68.5° C. |
| Cp | OMe | H | H | Me | 0 | NMR:0.7–1.2(m, 4H)1.4– 1.9(m, 1H)2.4(s, 3H)3.75(s, 3H) 6.45(s, 1H)6.6(s, 1H)6.65(d, 1H) 7.65(d, 1H) |
| Me | Br | OMe | H | Me | 2 | NMR:1.6(s, 3H)2.7(s,3H)3.6(s, 3H) 5.4(s, 1H)6.95(d, 1H)7.6(d, 1H) |
| Cp | Cl | OMe | H | Me | 2 | NMR:0.9–1.3(m, 4H)1.4–1.9(m, 1H) 3.2(s, 3H)4.0(s, 3H)5.95(s, 1H) 7.3(d, 1H)7.85(d, 1H) |
| Cp | Br | OMe | H | Me | 0 | NMR:1.2(m, 4H)1.7(m, 1H) 2.4(s, 3H)3.8(s, 3H)5.9(s, 1H) 7.0(m, 2H) |
| Cp | Br | OMe | H | Me | 2 | NMR:1.1(m, 4H)1.6(m, 1H) 3.2(s, 3H)4.0(s, 3H)5.8(s, 1H) 7.15(d, 1H)7.75(d, 1H) |

Note: Cp represents cyclopropyl.

REFERENCE EXAMPLE 62

Magnesium (1.56 g) was suspended in methanol and carbon tetrachloride (1 ml) was added. The mixture was warmed gently to initiate the reaction. t-Butyl 3-oxopentanoate was added and the mixture was stirred at room temperature for 1 hour and at 50° C. for 0.75 hours. The mixture was evaporated to dryness, toluene was added and it was re-evaporated. The residue was dissolved in dichloromethane and a solution of 2-chloro-4 (methylsulphonyl)benzoyl chloride (14.57 g) in dichloromethane was added. The mixture was stirred at room temperature overnight. Hydrochloric acid (2M) was added and the layers were separated. The organic layer was washed with water, dried (MgSO$_4$) and filtered. The filtrate was evaporated to dryness to give crude t-butyl 2-[2-chloro-4-(methylsulphonyl)benzoyl]-3-oxopentanoate (12.03 g) which was not purified further.

By proceeding in a similar manner the following compounds were prepared from the appropriately substituted starting materials.

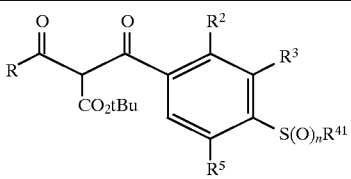

| R | $R^2$ | $R^3$ | $R^5$ | $R^{41}$ | n | Solvent |
|---|---|---|---|---|---|---|
| sec-Bu | Cl | H | H | Me | 2 | |
| n-Pr | Cl | H | H | Me | 2 | |
| t-Bu | CF$_3$ | H | H | Me | 2 | |
| 1-MeCp | CF$_3$ | H | H | Me | 2 | |
| Me | CF$_3$ | H | H | Me | 2 | |
| Cp | Cl | H | H | Me | 0 | CH$_2$Cl$_2$ replaced by MeCN |
| Cp | F | H | H | Me | 2 | CH$_2$Cl$_2$ replaced by MeCN |
| Cp | Cl | H | H | Et | 2 | CH$_2$Cl$_2$ replaced by MeCN |
| Cp | CF$_3$ | H | H | Me | 0 | CH$_2$Cl$_2$ replaced by MeCN |
| Cp | OMe | H | H | Me | 0 | CH$_2$Cl$_2$ replaced by MeCN |
| Me | Br | OMe | H | Me | 2 | CH$_2$Cl$_2$ replaced by MeCN |
| Cp | Cl | OMe | H | Me | 2 | CH$_2$Cl$_2$ replaced by MeCN |
| Cp | Br | OMe | H | Me | 0 | CH$_2$Cl$_2$ replaced by MeCN |
| Cp | Br | OMe | H | Me | 2 | CH$_2$Cl$_2$ replaced by MeCN |

Note: Cp represents cyclopropyl.

REFERENCE EXAMPLE 63

Magnesium (2.0 g) was suspended in methanol and carbon tetrachloride (1 ml) was added. The mixture was warmed to initiate the reaction. t-Butyl 3-(1-methylcyclopropyl)-3-oxopropanoate (15.0 g) was added and the mixture was stirred and heated at reflux for 1 hour. It was cooled and evaporated to dryness. Toluene was added and it was re-evaporated to dryness. The residue was dissolved in toluene and 2,3-dichloro-4-(methylsulphonyl) benzoyl chloride was added. The mixture was stirred at room temperature overnight. Hydrochloric acid (2M) was added and the layers were separated. The organic layer was heated at reflux with azeotropic removal of water for 1 hour. The mixture was cooled and 4-toluenesulphonic acid (1.0 g) was added. The mixture was stirred and heated at reflux for 5 hours, cooled, washed with water, dried (magnesium sulphate) and filtered. The filtrate was evaporated to dryness and the residue was purified by chromatography on silica eluted with dichloromethane. The product was triturated with ether and filtered off to give 1-[2,3-dichloro-4-(methylsulphonyl)phenyl]-3-(1-methylcyclopropyl)propan-1,3-dione (8.0 g) as a cream solid, m.p. 143° C.

By proceeding in a similar manner the following compounds were prepared from the appropriately substituted starting materials.

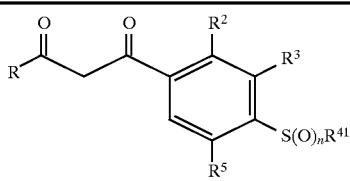

| R | $R^2$ | $R^3$ | $R^5$ | $R^{41}$ | n | m.p./NMR(CDCl$_3$) |
|---|---|---|---|---|---|---|
| Me | Cl | OMe | H | Me | 2 | m.p. 162.5° C. |
| Cp | Br | H | H | Me | 2 | m.p. 109° C. |
| 1-MeCp | Br | H | H | Me | 2 | NMR:0.7–1.0(m, 2H)1.2–1.5(m, 5H)3.1(s, 3H)5.95(s, 1H) 7.6(d, 1H)7.85(d, 1H)8.1(s, 1H) |
| 1-MeCp | CF$_3$ | H | H | Et | 2 | NMR:0.7–1.0(m, 2H)1.1–1.6(m, 8H)3.1(q, 2H) 5.75(s, 1H)7.6(d, 1H)8.0(d, 1H) 8.1(s, 1H) |
| 1-MeCp | Cl | OMe | H | Me | 2 | m.p. 123° C. |

Note: Cp represents cyclopropyl.

REFERENCE EXAMPLE 64

Potassium permanganate (119.2 g) was added to a stirred, heated suspension of crude 2-fluoro-4-(methylsulphenyl) toluene (25.37 g) in water at approximately 90°–100° C. The mixture was cooled slightly and filtered. The solid was washed thoroughly with hot water. The filtrate was extracted with dichloromethane. The aqueous layer was acidified to pH 1 and extracted with ethyl acetate. The organic extract was dried (MgSO$_4$) and filtered. The filtrate was evaporated to dryness to give 2-fluoro-4-(methylsulphonyl)benzoic acid (15.9 g) as an orange solid, m.p. 188° C.

REFERENCE EXAMPLE 65 t-Butyl nitrite (4 ml) was added to a mixture of 3-fluoro-4-methylaniline (5 g) and dimethyldisulphide (36 ml) in chloroform. After the reaction had initiated t-butyl nitrite (22 ml) and a solution of 3-fluoro-4-methylaniline (20.0 g) in chloroform were added simultaneously. The mixture was then stirred at room temperature for 2 hours. The mixture was washed with water, hydrochloric acid (2M), water, dried (MgSO$_4$) and filtered. The filtrate was evaporated to dryness to give 2-fluoro-4-(methylsulphenyl)toluene (25.37 g) as a red oil which was not further purified.

By proceeding in a similar manner the following compound was prepared from the appropriately substituted starting material:

2-bromo-5-(ethylsulphenyl)benzotrifluoride, b.p. 105°–112° C. at 7 mm Hg.

REFERENCE EXAMPLE 66

Hydrogen peroxide (30%, 62.3 ml) was added dropwise to a stirred, cooled solution of 4-(ethylsulphenyl)-2-trifluoromethylbenzoic acid (20 g) and acetic anhydride (10.1 ml) in acetic acid whilst maintaining the temperature below 10° C. The mixture was stirred at 0° C. for 1 hour, room temperature for 2 hours and heated at 70° C. for 2 hours. After cooling the mixture was poured onto ice and extracted with ethyl acetate. The organic extract was washed with water, aqueous ferrous sulphate solution, water, then dried (MgSO$_4$) and filtered. The filtrate was evaporated to dryness to give 4-(ethylsulphonyl)-2-trifluoromethylbenzoic acid (21.5 g) as an off-white solid, NMR (CDCl$_3$) 1.25(t,3H) 3.15(q,2H) 7.8(d,1H) 8.0(d,1H) 8.1(s,1H).

REFERENCE EXAMPLE 67

A solution of n-butyllithium in hexane (2.5M, 115 ml) was added dropwise with cooling to a stirred solution of 2-bromo-5-(ethylsulphenyl)benzotrifluoride (80.0 g) in anhydrous ether whilst maintaining the temperature below −70° C. The mixture was stirred at −78° C. for 1.5 hours and poured onto solid carbon dioxide pellets. The mixture was stirred for 20 minutes then treated with hydrochloric acid (2M). The layers were separated and the organic layer was washed with water, dried (MgSO$_4$) and filtered. The filtrate was evaporated to dryness. The residue was triturated with cyclohexane and filtered to give 4-(ethylsulphenyl)-2-trifluoromethylbenzoic acid as an off-white solid, m.p. 133.5° C.

REFERENCE EXAMPLE 68

A mixture of 3-cyclopropyl-2-(N,N-dimethylaminomethylene)-1-(4-methyl-3-methylsulphenylphenyl)propan-1,3-dione (10.6 g) and hydroxylamine hydrochloride (2.92 g) in ethanol was stirred at room temperature overnight. Water was added and the mixture was evaporated to remove the ethanol. It was extracted with ethyl acetate, washed with aqueous sodium chloride solution, dried (sodium sulphate) and filtered. The filtrate was evaporated to dryness and the residue was purified by chromatography on silica eluted with a mixture of ether and cyclohexane to give 5-cyclopropyl-4-(4-methyl-3-methylsulphenylbenzoyl)isoxazole (2.77 g) as a white solid, m.p. 85.5°–86.1° C.

REFERENCE EXAMPLE 69

3-Chloroperbenzoic acid (about 50%, 2.5 g) was added to a solution of 5-cyclopropyl-4-(4-methyl-3-methylsulphenylbenzoyl)isoxazole (0.8 g) in dichloromethane and the mixture was stirred at room temperature overnight. An aqueous solution of sodium metabisulphite was added and the mixture was stirred for 20 minutes. The solid was filtered and the filtrate layers separated. The organic phase was washed with aqueous sodium acetate, brine, dried and filtered. The filtrate was evaporated and the residue triturated with ether and filtered to give 5-cyclopropyl-4-(4-methyl-3-methylsulphonylbenzoyl) isoxazole (0.65 g) as a white solid, m.p. 126.4°–127.7° C.

By proceeding in a similar manner 5-cyclopropyl-4-(4-methyl-3-methylsulphinylbenzoyl)isoxazole was prepared.

REFERENCE EXAMPLE 70

Dimethyl formamide dimethyl acetal (6.0 ml) was added to a solution of 3-cyclopropyl-1-(4-methyl-3-methylsulphenylphenyl)propan-1,3-dione (8.71 g) in toluene. The mixture was stirred at room temperature overnight. Further dimethyl formamide dimethyl acetal (2.0 ml) was added and the mixture was stirred and heated at 50° C. for 24 hours. It was cooled and evaporated to dryness to give 3-cyclopropyl-2-(N,N-dimethylaminomethylene)-1-(4-methyl-3-methylsulphenylphenyl)propan-1,3-dione (10.6 g) as a brown oil.

REFERENCE EXAMPLE 71

A suspension of magnesium (2.4 g) in methanol was warmed gently to initiate the reaction and t-butyl 3-cyclopropyl-3-oxopropionate (18.4 g) was added. The mixture was stirred for 0.75 hours then the methanol was evaporated off. Toluene was added and the mixture was re-evaporated to remove the last traces of methanol. The residue was suspended in acetonitrile and a solution of 4-methyl-3-methylsulphenylbenzoyl chloride (20.0 g) in acetonitrile was added. The mixture was stirred at room temperature overnight. Hydrochloric acid (2M) was added and the mixture was stirred for 1 hour. It was extracted with ethyl acetate, washed with aqueous sodium chloride solution, dried (magnesium sulphate) and filtered. The filtrate was evaporated to dryness to give an orange oil. This was dissolved in toluene and 4-toluenesulphonic acid (1.5 g) was added. The mixture was heated at reflux for 4 hours. It was cooled to room temperature and evaporated to dryness.

The residue was dissolved in ethyl acetate and washed with water, aqueous sodium chloride solution, dried (magnesium sulphate) and filtered. The filtrate was evaporated to dryness. The residue was purified by chromatography eluted with a mixture of ethyl acetate and cyclohexane to give 3-cyclopropyl-1-(4-methyl-3-methylsulphenylphenyl)propan-1,3-dione (9.99 g) as a brown oil, NMR (CDCl$_3$) 0.9–1.05(m,2H), 1.15–1.25(m, 2H), 1.75–1.85(m,1H), 2.4(s,3H), 2.5(s,3H), 6.25(s,1H), 7.2 (d,1H), 7.5(d,1H), 7.65(s,1H), 16.2–16.4(bs,1H).

REFERENCE EXAMPLE 72

A solution of sodium nitrite (14.5 g) in water was added to a stirred, cooled suspension of 3-amino-4-methylbenzoic acid (30.23 g) in a mixture of acetic acid and concentrated hydrochloric acid at a temperature between 0° C. and 5° C. The mixture was stirred at 0°–5° C. for 1 hour and the resulting mixture was added to a stirred mixture of dimethyl disulphide (22 ml) and copper powder (0.25 g) in acetic acid while maintaining the temperature at about 35° C. Further copper powder (3 g) was added during the reaction in order to maintain the gas evolution. It was stirred for a further 1 hour then poured into water and the solid filtered off. It was treated with a mixture of ethyl acetate and cyclohexane, heated and the insoluble material was filtered off to give 4-methyl-3-methylsulphenylbenzoic acid (19.5 g) as a white solid, m.p. 174.6°–175.2° C.

According to a feature of the present invention, there is provided a method for controlling the growth of weeds (i.e. undesired vegetation) at a locus which comprises applying to the locus a herbicidally effective amount of at least one 2-cyano-1,3-dione derivative of general formula (I) or an agriculturally acceptable salt thereof. For this purpose, the 2-cyano-1,3-dione derivatives are normally used in the form of herbicidal compositions (i.e. in association with compatible diluents or carriers and/or surface active agents suitable for use in herbicidal compositions), for example as hereinafter described.

The compounds of general formula (I) show herbicidal activity against dicotyledonous (i.e. broad-leafed) and monocotyledonous (e.g. grass) weeds by pre- and/or, post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula (I) may be used to control the growth of broad-leafed weeds, for example, Abutilon theophrasti, *Amaranthus retroflexus, Bidens pilosa, Chenopodium album, Galium aparine*, Ipomoea spp. e.g. *Ipomoea purpurea, Sesbania exaltata, Sinapis arvensis, Solanum nigrum* and *Xanthium strumarium*, and grass weeds, for example *Alopecurus myosuroides, Avena fatua, Digitaria sanguinalis, Echinochloa crus-galli, Eleusine indica* and Setaria spp, e.g. *Setaria faberii* or *Setaria viridis*, and sedges, for example, *Cyperus esculentus*.

The amounts of compounds of general formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of general formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2 kg, of active material per hectare are particularly suitable.

The compounds of general formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5 kg, and preferably between 0.5 kg and 4 kg of active material per hectare.

The compounds of general formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1 kg and 20 kg, and preferably between 5 and 10 kg, of active material per hectare are particularly suitable for this purpose.

When used to control the growth of weeds by pre-emergence application, the compounds of general formula (I) may be incorporated into the soil in which the weeds are expected to emerge. It will be appreciated that when the compounds of general formula (I) are used to control the growth of weeds by post-emergence application, i.e. by application to the aerial or exposed portions of emerged weeds, the compounds of general formula (I) will also normally come into contact with the soil and may also then exercise a pre-emergence control on later-germinating weeds in the soil.

Where especially prolonged weed control is required, the application of the compounds of general formula (I) may be repeated if required.

According to a further feature of the present invention, there are provided compositions suitable for herbicidal use comprising one or more of the 2-cyano-1,3-dione derivatives of general formula (I) or an agriculturally-acceptable salt thereof in association with, and preferably homogeneously dispersed in, one or more compatible herbicidally-acceptable diluents or carriers and/or surface active agents [i.e. diluents or carriers and/or surface active agents of the type generally accepted in the art as being suitable for use in herbicidal compositions and which are compatible with compounds of general formula (I)]. The term "homogeneously dispersed" is used to include compositions in which the compounds of general formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula (I).

The herbicidal compositions may contain both a diluent or carrier and surface-active (e.g. wetting, dispersing, or emulsifing) agent. Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula (I) with solid diluents or by impregnating the solid diluents or carriers with solutions of the compounds of general formula (I) in volatile solvents, evaporating the solvents and, if necessary, grinding the products so as to obtain powders. Granular formulations may be prepared by absorbing the compounds of general formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of general formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are aqueous suspension concentrates which comprise from 10 to 70% of one or more compounds of general formula (I), from 2 to 10% of surface-active agent, from 0.1 to 5% of thickener and from 15 to 87.9% of water, wettable powders which comprise from 10 to 90% of one or more compounds of general formula (I), from 2 to 10% of surface-active agent and from 8 to 88% of solid diluent or carrier, soluble powders which comprise from 10 to 90% of one or more compounds of general formula (I), from 2 to 40% of sodium carbonate and from 0 to 88% of solid diluent, liquid water soluble concentrates which comprise from 5 to 50%, e.g. 10 to 30%, of one or more compounds of general formula (I), from 5 to 25% of surface-active agent and from 25 to 90%, e.g. 45 to 85%, of water miscible solvent, e.g. dimethylformamide, or a mixture of water-miscible solvent and water, liquid emulsifiable suspension concentrates which comprise from 10 to 70% of one or more compounds of general formula (I), from 5 to 15% of surface-active agent, from 0.1 to 5% of thickener and from 10 to 84.9% of organic solvent granules which comprise from 1 to 90%, e.g. 2 to 10% of one or more compounds of general formula (I), from 0.5 to 7%, e.g. 0.5 to 2%, of surface-active agent and from 3 to 98.5%, e.g. 88 to 97.5%, of granular carrier and, emulsifiable concentrates which comprise 0.05 to 90%, and preferably from 1 to 60% of one or more compounds of general formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of general formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2-dimethyl-3,5-diphenyl-pyrazolium salts], flampropmethyl [methyl N-2-(N-benzoyl-3-chloro-4-fluoroanilino)-propionate], fluometuron [N'-(3-trifluoro-methylphenyl)-N,N-dimethylurea], isoproturon [N'-(4-isopropylphenyl)-N,N-dimethylurea], nicosulfuron [2-(4,6-dimethoxypyrimidin-2-ylcarbamoylsulfamoyl)-N,N-dimethylnicotinamide] insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3- dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 2-cyano-1,3-dione derivatives of general formula (I) or an agriculturally-acceptable salt thereof or, as is preferred, a herbicidal composition as hereinbefore described, and preferably a herbicidal concentrate which must be diluted before use, comprising at least one of the 2-cyano-1,3-dione derivatives of general formula (I) within a container for the aforesaid derivative or derivatives of general formula (I), or a said herbicidal composition, and instructions physically associated with the aforesaid container setting out the manner in which the aforesaid derivative or derivatives of general formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the 2-cyano-1,3-dione derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A wettable powder is formed from:

active ingredient (compound 1): 50% w/w nonylphenol/ethylene oxide condensate containing 9 moles of ethylene oxide per mol of phenol: 5% w/w silicon dioxide of micro-fine particle size: 5% w/w synthetic magnesium silicate carrier: 40% w/w by absorbing the condensate on the silicon dioxide, mixing with the other ingredients and grinding the mixture in a hammermill to give a wettable powder.

Similar wettable powders may be prepared as described above by replacing the 2-cyano-1,3-dione (compound 1) by other compounds of formula (I).

EXAMPLE C2

An aqueous suspension concentrate is formed from:
active ingredient (compound 1): 50% w/v
nonylphenol/ethylene oxide condensate containing 9 moles of ethylene oxide per mol of phenol: 1% w/v
sodium salt of polycarboxylic acid: 0.2% w/v
Ethylene glycol: 5% w/v
polysaccharide xanthan gum thickener: 0.15% w/v
water to 100% by volume
 by intimately mixing the ingredients and grinding in a ball-mill for 24 hours.

Similar aqueous concentrates may be prepared as described above by replacing the 2-cyano-1,3-dione (compound 1) by other compounds of general formula (I).

EXAMPLE C3

A wettable powder is formed from:
Active ingredient (compound 611) 80% w/w
Sodium dodecylbenzene sulphonate 3% w/w
Sodium N-methyl-N-oleyl taurate 2% w/w
Sodium polycarboxylate 1% w/w
Microfine silicon dioxide 2% w/w
China clay 12% w/w
 by blending the above ingredients and grinding the mixture in an air jet mill.

Similar wettable powders may be prepared as described above by replacing the 2-cyano-1,3-dione (compound 611) with other compounds of formula I.

EXAMPLE C4

A suspension concentrate is formed from:
Active ingredient (compound 611) 60% w/v
Nonyl phenol 9 mole polyethoxylate 0.5% w/v
Triethanolamine salt of phosphated tristyryl phenol 16 mole polyethoxylate 1.5% w/v
Sodium polycarboxylate 0.4% w/v
polysaccharide gum 0.1% w/v
propylene glycol 5% w/v
silicone antifoam emulsion 0.01% w/v
1,2 benzisothiazolin-3-one solution in dipropylene glycol 0.01% w/v
water to 100 volumes
 by mixing using a high shear mixer all ingredients into 90% volume of water, then making up to volume with water, then milling the mixture by passing through a horizontal bead mill.

Similar suspension concentrates may be prepared as described above by replacing the 2-cyano-1,3-dione (compound 611) with other compounds of formula I.

EXAMPLE C5

A granule is formed from
Active ingredient (compound 611) 5% w/w
Sepiolite granules 30/60 mesh 95% w/w
 by dissolving the active ingredient in n-butanol, then spraying this solution onto sepiolite granules whilst mixing the granules in a tumbler-mixer then evaporating off the n-butanol to leave a granule containing 5% w/w active ingredient.

Similar granules may be prepared as described above by replacing the 2-cyano-1,3-dione (compound 611) with other compounds of formula I.

EXAMPLE C6

A water dispersible granule is formed from
Active ingredient (compound 611) 75% w/w
Sodium lignosulphonate 10% w/w
Sodium dialkylnaphthalene sulphonate 3% w/w
Clay 12% w/w
 by blending the above ingredients, then grinding the mixture in an air-jet mill, then adding water to form a kneadable paste, then extruding this paste to form fine filaments approximately 1 mm in diameter, chopping the extrudate into lengths of approximately 4 mm then drying these in a fluid bed drier.

Similar water dispersible granules may be prepared as described above by replacing the 2-cyano-1,3-dione (compound 611) with other compounds of formula I.

EXAMPLE C7

An emulsifiable concentrate is formed from
Active ingredient (compound 611) 10% w/w
Nonyl phenol 18 mole polyethoxylate/polypropoxylate 4–6% w/w
Calcium dodecylbenzene sulphonate, 70% in butanol 6–4% w/w
Light aromatic solvent to 100 volumes
by mixing using a high shear mixer all ingredients into 90% volume of water, then making up to volume with water, then milling the mixture by passing through a horizontal bead mill.

Similar suspension concentrates may be prepared as described above by replacing the 2-cyano-1,3-dione (compound 611) with other compounds of formula I.

Representative compounds of formula (I) have been used in herbicidal applications according to the following procedures.

Method of use of herbicidal compounds:
Herbicidal activity

Appropriate quantities of the compounds used to treat the plant were dissolved in acetone to give solutions equivalent to an application rate of up to 1000 g of the compounds used to treat the plants per hectare (g/ha). These solutions were applied at 260 liters of spray fluid per hectare.

a) Pre-emergence application weed control
 Seeds (weeds or crops) were sown in loam soil pots.
 The compounds of the invention were applied to the soil surface as described above.

b) Post-emergence application weed control
 Weed species were grown until ready for spraying with the compounds of the invention. The growth stage of the plants at spraying were as follows:

1) Broad-leafed weeds
 *Abutilon theophrasti:* 1–2 leaves.
 *Amaranthus retroflexus:* 1–2 leaves.
 *Galium aparine:* 1–2 whorls.
 *Sinapis arvensis:* 2 leaves.
 *Ipomoea purpurea:* 1–2 leaves.
 *Xanthium strumarium:* 2 leaves.
2) Grass weeds
 *Alopecurus myosuroides:* 2 leaves.

*Avena fatua:* 1–2 leaves.
*Echinochloa crus-galli* 2–3 leaves.
*Setaria viridis:* 2–3 leaves.
3) Sedges
*Cyperus esculentus:* 3 leaves.
c) Crop tolerance Compounds of the invention were applied pre-emergence as in (a) or post emergence (3-leaf stage) to the following crops:—wheat, maize, rice, soya and cotton.

A single pot of each plant species was allocated to each treatment with unsprayed controls and controls sprayed with acetone alone.

After treatment, the pots were kept in the greenhouse and were watered overhead.

Visual assessment of phytotoxicity was made 17–20 days after spraying. Weed control results were expressed as the percentage reduction in growth or kill of the weeds, in comparison with the plants in the control pots. Crop tolerance was expressed as the percentage damage to crop.

Representative compounds of the invention, when used at an application rate of 1 kg/ha or less, show herbicidal activity against one or more of the weed species listed above: such compounds also show selectivity on one or more of the listed crop species.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula

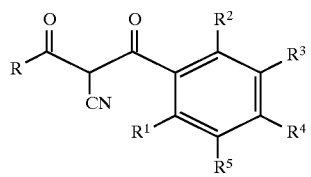

wherein:

R is:
straight- or branched-chain alkyl having up to six carbon atoms, optionally substituted by one or more halogen; or
cycloalkyl having from three to six carbon atoms, optionally bearing one or more $R^7$ substituents;

$R^1$ is hydrogen;

each of $R^2$, $R^3$, $R^4$ and $R^5$, which can be the same or different, is:
hydrogen;
straight- or branched-chain alkyl, alkenyl or alkynyl having up to six carbon atoms, optionally substituted by one or more halogen;
straight- or branched-chain alkyl having up to six carbon atoms, substituted by an —$OR^6$ group;
halogen;
phenyl, optionally substituted by from one to three $R^{21}$ groups, which can be the same or different; or
—$COR^7$, nitro, cyano, —$CO_2R^6$, —$S(O)_nR^9$, —$O(CH_2)_mOR^6$, —$N(R^{12})SO_2R^8$, —$CONR^{10}R^{15}$ or —$OR^{61}$;

provided that at least one of $R^2$, $R^3$, $R^4$ and $R^5$ is —$N(R^{12})SO_2R^8$;

$R^6$ is:
straight- or branched-chain alkyl, alkenyl or alkynyl having up to six carbon atoms, optionally substituted by one or more halogen; or
cycloalkyl having from three to six carbon atoms;

$R^{61}$ is:
straight- or branched-chain alkyl, alkenyl or alkynyl having up to six carbon atoms, optionally substituted by one or more halogen;
cycloalkyl having from three to six carbon atoms; or
phenyl, optionally substituted by from one to five $R^{21}$ groups, which can be the same or different;

$R^7$ is:
straight- or branched-chain alkyl having up to six carbon atoms, optionally substituted by one or more halogen; or
cycloalkyl having from three to six carbon atoms;

$R^8$ is:
straight- or branched-chain alkyl, alkenyl or alkynyl having up to six carbon atoms, optionally substituted by one or more halogen;
cycloalkyl having from three to six carbon atoms;
phenyl, optionally substituted by from one to five $R^{21}$ groups, which can be the same or different; or
—$NR^{10}R^{11}$;

$R^9$ is:
straight- or branched-chain alkyl, alkenyl or alkynyl having up to six carbon atoms, optionally substituted by one or more halogen;
cycloalkyl having from three to six carbon atoms; or
phenyl, optionally substituted by from one to five $R^{21}$ groups, which can be the same or different;

$R^{10}$ is:
hydrogen; or
straight- or branched-chain alkyl having up to six carbon atoms, optionally substituted by one or more halogen;

$R^{11}$ is:
straight- or branched-chain alkyl having up to six carbon atoms, optionally substituted by one or more halogen;
provided that when $R^{10}$ and $R^{11}$ are part of a group —$NR^{10}R^{11}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{12}$ is:
hydrogen;
straight- or branched-chain alkyl, alkenyl or alkynyl having up to six carbon atoms, optionally substituted by one or more halogen;
cycloalkyl having from three to six carbon atoms;
phenyl, optionally substituted by from one to five $R^{21}$ groups, which can be the same or different; or
—$OR^{17}$;

$R^{15}$ is:
$R^7$ or —$OR^{17}$;
provided that when $R^{10}$ and $R^{15}$ are part of a group —$CONR^{10}R^{15}$ they can, together with the nitrogen to which they are attached, form a 5 or 6 membered ring optionally having one additional hetero ring atom which is oxygen or nitrogen, said ring being optionally substituted by one or more alkyl, each having up to 3 carbon atoms;

$R^{17}$ is:

straight- or branched-chain alkyl having up to six
carbon atoms;
$R^{21}$ is:
halogen;
straight- or branched-chain alkyl having up to three carbon atoms, optionally substituted by one or more halogen; or
nitro, cyano, —S(O)$_n$R$^7$ or —OR$^7$;
m is one, two or three; and
n is zero, one or two;
or an agriculturally acceptable salt, metal complex or enolic tautomeric form thereof.

2. A compound according to claim 1, wherein:
R is:
straight- or branched-chain alkyl having up to six carbon atoms, optionally substituted by one or more halogen; or
cycloalkyl having from three to six carbon atoms, optionally bearing one or more methyl substituents;
each of R$^2$, R$^3$, R$^4$ and R$^5$, which can be the same or different, is:
hydrogen;
halogen;
straight- or branched-chain alkyl, alkenyl or alkynyl having up to six carbon atoms, optionally substituted by one or more halogen;
straight- or branched-chain alkyl having up to six carbon atoms, substituted by an —OR$^6$ group;
phenyl, optionally substituted by from one to three R$^{21}$ groups, which can be the same or different; or
—COR$^7$, cyano, nitro, —CO$_2$R$^6$, —S(O)$_n$R$^9$, —O(CH$_2$)$_m$OR$^6$, —N(R$^{12}$)SO$_2$R$^8$ or —OR$^{61}$;
each of R$^6$ and R$^7$, which can be the same or different, is:
straight- or branched-chain alkyl having up to six carbon atoms, optionally substituted by one or more halogen; or
cycloalkyl having from three to six carbon atoms;
each of R$^{61}$ and R$^9$, which can be the same or different, is:
straight- or branched-chain alkyl or alkenyl having up to six carbon atoms, optionally substituted by one or more halogen;
straight- or branched-chain alkynyl having from three to six carbon atoms; or
cycloalkyl having from three to six carbon atoms;
$R^8$ is:
straight- or branched-chain alkyl or alkenyl having up to six carbon atoms, optionally substituted by one or more halogen;
straight- or branched-chain alkynyl having from three to six carbon atoms;
cycloalkyl having from three to six carbon atoms; or
phenyl, optionally substituted by from one to three R$^{21}$ groups, which can be the same or different;
$R^{12}$ is:
hydrogen;
straight- or branched-chain alkyl or alkenyl having up to six carbon atoms, optionally substituted by one or more halogen;
straight- or branched-chain alkynyl having from three to six carbon atoms; or
cycloalkyl having from three to six carbon atoms;
$R^{21}$ is:
halogen;
straight- or branched-chain alkyl having up to three carbon atoms, optionally substituted by one or more halogen; or
nitro, cyano, —S(O)$_n$R$^7$ or —OR$^7$;
m is two or three; and
n is zero, one or two.

3. A compound according to claim 1, wherein:
R is:
straight- or branched-chain alkyl having up to three carbon atoms; or
cycloalkyl having three or four carbon atoms, optionally bearing a methyl substituent;
each of R$^2$, R$^3$ and R$^4$, which can be the same or different, is:
hydrogen, chlorine, bromine or fluorine;
straight- or branched-chain alkyl, alkenyl or alkynyl having up to four carbon atoms, optionally substituted by one or more halogen;
straight- or branched-chain alkyl having up to four carbon atoms, substituted by an —OR$^6$ group; or
—COR$^7$, —CO$_2$R$^6$, —S(O)$_n$R$^9$, —O(CH$_2$)$_m$OR$^6$, —N(R$^{12}$)SO$_2$R$^8$ or —OR$^{61}$;
$R^5$ is hydrogen;
each of R$^6$, R$^7$ and R$^9$, which can be the same or different, is:
straight- or branched-chain alkyl having up to four carbon atoms, optionally substituted by one or more chlorine, bromine or fluorine; or
cyclopropyl;
each of R$^{61}$ and R$^8$, which can be the same or different, is:
straight- or branched-chain alkyl or alkenyl having up to four carbon atoms, optionally substituted by one or more chlorine, bromine or fluorine;
straight- or branched-chain alkynyl having three or four carbon atoms; or
cyclopropyl;
$R^{12}$ is:
hydrogen;
straight- or branched-chain alkyl or alkenyl having up to four carbon atoms, optionally substituted by one or more chlorine, bromine or fluorine;
straight- or branched-chain alkynyl having three or four carbon atoms; or
cyclopropyl;
m is two or three; and
n is zero, one or two.

4. A compound according to claim 1, wherein:
R is methyl, ethyl, isopropyl, cyclopropyl or 1-methylcyclopropyl;
each of R$^2$, R$^3$ and R$^4$, which can be the same or different, is:
hydrogen, bromine, chlorine or fluorine;
straight- or branched-chain alkyl or alkenyl having up to four carbon atoms, optionally substituted by one or more chlorine, bromine or fluorine;
—COR$^7$, —CO$_2$R$^6$, —SR$^9$, —O(CH$_2$)$_m$OR$^6$, —OR$^{61}$ or —N(R$^{12}$)SO$_2$R$^8$; or
straight- or branched chain alkyl having up to four carbon atoms, substituted by —OR$^6$;
$R^5$ is hydrogen;
each of R$^6$, R$^7$ and R$^9$, which can be the same or different, is straight- or branched-chain alkyl having up to three carbon atoms;
$R^{61}$ is:
straight- or branched-chain alkyl having up to four carbon atoms, optionally substituted by one or more chlorine, bromine or fluorine;
straight- or branched-chain alkenyl or alkynyl having three or four carbon atoms; or cyclopropyl;

$R^8$ is:
straight- or branched-chain alkyl having up to three carbon atoms, optionally substituted by one or more chlorine, bromine, or fluorine; or
allyl, optionally substituted by one or more chlorine, fluorine or bromine;

$R^{12}$ is:
hydrogen;
straight- or branched-chain alkyl having up to three carbon atoms, optionally substituted by one or more chlorine, bromine or fluorine; or
allyl, optionally substituted by one or more chlorine, fluorine or bromine; and
m is two or three.

5. A compound of the formula

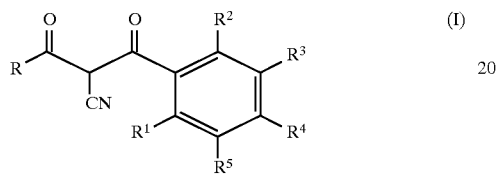

(I)

wherein:

R is:
straight- or branched-chain alkyl having up to six carbon atoms, optionally substituted by one or more halogen; or
cycloalkyl having from three to six carbon atoms, optionally substituted by one or more $R^7$ groups;

$R^1$ is hydrogen;

each of $R^2$, $R^3$, $R^4$ and $R^5$, which can be the same or different, is:
hydrogen;
halogen;
straight- or branched-chain alkyl, alkenyl or alkynyl having up to six carbon atoms, optionally substituted by one or more halogen;
phenyl, optionally substituted by from one to three $R^{21}$ groups, which can be the same or different;
straight- or branched-chain alkyl having up to six carbon atoms, substituted by an —$OR^6$ group; or
nitro, cyano, —$CO_2R^6$, —$COR^7$, —$S(O)_nR^9$, —$O(CH_2)_mOR^6$, —$N(R^{12})SO_2R^8$, —$OR^{61}$, —$OSO_2R^8$, —$CONR^{10}R^{15}$ or —$(CR^{13}R^{14})_r$—$S(O)_qR^8$;
provided that at least one of $R^2$, $R^3$, $R^4$ and $R^5$ is —$(CR^{13}R^{14})_r$—$S(O)_qR^8$;

$R^6$ is straight- or branched-chain alkyl, alkenyl or alkynyl having up to six carbon atoms, optionally substituted by one or more halogen; or
cycloalkyl having from three to six carbon atoms;

$R^{61}$ is:
straight- or branched-chain alkyl, alkenyl or alkynyl having up to six carbon atoms, optionally substituted by one or more halogen;
cycloalkyl having from three to six carbon atoms; or
phenyl, optionally substituted by from one to five $R^{21}$ groups, which can be the same or different;

$R^7$ is:
straight- or branched-chain alkyl having up to six carbon atoms, optionally substituted by one or more halogen; or
cycloalkyl having from three to six carbon atoms;

$R^8$ is:
straight- or branched-chain alkyl, alkenyl or alkynyl having up to six carbon atoms, optionally substituted by one or more halogen;
cycloalkyl having from three to six carbon atoms;
phenyl, optionally substituted by from one to five $R^{21}$ groups, which can be the same or different; or
—$NR^{10}R^{11}$;

$R^9$ is:
straight- or branched-chain alkyl, alkenyl or alkynyl having up to six carbon atoms, optionally substituted by one or more halogen;
cycloalkyl having from three to six carbon atoms; or
phenyl, optionally substituted by from one to five $R^{21}$ groups, which can be the same or different;

$R^{10}$ is hydrogen or straight- or branched-chain alkyl having up to six carbon atoms, optionally substituted by one or more halogen;

provided that when $R^7$ and $R^{10}$ are part of a group —$CONR^7R^{10}$ they can, together with the nitrogen to which they are attached, form a five or six membered ring optionally having one additional hetero ring atom which is oxygen or nitrogen, said ring being optionally substituted by one or more alkyl, each having up to three carbon atoms;

$R^{11}$ is:
straight- or branched-chain alkyl having up to six carbon atoms, optionally substituted by one or more halogen; or
—$COR^7$, —$CO_2R^7$ or —$CONR^7R^{10}$;
provided that when $R^{10}$ and $R^{11}$ are part of a group —$NR^{10}R^{11}$ they can, together with the nitrogen to which they are attached, form a 5 or 6 membered ring optionally having one additional hetero ring atom which is oxygen or nitrogen, said ring being optionally substituted by one or more alkyl, each having up to three carbon atoms;

$R^{12}$ is:
hydrogen;
straight- or branched-chain alkyl, alkenyl or alkynyl having up to six carbon atoms, optionally substituted by one or more halogen;
cycloalkyl having from three to six carbon atoms;
phenyl, optionally substituted by from one to five $R^{21}$ groups, which can be the same or different; or
—$OR^{17}$;

each of $R^{13}$ and $R^{14}$, which can be the same or different, is hydrogen or straight- or branched-chain alkyl having up to six carbon atoms, optionally substituted by one or more halogen;

$R^{15}$ is $R^7$ or —$OR^{17}$;
provided that when $R^{10}$ and $R^{15}$ are part of a group —$CONR^{10}R^{15}$ they can, together with the nitrogen to which they are attached, form a five or six membered ring optionally having one additional hetero ring atom which is oxygen or nitrogen, said ring being optionally substituted by one or more alkyl each having up to three carbon atoms;

$R^{17}$ is straight- or branched-chain alkyl having up to six carbon atoms;

$R^{21}$ is:
halogen;
straight- or branched-chain alkyl having up to three carbon atoms, optionally substituted by one or more halogen; or
nitro, cyano, —$S(O)_nR^7$ or —$OR^7$;
m is one, two or three;

n is zero, one or two;
q is zero, one or two; and
t is an integer from one to four, provided that when t is greater than one, the groups —($CR^{13}R^{14}$)— can be the same or different;
or an agriculturally acceptable salt, metal complex or enolic tautomeric form thereof.

6. A compound according to claim 5, wherein:

R is:
  straight- or branched-chain alkyl having up to six carbon atoms, optionally substituted by one or more halogen; or
  cycloalkyl having from three to six carbon atoms, optionally bearing one or more methyl substituents;

each of $R^2$, $R^3$, $R^4$ and $R^5$, which can be the same or different, is:
  hydrogen or halogen;
  straight- or branched-chain alkyl, alkenyl or alkynyl having up to six carbon atoms, optionally substituted by one or more halogen;
  straight- or branched-chain alkyl having up to six carbon atoms, substituted by —$OR^6$; or
  —$COR^7$, —$CO_2R^6$, cyano, nitro, —$O(CH_2)_mOR^6$, —$OR^{61}$, —$N(R^{12})SO_2R^8$, —$OSO_2R^8$, —$S(O)_nR^9$ or —$(CR^{13}R^{14})_tS(O)_qR^8$;

each of $R^6$ and $R^7$, which can be the same or different, is:
  straight- or branched-chain alkyl having up to six carbon atoms, optionally substituted by one or more halogen; or
  cycloalkyl having three or four carbon atoms;

each of $R^{61}$ and $R^9$, which can be the same or different, is:
  straight- or branched-chain alkyl or alkenyl having up to six carbon atoms, optionally substituted by one or more halogen;
  straight- or branched-chain alkynyl having from three to six carbon atoms, optionally substituted by one or more halogen; or
  cycloalkyl having three to six carbon atoms;

$R^8$ is:
  straight- or branched-chain alkyl or alkenyl having up to six carbon atoms, optionally substituted by one or more halogen;
  straight- or branched-chain alkynyl having from three to six carbon atoms, optionally substituted by one or more halogen;
  cycloalkyl having three to six carbon atoms; or
  phenyl, optionally substituted by from one to three $R^{21}$ groups, which can be the same or different;

$R^{12}$ is:
  hydrogen;
  straight- or branched-chain alkyl or alkenyl having up to six carbon atoms, optionally substituted by one or more halogen;
  straight- or branched-chain alkynyl having from three to six carbon atoms, optionally substituted by one or more halogen; or
  cycloalkyl having three to six carbon atoms;

each of $R^{13}$ and $R^{14}$, which can be the same or different, is:
  hydrogen; or
  straight- or branched-chain alkyl having up to six carbon atoms, optionally substituted by one or more halogen;

$R^{21}$ is:
  halogen;
  straight- or branched-chain alkyl having up to three carbon atoms, optionally substituted by one or more halogen; or
  nitro, cyano, —$S(O)_nR^7$ or —$OR^7$;
m is two or three;
n is zero, one or two;
q is zero, one or two; and
t is one or two.

7. A compound according to claim 5, wherein:

R is:
  straight- or branched-chain alkyl having up to three carbon atoms; or
  cycloalkyl having three or four carbon atoms, optionally bearing one or more methyl substituents;

each of $R^2$, $R^3$ and $R^4$, which can be the same or different, is:
  hydrogen, chlorine, bromine or fluorine;
  straight- or branched-chain alkyl or alkenyl having up to four carbon atoms, optionally substituted by one or more chlorine, bromine or fluorine;
  straight- or branched-chain alkynyl having up to four carbon atoms;
  straight- or branched-chain alkyl having up to four carbon atoms, substituted by —$OR^6$; or
  —$COR^7$, —$CO_2R^6$, —$S(O)_nR^9$, —$O(CH_2)_mOR^6$, —$N(R^{12})SO_2R^8$, —$OR^{61}$, —$(CR^{13}R^{14})_tS(O)_qR^8$ or —$OSO_2R^8$;
  provided that at least one of $R^2$, $R^3$ and $R^4$ is —$(CR^{13}R^{14})_t$—$S(O)_qR^8$;

$R^5$ is hydrogen;

each of $R^6$, $R^7$, $R^8$ and $R^9$, which can be the same or different, is:
  straight- or branched-chain alkyl having up to four carbon atoms, optionally substituted by one or more chlorine, bromine or fluorine; or
  cyclopropyl;

$R^{61}$ is:
  straight- or branched-chain alkyl or alkenyl having up to four carbon atoms, optionally substituted by one or more chlorine, bromine or fluorine;
  straight- or branched-chain alkynyl having three or four carbon atoms; or
  cyclopropyl;

$R^{12}$ is:
  hydrogen;
  straight- or branched-chain alkyl or alkenyl having up to four carbon atoms, optionally substituted by one or more chlorine, bromine or fluorine;
  straight- or branched-chain alkynyl having three or four carbon atoms; or
  cyclopropyl;

each of $R^{13}$ and $R^{14}$, which can be the same or different, is:
  hydrogen; or
  straight- or branched-chain alkyl having up to three carbon atoms;
m is two or three;
n is zero, one or two;
q is zero, one or two; and
t is one.

8. A compound according to claim 5, wherein:

R is methyl, ethyl, isopropyl, cyclopropyl or 1-methylcyclopropyl;

each of $R^2$, $R^3$ and $R^4$, which can be the same or different, is:
  hydrogen, chlorine, bromine or fluorine;

straight- or branched-chain alkyl or alkenyl having up to four carbon atoms, optionally substituted by one or more chlorine, bromine or fluorine;

straight- or branched-chain alkyl having up to thee carbon atoms, substituted by —$OR^6$; or —$COR^7$, —$CO_2R^6$, —$SR^9$, —$O(CH_2)_mOR^6$, —$OR^{61}$, —$N(R^{12})SO_2R^8$, —$OSO_2R^8$ or —$(CR^{13}R^{14})_tS(O)_qR^8$;

provided that at least one of $R^2$, $R^3$ and $R^4$ is —$(CR^{13}R^{14})_tS(O)_qR^8$;

$R^5$ is hydrogen;

each of $R^6$, $R^7$, $R^8$ and $R^9$, which can be the same or different, is straight- or branched-chain alkyl having up to three carbon atoms;

$R^{61}$ is:
straight- or branched-chain alkyl having up to four carbon atoms, optionally substituted by one or more chlorine, bromine or fluorine;
straight- or branched-chain alkenyl or alkynyl having three or four carbon atoms; or
cyclopropyl;

$R^{12}$ is:
hydrogen;
straight- or branched-chain alkyl group having up to three carbon atoms, optionally substituted by one or more chlorine, bromine or fluorine; or
allyl, optionally substituted by one or more chlorine, bromine or fluorine;

each of $R^{13}$ and $R^{14}$, which can be the same or different, is hydrogen, methyl or ethyl;

m is two or three;

q is zero, one or two; and t is one.

9. A herbicidal composition comprising a herbicidally effective amount of a compound of formula (I) according to claim 2, or an agriculturally acceptable salt, metal complex or enolic tautomeric form thereof, and at least one member of the group consisting of a herbicidally acceptable inert carrier and a herbicidally acceptable surface active agent.

10. A herbicidal composition comprising a herbicidally effective amount of a compound of formula (I) according to claim 5, or an agriculturally acceptable salt, metal complex or enolic tautomeric form thereof, and at least one member of the group consisting of a herbicidally acceptable inert carrier and a herbicidally acceptable surface active agent.

11. A method for controlling the growth of weeds at a locus, said method comprising applying to said locus a herbicidally effective amount of a compound of formula (I) according to claim 1, or an agriculturally acceptable salt, metal complex or enolic tautomeric form thereof.

12. A method for controlling the growth of weeds at a locus, said method comprising applying to said locus a herbicidally effective amount of a compound of formula (I) according to claim 5, or an agriculturally acceptable salt, metal complex or enolic tautomeric form thereof.

13. A compound of formula:

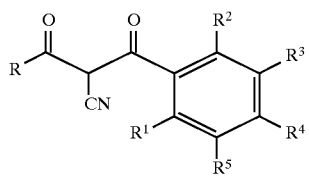

I wherein:

R represents:
straight- or branched-chain alkyl having from 1 to 6 carbon atoms, optionally substituted by one or more halogen which may be the same or different; or
cycloalkyl having from 3 to 6 carbon atoms, optionally bearing one or more substituents which may be the same or different selected from the group consisting of $R^{51}$ and halogen, wherein $R^{51}$ is as defined below;

$R^1$ represents hydrogen;

$R^2$ represents —$S(O)_nCH_3$ or —$S(O)_nCH_2CH_3$ $R^3$ and $R^5$, which may be the same or different, each represents:
halogen or hydrogen, or
straight- or branched-chain alkyl having from 1 to 6 carbon atoms, bearing a substituent —$OR^{51}$, wherein $R^{51}$ is as defined below;
or a member selected from the group consisting of $R^{51}$, cyano, —$OR^{51}$, —$O(CH_2)_mOR^{51}$ and —$CO_2R^{51}$, wherein $R^{51}$ and m are as defined below;

provided that at least one of $R^3$ and $R^5$ is hydrogen;

$R^4$ represents:
halogen or hydrogen, or
straight- or branched-chain alkyl having from 1 to 6 carbon atoms bearing a substituent —$OR^{51}$, wherein $R^{51}$ is as defined below; or
a member selected from the group consisting of $R^{51}$, cyano, —$SR^{41}$, —$OR^{51}$, —$O(CH_2)_mOR^{51}$ and —$CO_2R^{51}$, wherein $R^{51}$, $R^{41}$ and m are as defined below;

$R^{41}$ and $R^{51}$, which may be the same or different, each represents:
straight- or branched-chain alkyl having from 1 to 6 carbon atoms; $R^{51}$ is optionally substituted by one or more halogen which may be the same or different;

m is an integer from 1 to 3; and n is zero, 1 or 2;

with the proviso that when n is zero, $R^4$ does not represent —$SR^{41}$;

an enolic tautomeric form thereof, or an agriculturally acceptable salt of said enolic tautomeric form.

14. The compound according to claim 13, wherein $R^4$ is halogen, hydrogen, or —$OR^{51}$ or $R^{51}$, wherein $R^{51}$ is as defined in claim 60.

15. The compound according to claim 14, wherein halogen is chlorine, bromine or fluorine.

16. The compound according to claim 14, wherein $R^{51}$ is straight- or branched-chain alkyl having from 1 to 4 carbon atoms, optionally substituted by one or more halogen, which may be the same or different.

17. The compound according to claim 16, wherein halogen is chlorine, bromine or fluorine.

18. The compound according to claim 13, wherein R represents methyl, isopropyl, t-butyl, cyclopropyl or 1-methylcyclopropyl.

19. The compound according to claim 13, wherein $R^4$ is halogen, methoxy, ethoxy, trifluoromethoxy, methyl or trifluoromethyl.

20. The compound according to claim 13, wherein $R^3$ and $R^5$, which may be the same or different, each represents halogen, hydrogen, methoxymethyl, methyl, trifluoromethyl, methoxy, ethoxy, isopropoxy, 2-ethoxyethoxy, 2-methoxyethoxy, carbomethoxy, carboethoxy or carboisopropoxy.

21. The compound according to claim 13, wherein $R^{51}$ is methyl, ethyl, isopropyl or trifluoromethyl.

22. The compound according to claim 13, wherein $R^5$ is hydrogen.

23. The compound according to claim 13, wherein R is isopropyl, cyclopropyl or 1-methylcyclopropyl.

24. The compound according to claim 13, wherein $R^4$ represents hydrogen, chlorine, fluorine, bromine, trifluoromethyl, methoxy or methyl.

25. The compound according to claim 13, wherein each of $R^3$ and $R^5$ is hydrogen.

26. The compound according to claim 13, wherein:
R is isopropyl, cyclopropyl or 1-methylcyclopropyl;
$R^4$ represents hydrogen, chlorine, bromine, trifluoromethyl, methoxy or methyl; and
each of $R^3$ and $R^5$ is hydrogen.

27. The compound according to claim 13, wherein:
R represents isopropyl, cyclopropyl or 1-methylcyclopropyl;
$R^3$ represents hydrogen, alkoxy or halogen;
$R^4$ represents hydrogen, chlorine, bromine, trifluoromethyl, methoxy or methyl; and
$R^5$ represents hydrogen.

28. The compound according to claim 13, wherein:
R represents isopropyl, cyclopropyl or 1-methylcyclopropyl;
$R^3$ and $R^5$ each represent hydrogen;
$R^4$ represents hydrogen, chlorine, bromine, trifluoromethyl, methoxy or methyl;
n is zero or 2.

29. The compound according to claim 13, which is:
2-cyano-3-cyclopropyl-1-[2-(methylsulphonyl)phenyl]propan-1,3-dione,
1-[4-chloro-2-(methylsulphonyl)phenyl]-2-cyano-3-cyclopropylpropan-1,3-dione, p0 2-cyano-1-cyclopropyl-3-[2-(ethylsulphonyl)phenyl]propan-1,3-dione,
1-[4-chloro-2-(methylsulphonyl)phenyl]-2-cyano-3-(1-methylcyclopropyl)propan-1,3-dione,
1-[4-chloro-2-(methylsulphonyl)phenyl]-2-cyano-4-methylpentan-1,3-dione,
2-cyano-3-cyclopropyl-1-[4-methyl-2-(methylsulphonyl)phenyl]-propan-1,3-dione,
2-cyano-3-cyclopropyl-1-[4-methoxy-2-(methylsulphonyl)phenyl]propan-1,3-dione,
1-[4-chloro-2-(methylsulphenyl)phenyl]-2-cyano-3-cyclopropylpropan-1,3-dione,
1-[4-bromo-2-(methylsulphonyl)phenyl]-2-cyano-3-cyclopropylpropan-1,3-dione, or
2-cyano-3-cyclopropyl-1-[2-(methylsulphonyl)-4-trifluoromethyl-phenyl]propan-1,3-dione,
or an agriculturally acceptable salt thereof.

30. The compound which is 2-cyano-3-cyclopropyl-1-[2-(methylsulphonyl)-4-trifluoromethylphenyl]propan-1,3-dione, an enolic tautomeric form thereof, or an agriculturally acceptable salt of said enolic tautomeric form.

31. The compound according to claim 13, which is:
2-cyano-3-cyclopropyl-1-(3,4-dichloro-2-methylsulphonylphenyl)propan-1,3-dione,
2-cyano-3-cyclopropyl-1-(3,4-dichloro-2-methylsulphinylphenyl)-propan-1,3-dione,
1-(4-chloro-3-fluoro-2-methylsulphenylphenyl)-2-cyano-3-cyclopropylpropan-1,3-dione,
1-(4-chloro-3-fluoro-2-methylsulphinylphenyl)-2-cyano-3-cyclopropylpropan-1,3-dione,
1-(4-chloro-3-fluoro-2-methylsulphonylphenyl)-2-cyano-3-cyclopropylpropan-1,3-dione,
2-cyano-3-cyclopropyl-1-(3,4-dimethyl-2-methylsulphenylphenyl)propan-1,3-dione,
1-(4-chloro-3-methoxy-2-methylsulphonylphenyl)-2-cyano-3-cyclopropylpropan-1,3-dione,
1-(4-bromo-3-chloro-2-methylsulphenylphenyl)-2-cyano-3-cyclopropylpropan-1,3-dione,
1-(4-bromo-3-chloro-2-methylsulphinylphenyl)-2-cyano-3-cyclopropylpropan-1,3-dione, or
1-(4-bromo-3-chloro-2-methylsulphonylphenyl)-2-cyano-3-cyclopropylpropan-1,3-dione,
or an agriculturally acceptable salt thereof.

32. The compound which is 2-cyano-3-cyclopropyl-1-(3,4-dichloro-2-methylsulphenylphenyl)propan-1,3-dione, an enolic tautomeric form thereof, or an agriculturally acceptable salt of said enolic tautomeric form.

33. A compound of formula:

wherein:
R represents cyclopropyl or methylcyclopropyl;
$R^1$ represents hydrogen;
$R^2$ represents:
halogen, or
straight- or branched-chain alkyl having from 1 to 6 carbon atoms, bearing a substituent —$OR^{51}$; wherein $R^{51}$ is as defined below;
or a member selected from the group consisting of $R^{51}$, cyano, —$SR^{51}$, —$OR^{51}$, —$O(CH_2)_mOR^{51}$, and —$CO_2R^{51}$, wherein $R^{51}$ and m are as defined below;
$R^3$ and $R^5$, which may be the same or different, each represents:
halogen or hydrogen, or
straight- or branched-chain alkyl having from 1 to 6 carbon atoms, bearing a substituent —$OR^{51}$, wherein $R^{51}$ is as defined below;
or a member selected from the group consisting of $R^{51}$, cyano, —$OR^{51}$, —$O(CH_2)_mOR^{51}$ and —$CO_2R^{51}$, wherein $R^{51}$ and m are as defined below;
provided that at least one of $R^3$ and $R^5$ is hydrogen;
$R^4$ represents —$S(O)_nR^{41}$, wherein $R^{41}$ and n are as defined below;
$R^{41}$ and $R^{51}$, which may be the same or different, each represents:
straight- or branched-chain alkyl having from 1 to 6 carbon atoms, $R^{51}$ is optionally substituted by one or more halogen which may be the same or different;
n is zero, 1 or 2; m is an integer from 1 to 3;
an enolic tautomeric form thereof,
or an agriculturally acceptable salt of said enolic tautomeric form.

34. The compound according to claim 33, wherein $R^2$ is halogen, —$OR^{51}$ or $R^{51}$, wherein $R^{51}$ is as defined in claim 33.

35. The compound according to claim 34, wherein halogen is chlorine, bromine or fluorine.

36. The compound according to claim 33, wherein $R^{51}$ is straight- or branched-chain alkyl having from 1 to 4 carbon atoms, optionally substituted by one or more halogen which may be the same or different.

37. The compound according to claim 36, wherein halogen is chlorine, bromine or fluorine.

38. The compound according to claim 33, wherein $R^3$ and $R^5$, which may be the same or different, each represents halogen, hydrogen, straight- or branched-chain alkyl having from 1 to 6 carbon atoms, bearing a substituent —$OR^{51}$; or a member selected from the group consisting of $R^{51}$, —$OR^{51}$, —$O(CH_2)_mOR^{51}$ where m is 2 or 3; and —$CO_2R^{51}$, wherein $R^{51}$ is as defined in claim 33;

provided that at least one of $R^3$ and $R^5$ is hydrogen.

39. The compound according to claim 38, wherein halogen is chlorine, bromine or fluorine.

40. The compound according to claim 38, wherein $R^{51}$ represents straight- or branched-chain alkyl having from 1 to 4 carbon atoms, optionally substituted by one or more halogen which may be the same or different.

41. The compound according to claim 39, wherein $R^{41}$ represents straight- or branched-chain alkyl having from 1 to 4 carbon atoms.

42. The compound according to claim 33, wherein:
   (a) $R^2$ represents halogen, —$OR^{51}$, or $R^{51}$, wherein $R^{51}$ is as defined below;
   (b) $R^3$ and $R^5$, which may be the same or different, each represents halogen, hydrogen, straight- or branched-chain alkyl having from 1 to 6 carbon atoms, bearing a substituent —$OR^{51}$; or a member selected from the group consisting of $R^{51}$, —$OR^{51}$, —$O(CH_2)_mOR^{51}$ where m is 2 or 3, and —$CO_2R^{51}$, wherein $R^{51}$ is as defined below; provided that at least one of $R^3$ and $R^5$ is hydrogen;
   (c) $R^{41}$ represents straight- or branched-chain alkyl having from 1 to 4 carbon atoms;
   (d) $R^{51}$ represents straight- or branched-chain alkyl having from 1 to 4 carbon atoms, optionally substituted by one or more halogen which may be the same or different; and
   (e) halogen is chlorine, bromine or fluorine.

43. The compound according to claim 33, wherein $R^5$ is hydrogen.

44. The compound according to claim 33, wherein $R^2$ represents a member selected from the group consisting of $R^{51}$, cyano, —$SR^{51}$, —$O(CH_2)_mOR^{51}$ and —$CO_2R^{51}$, wherein m is as defined in claim 33 and $R^{51}$ represents straight- or branched-chain alkyl having from 1 to 6 carbon atoms.

45. The compound according to claim 33, wherein $R^2$ is chlorine, bromine, fluorine, trifluoromethyl or methoxy.

46. The compound according to claim 33, wherein $R^3$ is hydrogen, chlorine or methoxy.

47. The compound according to claim 33, wherein $R^{41}$ is methyl or ethyl.

48. The compound according to claim 33, wherein
   $R^2$ represents chlorine, bromine, fluorine, trifluoromethyl or methoxy;
   $R^3$ represents hydrogen, chlorine or methoxy;
   $R^5$ represents hydrogen;
   $R^{41}$ represents methyl or ethyl; and
   n is 0, 1 or 2.

49. The compound according to claim 33, wherein
   $R^2$ represents chlorine, bromine, fluorine, trifluoromethyl or methoxy;
   $R^3$ represents hydrogen, chlorine or methoxy;
   $R^5$ represents hydrogen;
   $R^{41}$ represents methyl or ethyl; and
   n is 0 or 2.

50. The compound according to claim 33, which is:
1-[2-chloro-4-(methylsulphonyl)phenyl]-2-cyano-3-cyclopropylpropan-1,3-dione,
2-cyano-1-[4-(methylsulphonyl)-2-trifluoromethylphenyl]-3-(1-methylcyclopropyl)propan-1,3-dione,
1-[2-chloro-4-(methylsulphenyl)phenyl]-2-cyano-3-cyclopropylpropan-1,3-dione,
2-cyano-3-cyclopropyl-1-[2-fluoro-4-(methylsulphonyl)phenyl]propan-1,3-dione,
1-[2-chloro-4-(ethylsulphonyl)phenyl]-2-cyano-3-cyclopropylpropan-1,3-dione,
2-cyano-3-cyclopropyl-1-[4-(methylsulphenyl)-2-trifluoromethyl-phenyl]propan-1,3-dione,
2-cyano-3-cyclopropyl-1-[4-(methylsulphinyl)-2-trifluoromethyl-phenyl]propan-1,3-dione,
2-cyano-3-cyclopropyl-1-[2-methoxy-4-(methylsulphenyl)phenyl]propan-1,3-dione,
1-[2,3-dichloro-4-(methylsulphonyl)phenyl]-2-cyano-3-(1-methylcyclopropyl)propan-1,3-dione,
1-[2-chloro-3-methoxy-4-(methylsulphonyl)phenyl]-2-cyano-3-cyclopropylpropan-1,3-dione,
1-[2-bromo-4-(methylsulphonyl)phenyl]-2-cyano-3-cyclopropylpropan-1,3-dione,
1-[2-bromo-4-(methylsulphonyl)phenyl]-2-cyano-3-(1-methylcyclopropyl)propan-1,3-dione,
2-cyano-3-(1-methylcyclopropyl)-1-[4-(ethylsulphonyl)-2-trifluoromethylphenyl]propan-1,3-dione,
1-[2-chloro-3-methoxy-4-(methylsulphonyl)phenyl]-2-cyano-3-(1-methylcyclopropyl)propan-1,3-dione, or
1-[2-chloro-4-(methylsulphinyl)phenyl]-2-cyano-3-cyclopropylpropan-1,3-dione,
or an agriculturally acceptable salt thereof.

51. The compound which is 2-cyano-3-cyclopropyl-1-[4-(methylsulphonyl)-2-trifluoromethylphenyl]propan-1,3-dione, an enolic tautomeric form thereof, or an agriculturally acceptable salt of said enolic tautomeric form.

52. The compound according to claim 33, which is:
1-(2-bromo-3-methoxy-4-methylsulphenylphenyl)-2-cyano-3-cyclopropylpropan-1,3-dione,
or an agriculturally acceptable salt thereof.

53. A compound of the formula:

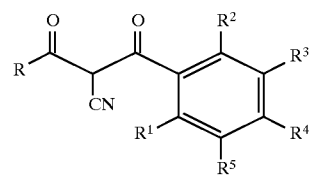

wherein:
   R represents cyclopropyl;
   $R^1$ represents hydrogen;
   $R^2$ represents:
      hydrogen, chlorine or bromine, or
      straight- or branched-chain alkyl having from 1 to 6 carbon atoms, bearing a substituent —$OR^{51}$, wherein $R^{51}$ is as defined below;
      or a member selected from the group consisting of $R^{51}$, cyano, —$S(O)_{p1}R^{41}$, —$OR^{51}$, —$O(CH_2)_mOR^{51}$ and —$CO_2R^{51}$,
   wherein $R^{51}$, $R^{41}$, m and p1 are as defined below;
   $R^3$ represents —$S(O)_nR^{41}$ wherein $R^{41}$ and n are as defined below;
   $R^4$ and $R^5$, which may be the same or different, each represents:
      halogen or hydrogen, or
      straight- or branched-chain alkyl having from 1 to 6 carbon atoms, bearing a substituent —$OR^{51}$, wherein $R^{51}$ is as defined below or
      a member selected from the group consisting of $R^{51}$, cyano, —$OR^{51}$, —$O(CH_2)_mOR^{51}$, —$S(O)_qR^{41}$ and —$CO_2R^{51}$, wherein $R^{51}$, $R^{41}$, m and q are as defined below;
   $R^{41}$ and $R^{51}$, which may be the same or different, each represents:

straight- or branched-chain alkyl having from 1 to 6 carbon atoms, optionally substituted by one or more halogen atoms which may be the same or different;

m is an integer from 1 to 3;

n is zero, 1 or 2; p1 is zero, 1 or 2; q is zero, 1 or 2;

with the proviso that when $R^1$ represents —$S(O)_{p1}R^{41}$ at least one of the substituents p1 and n is zero;

a metal complex thereof, an enolic tautomeric form thereof, or an agriculturally acceptable salt of said enolic tautomeric from.

54. The compound according to claim 53, wherein $R^1$ represents hydrogen, chlorine, bromine, —$OR^{51}$, $R^{51}$, or —$SR^{41}$, $R^{51}$ and $R^{41}$ being as defined in claim 53.

55. The compound according to claim 53, wherein $R^4$ and $R^5$, which may be the same or different, each represents halogen, hydrogen, straight- or branched-chain alkyl having from 1 to 6 carbon atoms, bearing a substituent —$OR^{51}$; $R^{51}$, —$OR^{51}$, —$O(CH_2)_mOR^{51}$ or —$CO_2R^{51}$ or —$S(O)_qR^{41}$, wherein $R^{51}$, $R^{41}$ and q are as defined in claim 53 and m is 2 or 3, provided that at least one of $R^4$ and $R^5$ represent hydrogen.

56. The compound according to claim 53, wherein $R^{41}$ represents straight- or branched-chain alkyl having from 1 to 4 carbon atoms.

57. The compound according to claim 53, wherein $R^{51}$ represents straight- or branched-chain alkyl having from 1 to 4 carbon atoms, optionally substituted by one or more halogen, which may be the same or different.

58. The compound according to claim 53, wherein halogen is chlorine, bromine or fluorine.

59. The compound according to claim 53, wherein:

(a) $R^2$ represents hydrogen, chlorine, bromine, —$OR^{51}$, $R^{51}$, or —$SR^{41}$, $R^{51}$ and $R^{41}$ being as defined in claim 53;

(b) $R^4$ and $R^5$, which may be the same or different, each represents halogen, hydrogen, straight- or branched-chain alkyl having from 1 to 6 carbon atoms, bearing a substituent —$OR^{51}$; $R^{51}$, —$OR^{51}$, —$O(CH_2)_mOR^{51}$ or —$CO_2R^{51}$ or —$S(O)_qR^{41}$, wherein $R^{51}$, $R^{41}$ and q are as defined in claim 33 and m is 2 or 3, provided that at least one of $R^3$ and $R^5$ represent hydrogen;

(c) $R^{41}$ represents straight- or branched-chain alkyl having from 1 to 4 carbon atoms;

(d) $R^{51}$ represents straight- or branched-chain alkyl having from 1 to 4 carbon atoms, optionally substituted by one or more halogen, which may be the same or different; and (e) halogen represents chlorine, bromine or fluorine.

60. The compound according to claim 53, wherein $R^5$ represents hydrogen.

61. The compound according to claim 53, wherein $R^2$ represents hydrogen, chlorine, bromine, methoxy, ethoxy, trifluoromethoxy, methyl, trifluoromethyl or —$SR^{41}$, wherein $R^{41}$ is as defined in claim 53.

62. The compound according to claim 53, wherein $R^4$ and $R^5$, which may be the same or different, each represents halogen, hydrogen, methoxymethyl, methyl, trifluoromethyl, methoxy, ethoxy, isopropoxy, 2-ethoxyethoxy, 2-methoxyethoxy, carbomethoxy, carboethoxy, carboisopropoxy or —$S(O)_qR^{41}$, wherein $R^{41}$ and q are as defined in claim 53, provided that at least one of $R^4$ and $R^5$ represent hydrogen.

63. The compound according to claim 53, wherein $R^{41}$ represents isopropyl, methyl or ethyl.

64. The compound according to claim 53, wherein $R^{51}$ represents methyl, ethyl, isopropyl or trifluoromethyl.

65. The compound according to claim 53, wherein:

$R^2$ represents chlorine, bromine, trifluoromethyl, —$SR^{41}$, methoxy or methyl, wherein $R^{41}$ is as defined below;

$R^4$ represents fluorine, chlorine, bromine, —$CF_3$, —$S(O)_q R^{41}$ or methyl, wherein $R^{41}$ and q are as defined below;

$R^5$ represents hydrogen;

$R^{41}$ represents methyl, ethyl or isopropyl;

$R^{51}$ represents methyl, ethyl or n-propyl;

q is zero, one or two.

66. The compound according to claim 53, which is 2-cyano-3-cyclopropyl-1-(4-methyl-3-methylsulphenylphenyl)propan-1,3-dione, 2-cyano-3-cyclopropyl-1-(4-methyl-3-methylsulphonylphenyl)propan-1,3-dione, 2-cyano-3-cyclopropyl-1-(4-methyl-3-methylsulphinylphenyl)propan-1,3-dione, a metal complex thereof, or an agriculturally acceptable salt thereof.

67. A herbicidal composition comprising a herbicidally effective amount of a compound of the formula I as defined in claim 13 and a herbicidally acceptable diluent therefor, optionally further comprising one or more herbicidally acceptable surface active agents.

68. A herbicidal composition comprising a herbicidally effective amount of a compound of the formula I as defined in claim 33 and a herbicidally acceptable diluent therefor, optionally further comprising one or more herbicidally acceptable surface active agents.

69. A herbicidal composition comprising a herbicidally effective amount of a compound of the formula I as defined in claim 53 and a herbicidally acceptable diluent therefor, optionally further comprising one or more herbicidally acceptable surface active agents.

70. A method for controlling the growth of weeds at a locus, said method comprising applying to said locus a herbicidally effective amount of a compound of the formula I as defined in claim 33.

71. The method according to claim 70, wherein said locus is an area used, or to be used for the growing crops, and between about 0.01 and about 4.0 kg of compound of formula I, enolic tautomeric form thereof or agriculturally acceptable salt thereof is applied per hectare.

72. The method according to claim 71, wherein said crop is maize.

73. A method for controlling the growth of weeds at a locus, said method comprising applying to said locus a herbicidally effective amount of a compound of the formula I as defined in claim 53.

74. The method according to claim 73, wherein said locus is an area used, or to be used for the growing crops, and between about 0.01 and about 4.0 kg of compound of formula I, enolic tautomeric form thereof or agriculturally acceptable salt thereof is applied per hectare.

75. The method according to claim 74, wherein said crop is maize.

76. The compound according to claim 13, wherein each of $R^3$ and $R^5$, which may be the same or different, is halogen, hydrogen, straight- or branched-chain alkyl having up to six carbon atoms which is substituted by —$OR^{51}$, wherein $R^{51}$ is as defined in claim 60; or a member of the group consisting of $R^{51}$, —$OR^{51}$, —$O(CH_2)_mOR^{51}$ wherein m is 2 or 3, and —$CO_2R^{51}$, wherein $R^{51}$ is as defined in claim 60;

provided that at least one of $R^3$ and $R^5$ is hydrogen.

77. The compound according to claim 13, wherein:
(a) $R^4$ is halogen, hydrogen, or a member selected from the group consisting of $-OR^{51}$, and $R^{51}$ seen as $R^{51}$ being as defined below;
(b) $R^3$ and $R^5$, which may be the same or different, each represents halogen, hydrogen, straight- or branched-chain alkyl having from 1 to 6 carbon atoms bearing a substituent $-OR^{51}$, wherein $R^{51}$ is as defined below; or a member selected from the group consisting of $R^{51}$, $-OR^{51}$, $-O(CH_2)_m OR^{51}$ wherein m is 2 or 3, and $-CO_2R^{51}$, wherein $R^{51}$ is as defined below; provided that at least one of $R^3$ and $R^5$ represent hydrogen;
(c) $R^{51}$ represents straight- or branched-chain alkyl having from 1 to 4 carbon atoms, optionally substituted by one or more halogen, which may be the same or different; and
(d) halogen represents chlorine, bromine or fluorine.

78. The compound according to claim 13, wherein:
(a) R represents methyl, isopropyl, t-butyl, cyclopropyl or 1-methylcyclopropyl;
(b) $R^4$ represents halogen, hydrogen, methoxy, ethoxy, trifluoromethoxy, methyl or trifluoromethyl; and
(c) $R^3$ and $R^5$, which may be the same or different, each represents halogen, hydrogen, methoxymethyl, methyl, trifluoromethyl, methoxy, ethoxy, isopropoxy, 2-ethoxyethoxy, 2-methoxyethoxy, carbomethoxy, carboethoxy or carboisopropoxy, provided that at least one of $R^3$ and $R^5$ represent hydrogen.

79. The compound of the formula:

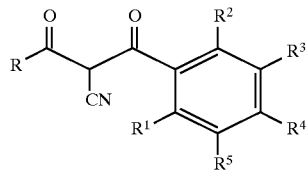

(I)

wherein:
(a) R is cyclopropyl, $R^1$ is hydrogen, $R^2$ is $-N(CH_3)SO_2CH_3$, $R^3$ is hydrogen, $R^4$ is nitro and $R^5$ is hydrogen;
(b) R is cyclopropyl, $R^1$ is hydrogen, $R^2$ is chloro, $R^3$ is hydrogen, $R^4$ is $-N(CH_3)SO_2CH_3$ and $R^5$ is hydrogen;
(c) R is cyclopropyl, $R^1$ is hydrogen, $R^2$ is nitro, $R^3$ is hydrogen, $R^4$ is $-N(CH_3)SO_2CH_3$ and $R^5$ is hydrogen;
(d) R is cyclopropyl, $R^1$ is hydrogen, $R^2$ is $-CH_2SO_2CH_3$, $R^3$ is hydrogen, $R^4$ is bromo and $R^5$ is hydrogen;
(e) R is cyclopropyl, $R^1$ is hydrogen, $R^2$ is $-N(CH_3)SO_2CH_3$, $R^3$ is hydrogen, $R^4$ is chloro and $R^5$ is hydrogen;
(f) R is cyclopropyl, $R^1$ is hydrogen, $R^2$ is $-N(CH_3)SO_2CH_3$, $R^3$ is hydrogen, $R^4$ is methyl and $R^5$ is hydrogen;
(g) R is cyclopropyl, $R^1$ is hydrogen, $R^2$ is chloro, $R^3$ is hydrogen, $R^4$ is $-NHSO_2CH_3$ and $R^5$ is hydrogen;
(h) R is cyclopropyl, $R^1$ is hydrogen, $R^2$ is $-N(CH_2CH_3)SO_2CH_3$, $R^3$ is hydrogen, $R^4$ is chloro and $R^5$ is hydrogen; or
(i) R is cyclopropyl, $R^1$ is hydrogen, $R^2$ is chloro, $R^3$ is hydrogen, $R^4$ is $-CH_2SCH_3$ and $R^5$ is hydrogen;

or an agriculturally acceptable salt, metal complex or enolic tautomeric form thereof.

80. A herbicidal composition comprising a herbicidally effective amount of 2-cyano-3-cyclopropyl-1-[2-(methylsulphonyl)-4-trifluoromethylphenyl]propan-1,3-dione, an enolic tautomeric form thereof, or an agriculturally acceptable salt of said enolic tautomeric form, and a herbicidally acceptable diluent therefor, and optionally further comprising one or more herbicidally acceptable surface active agents.

81. A method for controlling the growth of weeds at a locus, said method comprising applying to said locus a herbicidally effective amount of 2-cyano-3-cyclopropyl-1-[2-(methylsulphonyl)-4-trifluoromethylphenyl]propan-1,3-dione, an enolic tautomeric form thereof, or an agriculturally acceptable salt of said enolic tautomeric form.

82. A process for the preparation of a compound of formula (I) as claimed in claim 1, said process comprising:
(a) treating a compound of the formula

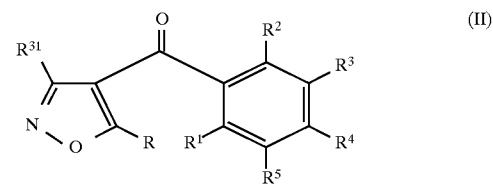

(II)

wherein R, $R^1$, $R^2$, $R^3$, $R^4$ and $R^5$ are as defined is claim 2 and $R^{31}$ is hydrogen or an acyl group, with a base;

(b) subjecting a compound of formula (II) above wherein $R^{31}$ is a carboxylic ester, amide or nitrile, to acidic or basic hydrolysis;

(c) treating a compound of the formula

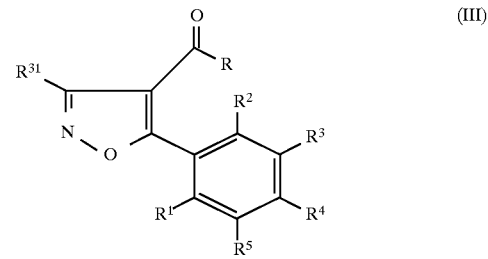

(III)

wherein R, $R^1$, $R^2$, $R^3$, $R^4$ and $R^5$ are as defined in claim 2 and $R^{31}$ is hydrogen or an acyl group, with a base;

(d) subjecting a compound of formula (III) above wherein $R^{31}$ is a carboxylic ester, amide or nitrile, to acidic or basic hydrolysis;

(e) reacting a compound of the formula

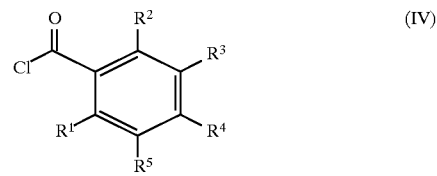

(IV)

wherein $R^1$, $R^2$, $R^3$, $R^4$ and $R^5$ are as defined in claim 2, with a compound of the formula

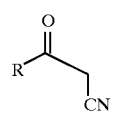

wherein R is as defined in claim 2;

(f) reacting a compound of the formula

wherein R is as defined in claim 2, with a compound of the formula

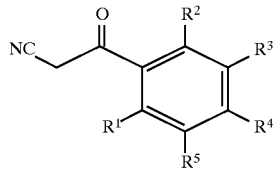

wherein $R^1$, $R^2$, $R^3$, $R^4$ and $R^5$ are as defined in claim 2;

(g) reacting a compound of formula (IV) above with a compound of formula (V) above in the presence of a mild base to form an intermediate of the formula

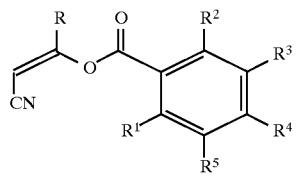

wherein R, $R^1$, $R^2$, $R^3$, $R^4$ and $R^5$ are as defined in claim 2, followed by effecting rearrangement of the intermediate of formula (VIII) in the presence of a catalyst; or (h) reacting a compound of formula (VI) above with a compound of formula (VII) above in the presence of a mild base to form an intermediate of the formula

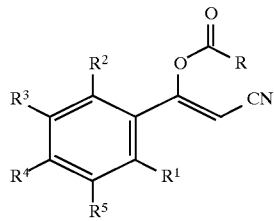

wherein R, $R^1$, $R^2$, $R^3$, $R^4$ and $R^5$ are as defined in claim 2, followed by effecting rearrangement of the intermediate of formula (IX) in the presence of a catalyst.

83. A process for the preparation of a compound of formula (I) as claimed in claim 5, said process comprising:

(a) treating a compound of the formula

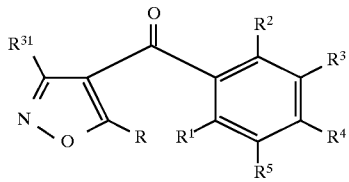

wherein R, $R^1$, $R^2$, $R^3$, $R^4$ and $R^5$ are as defined in claim 6 and $R^{31}$ is hydrogen or an acyl group, with a base;

(b) subjecting a compound of formula (II) above wherein $R^{31}$ is a carboxylic ester, amide or nitrile, to acidic or basic hydrolysis;

(c) treating a compound of the formula

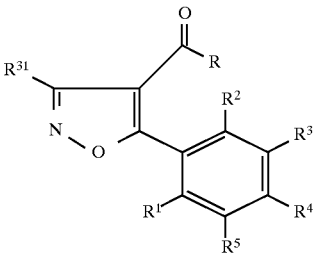

wherein R, $R^1$, $R^2$, $R^3$, $R^4$ and $R^5$ are as defined in claim 6 and $R^{31}$ is hydrogen or an acyl group, with a base;

(d) subjecting a compound of formula (III) above wherein $R^{31}$ is carboxylic ester, amide or nitrile, to acidic or basic hydrolysis;

(e) reacting a compound of the formula

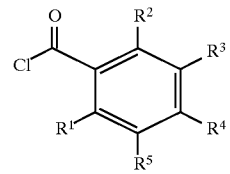

wherein $R^1$, $R^2$, $R^3$, $R^4$ and $R^5$ are as defined in claim 6, with a compound of the formula

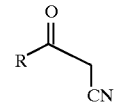

wherein R is as defined in claim 6;

(f) reacting a compound of the formula

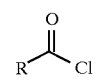

wherein R is as defined in claim 6, with a compound of the formula

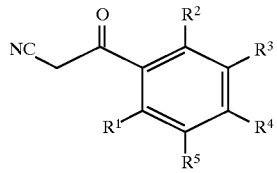

wherein $R^1$, $R^2$, $R^3$, $R^4$ and $R^5$ are as defined in claim 6;

(g) reacting a compound of formula (IV) above with a compound of formula (V) above in the presence of a mild base to form an intermediate of the formula

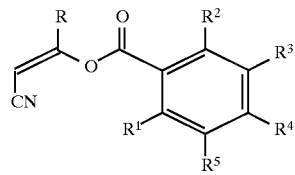

wherein R, $R^1$, $R^2$, $R^3$, $R^4$ and $R^5$ are as defined in claim 6, followed by effecting rearrangement of the intermediate of formula (VIII) in the presence of a catalyst; or (h) reacting a compound of formula (VI) above with a compound of formula (VII) above in the presence of a mild base to form an intermediate of the formula

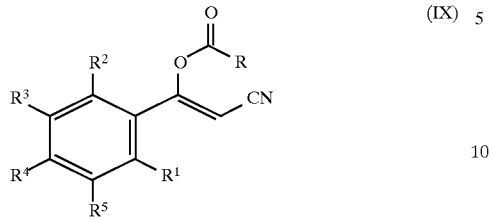

(IX)

wherein R, $R^1$, $R^2$, $R^3$, $R^4$ and $R^5$ are as defined in claim 6, followed by effecting rearrangement of the intermediate of formula (IX) in the presence of a catalyst.

84. A process for the preparation of a compound of formula I as defined in claim 13, said process comprising reacting a compound of the formula

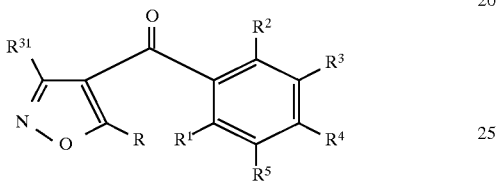

wherein R, $R^1$, $R^2$, $R^3$, $R^4$ and $R^5$ are as defined in claim 60 and $R^{31}$ represents hydrogen or a member of the group consisting of carboxylic ester, amide, nitrile and acyl, with a base.

85. A process for the preparation of a compound of formula I as defined in claim 13, said process comprising reacting a compound of the formula

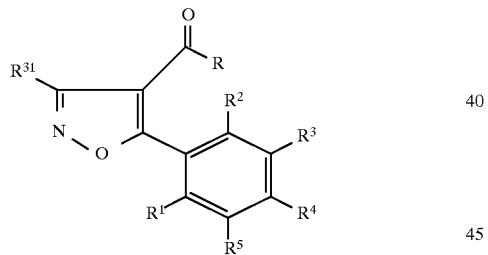

wherein R, $R^1$, $R^2$, $R^3$, $R^4$ and $R^5$ are as defined in claim 60 and $R^{31}$ represents hydrogen or a member of the group consisting of carboxylic ester, amide, nitrile and acyl, with a base.

86. A process for the preparation of a compound of formula I as defined in claim 33, said process comprising reacting a compound of the formula

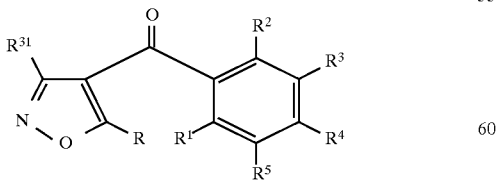

wherein R, $R^1$, $R^2$, $R^3$, $R^4$ and $R^5$ are as defined in claim 33 and $R^{31}$ represents hydrogen or a member of the group consisting of carboxylic ester, amide, nitrile and acyl, with a base.

87. A process for the preparation of a compound of formula I as defined in claim 33, said process comprising reacting a compound of the formula

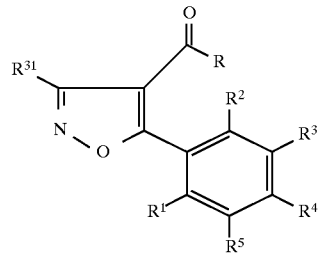

wherein R, $R^1$, $R^2$, $R^3$, $R^4$ and $R^5$ are as defined in claim 33 and $R^{31}$ represents hydrogen or a member of the group consisting of carboxylic ester, amide, nitrile and acyl, with a base.

88. A process for the preparation of a compound of formula I as defined in claim 53, said process comprising reacting a compound of the formula

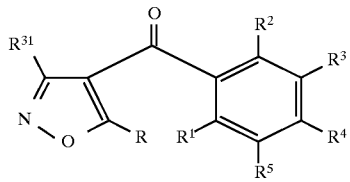

wherein R, $R^1$, $R^2$, $R^3$, $R^4$ and $R^5$ are as defined in claim 53 and $R^{31}$ represents hydrogen or a member of the group consisting of carboxylic ester, amide, nitrile and acyl, with a base.

89. A process for the preparation of a compound of formula I as defined in claim 53, said process comprising reacting a compound of the formula

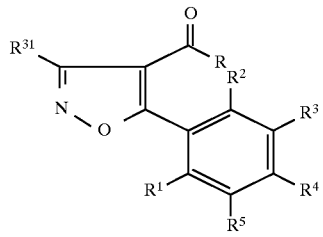

wherein R, $R^1$, $R^2$, $R^3$, $R^4$ and $R^5$ are as defined in claim 53 and $R^{31}$ represents hydrogen or a member of the group consisting of carboxylic ester, amide, nitrile and acyl, with a base.

90. A process for the preparation of 2-cyano-3-cyclopropyl-1-[2-(methylsulphonyl)-4-trifluoromethylphenyl]propan-1,3-dione as claimed in claim 30, said process comprising reacting 5-cyclopropyl-4-[2-(methylsulphonyl)-4-trifluoromethylbenzoyl]isoxazole with a base.

91. A herbicidal composition comprising a herbicidally effective amount of a compound of formula (I) according to claim 79, or an agriculturally acceptable salt, metal complex or enolic tautomeric form thereof, and at least one member of the group consisting of a herbicidally acceptable inert carrier and a herbicidally acceptable surface active agent.

92. A method for controlling the growth of weeds at a locus, said method comprising applying to said locus a herbicidally effective amount of a compound of formula (I) according to claim 79, or an agriculturally acceptable salt, metal complex or enolic tautomeric form thereof.

93. The compound according to claim 78, wherein halogen is chlorine, bromine or fluorine.

94. The compound according to claim 78, wherein $R^{51}$ is straight- or branched-chain alkyl having up to four carbon atoms, substituted by one or more halogen, which may be the same or different.

95. The compound according to claim 94, wherein halogen is chlorine, bromine or fluorine.

* * * * *